US011160826B1

(12) United States Patent
Demorrow et al.

(10) Patent No.: US 11,160,826 B1
(45) Date of Patent: Nov. 2, 2021

(54) CHOLESTEROL LOWERING DRUGS FOR THE TREATMENT OF HEPATIC ENCEPHALOPATHY

(71) Applicant: United States Government as represented by the Department of Veterans Affairs, Washington, DC (US)

(72) Inventors: Sharon Demorrow, Temple, TX (US); Matthew MacMillin, Harker Height, TX (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/663,217

(22) Filed: Oct. 24, 2019

Related U.S. Application Data

(63) Continuation of application No. 15/911,734, filed on Mar. 5, 2018, now abandoned.

(60) Provisional application No. 62/466,587, filed on Mar. 3, 2017.

(51) Int. Cl.
*A61K 31/724* (2006.01)
*A61P 1/16* (2006.01)
*A61P 25/28* (2006.01)

(52) U.S. Cl.
CPC .............. *A61K 31/724* (2013.01); *A61P 1/16* (2018.01); *A61P 25/28* (2018.01)

(58) Field of Classification Search
CPC ........... A61K 31/724; A61P 25/28; A61P 1/16
See application file for complete search history.

(56) References Cited

U.S. PATENT DOCUMENTS

| | | | |
|---|---|---|---|
| 5,316,765 | A | 5/1994 | Folkers et al. |
| 2004/0102525 | A1 | 5/2004 | Kozachuk |
| 2010/0056582 | A1 | 3/2010 | Bayne et al. |
| 2012/0157526 | A1 | 6/2012 | Jalan et al. |
| 2014/0066469 | A1 | 3/2014 | Robinson et al. |
| 2017/0007631 | A1 | 1/2017 | Fayad et al. |
| 2017/0216342 | A1 | 8/2017 | Era et al. |

FOREIGN PATENT DOCUMENTS

| | | | | |
|---|---|---|---|---|
| WO | WO-2000/041531 | A2 | 7/2000 | |
| WO | WO-2009/123029 | | 10/2009 | |
| WO | WO-2009123029 | A1 * | 10/2009 | ............. A23L 33/10 |
| WO | WO-2009/156161 | | 12/2009 | |
| WO | WO-2018/204893 | A1 | 11/2018 | |

OTHER PUBLICATIONS

Loftsson, T. et al "Cyclodextrins in eye drop formulations . . . " Acta Ophthalmol. Scand., vol. 80, pp. 144-150. (Year: 2002).*

Acharya, C. and Bajaj, J.S., Gut Microbiota and Complications of Liver Disease. Gastroenterol Clin North Am. 2017; 46(1):155-69.
Alexander et al., (Acyloxy)alkyl Carbamates as Novel Bioreversible Prodrugs for Amines: Increased Permeation Through Biological Membranes. J Med Chem. 1988; 31(2):318-22.
Almarsson, Ö. et al., Crystal Engineering of the Composition of Pharmaceutical Phases. Do Pharamceutical Co-Crystals Represent a New Path to Improved Medicines? Royal Soc Chem. 2004; 1889-96.
Butterworth, R.F., Experimental Models of Hepatic Encephalopathy: ISHEN Guidelines. Liver Int. 2009; 29(6):783-8.
Butterworth, R.F., Neurosteroids in Hepatic Encephalopathy: Novel Insights and New Therapeutic Opportunities. J Steroid Biochem Mol Biol. 2016; 160:94-7.
Cartocci, V. et al., Can Cholesterol Metabolism Modulation Affect Brain Function and Behavior? J Cell Physiol. 2017; 232(2):281-6.
Chastre, A. et al., Ammonia and Proinflammatory Cytokines Modify Expression of Genes Coding for Astrocytic Proteins Implicated in Brain Edma in Acute Liver Failure. Metab Brain Dis. 2010; 25(1):17-21.
Chastre, A. et al., Lipopolysaccharide Precipitates Hepatic Encephalopathy and Increases Blood-Brain Barrier Permeability in Mice with Acute Liver Failure. Liver Int. 2014; 34(3):353-61.
Chen, Q.-F. et al., Machine Learning Classification of Cirrhotic Patients with and without Minimal Hepatic Encephalopathy Based on Regional Homogeneity of Intrinsic Brain Activity. PLoS One. 2016; 11(3):e0151263 (15 pages).
Courtney, R. and Landreth, G.E., LXR Regulation of Brain Cholesterol: From Development to Disease. Trends Endocrinol Metab. 2016; 27(6):404-14.
Cuddy, L.K. et al., Regulation of the High-Affinity Choline Transporter Activity and Trafficking by Its Association with Cholesterol-Rich Lipid Rafts. J Neurochem. 2014; 128(5):725-40.
Davidson, C.D. et al., Chronic Cyclodextrin Treatement of Murine Niemann-Pick C Disease Ameliorates Neuronal Cholesterol and Glycosphingolipid Storage and Disease Progression. PLoS One. 2009; 4(9):e6951.
DeBarber, A.E. et al., Smith-Lemli-Opitz Syndrome. Exp Rev Mol Med. 2011; 13:e24 (24 pages).
DeMorrow, S. et al., The Endocannabinoid Anandamide Inhibits Cholangiocarcinoma Growth via Activation of the Noncanonical Wnt Signaling Pathway. Am J Physiol Gastrointest Liver Physiol. 2008; 295(6):G1150-8.
Erickson, S.K. et al., Hypercholesterolemia and Changes in Lipid and Bile Acid Metabolism in Male and Female cyp7A1-Deficient Mice. J Lipid Res. 2003; 44(5):1001-9.
Felipo, V. et al., Contribution of Hyperammonemia and Inflammatory Factors to Cognitive Impairment in Minimal Hepatic Encephalopathy. Metab Brain Dis. 2012; 27(1):51-8.
Frampton, G. et al., Interleukin-6-driven Progranulin Expression Increases Cholangiocarcinoma Growth by an Akt-Dependent Mechanism. Gut. 2012; 61(2):268-77.

(Continued)

*Primary Examiner* — Leigh C Maier
(74) *Attorney, Agent, or Firm* — Ballard Spahr LLP

(57) ABSTRACT

The present disclosure is concerned with cholesterol lowering agents including, but not limited to, statins and cyclodextrins, for the treatment of hepatic encephalopathy. This abstract is intended as a scanning tool for purposes of searching in the particular art and is not intended to be limiting of the present invention.

3 Claims, 56 Drawing Sheets

Specification includes a Sequence Listing.

(56) References Cited

OTHER PUBLICATIONS

Hori, T. et al., Fulminant Liver Failure Model with Hepatic Encephalopathy in the Mouse. Ann Gastroenterol. 2011; 24(4):294-306.
Horvatitis, T. et al., Serum Bile Acids as Marker for Acute Decompensation and Acute-on-Chronic Liver Failure in Patients with Non-Cholestatic Cirrhosis. Liver Int. 2017; 37(2):224-31.
Jayakumar, A.R. et al., Brain Edema in Acute Liver Failure: Role of Neurosteroids. Arch Biochem Biophys. 2013; 536(2):171-5.
Kawamata, Y. et al., A G Protein-Coupled Receptor Responsive to Bile Acids. J Biol Chem. 2003; 278(11):9435-40.
Klein, A.D. et al., The Unique Case of the Niemann-Pick Type C Cholesterol Storage Disorder. Pediatr Endocrinol Rev. 2014; 12 Suppl 1:166-75.
Leoni, V. and Caccia, C., The Impairment of Cholesterol Metabolism in Huntington Disease. Biochem Biophys Acta. 2015; 1851(8):1095-105.
Livak, K.J. and Schmittgen, T.D., Analysis of Relative Gene Expression Data Using Realtime Quantitative PCR and the $2(-\Delta\Delta C_T)$ Method. Methods. 2001; 25(4):402-8.
Lund, E.G. et al., Knockout of the Cholesterol 24-Hydoxylase Gene in Mice Reveals a Brain-Specific Mechanism of Cholesterol Turnover. J Biol Chem. 2003; 278(25):22980-8.
McMillin, M. and DeMorrow, S., Effects of Bile Acids on Neurological Function and Disease. FASEB J. 2016; 30(11):3658-68.
McMillin, M. et al., Bile Acid Signaling is Involved in the Neurological Decline in a Murine Model of Acute Liver Failure. Am J Pathol. 2016; 186(2):312-23.
McMillin, M. et al., Bile Acid-Mediated Sphingosine-1-Phosphate Receptor 2 Signaling Promotes Neuroinflammation During Hepatic Encephalopathy in Mice. Front Cell Neurosci. 2017; 11:191 (13 pages).
McMillin, M. et al., Fractalkine Suppression During Hepatic Encephalopathy Promotes Neuroinflammation in Mice. J Neuroinflammation. 2016; 13(1):198 (12 pages).
McMillin, M. et al., Gli1 Activation and Protection Against Hepati Encephalopathy is Suppressed by Circulating Transforming Growth Factor β1 in Mice. J Hepatol. 2014; 61(6):1260-6.
McMillin, M. et al., Suppression of the HPA Axis During Cholestasis Can Be Attributed to Hypothalamic Bile Acid Signaling. Mol Endocrinol. 2015; 29(12):1720-30.
McMillin, M.A. et al., TGFβ-1 Exacerbates Blood-Brain Barrier Permeability in a Mouse Model of Hepatic Encephalopathy via Upregulation of MMP9 and Downregulation of Claudin-5. Lab Invest. 2015; 95(8):903-13.
Megías-Vericat, J.E. et al., Early Experience with Compassionate Use of 2 Hydroxypropyl-beta-Cyclodextrin for Niemann-Pick Type C Disease: Review of Initial Published Cases. Neurol Sci. 2017; 38(5):727-43.
Métais, C. et al., Simvastatin Increases Excitability in the Hippocampus via a PI3 Kinase-Dependent Mechanism. Neuroscience. 2015; 291:279-8.
Milagre, I. et al., Transcriptional Regulation of the Human CYP46A1 Brain-Specific Expression by Sp Transcription Factors. J Neurochem. 2008; 106(2):835-49.
Nardone, R. et al., Intracortical Inhibitory and Excitatory Circuits in Subjects with Minimal Hepatic Encephalopathy: a TMS Study. Metab Brain Disease. 2016; 31(5):1065-70.
Nguyen, J.H. et al., Matrix Metalloproteinase-9 Contributes to Brain Extravasation and Edema in Fulminant Hepatic Failure Mice. J Hepatol. 2006; 44(6):1105-14.

Orth, M. and Bellosta, S., Cholesterol: Its Regulation and Role in Central Nervous System Disorders. Cholesterol. 2012; 2012:292598 (19 pages).
Ory, D.S. et al., Intrathecal 2-hydroxypropyl-β-cyclodextrin Decreases Neurological Disease Progression in Niemann-Pick Disease, Type C1: a Non-Ranomised, Open-label, Phase 1-2 Trial. Lancet. 2017; 390(10104):1758-68.
Pol, A. et al., A Caveolin Dominant Negative Mutant Associates with Lipid Bodies and Induces Intracellular Cholesterol Imbalance. J Cell Biol. 2001; 152(5):1057-70.
Powell, E. et al., The Splay Angle: A New Measure for Assessing Neuromuscular Dysfunction in Rats. Physiol Behav. 1999; 67(5):819-21.
Pucadyil, T.J. and Chattopadhyay, A., Role of Cholesterol in the Function and Organization of G-Protein Coupled Receptors. Prog Lipid Res. 2006; 45(4):295-333.
Quinn, M. et al., Bile Acids Permeabilize the Blood Brain Barrier After Bile Duct Ligation in Rats via Rac1-dependent Mechanisms. Dig Liver Dis. 2014; 46(6):527-34.
Smith, A. J., Cholesterol-Dependent Kinase Activity Regulates Transmitter Release from Cerebellar Synapses. J Neurosci. 2010; 30(17):6166-21.
Song, P. et al., Individual Bile Acids Have Differential Effects on Bile Acid Signaling in Mice. Toxicol Appl Pharmacol. 2015; 283(1):57-64.
Tu, A.-Y. and Albers, J.J., Functional Analysis of the Transcriptional Activity of the Mouse Phospholipid Transfer Protein Gene. Biochem Biophys Res Commun. 2001; 287(4):921-6.
Vance, J.E. and Peake, K.B., Function of the Niemann-Pick Type C Proteins and Their Bypass by Cyclodextrin. Curr Opin Lipidol. 2011; 22(3):204-9.
Vance, J.E., Dysregulation of Cholesterol Balance in the Brain: Contribution to Neurodegenerative Diseases. Dis Model Mech. 2012; 5(6):746-55.
Vanier, M.T. and Latour, P., Laboratory Diagnosis of Niemann-Pick Disease Type C: the Filipin Staining Test. Method Cell Biol. 2015; 126:357-75.
McMillin, et al., FXR-Mediated Cortical Cholesterol Accumulation Contribute to the Pathogenesis of Type A Hepatic Encephalopathy. Cellular and Molecular Gastroenterology and Hepatology 2018; 6(1): 47-63.
Zidovetzki, et al., Use of Cyclodextrins to Manipulate Plasma Membrane Cholesterol Content: Evidence Misconceptions and Control Strategies. Biochimica et Biophysica Acta 2007; 1768(6): 1311-1324.
International Search Report and Written Opinion dated May 14, 2019 by the International Search Authority for International Application No. PCT/US19/20322, filed on Mar. 1, 2019 (Applicant—The United States Government as represented by the Department of Veterans Affairs) (10 pages).
Requirement for Restriction dated Feb. 7, 2019 by the U.S. Patent and Trademark Office for U.S. Appl. No. 15/911,734, filed Mar. 5, 2018 (8 pages).
Response to Requirement for Restriction filed on Apr. 1, 2019 with the U.S. Patent and Trademark Office for U.S. Appl. No. 15/911,734, filed Mar. 5, 2018 (7 pages).
Non-final Office Action dated May 29, 2019 by the U.S. Patent and Trademark Office for U.S. Appl. No. 15/911,734, filed Mar. 5, 2018 (7 pages).

* cited by examiner

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: synthetic construct; FXR Morpholino

<400> SEQUENCE: 1

Cys Thr Gly Ala Ala Ala Cys Thr Gly Cys Ala Thr Cys Ala Cys Cys
1               5                   10                  15

Ala Thr Cys Cys Thr Thr Ala Gly Cys
            20                  25

<210> SEQ ID NO 2
<211> LENGTH: 25
<212> TYPE: PRT
<213> ORGANISM: Artificial Sequence
<220> FEATURE:
<223> OTHER INFORMATION: synthetic construct; FXR Mismatch Morpholino

<400> SEQUENCE: 2

Cys Thr Cys Ala Ala Ala Gly Thr Gly Gly Ala Thr Cys Ala Cys Cys
1               5                   10                  15

Ala Thr Cys Gly Thr Thr Ala Cys Cys
            20                  25
```

CHOLESTEROL LOWERING DRUGS FOR THE TREATMENT OF HEPATIC ENCEPHALOPATHY

CROSS-REFERENCE TO RELATED APPLICATIONS

This application is a continuation of U.S. application Ser. No. 15/911,734, filed Mar. 5, 2018, which claims the benefit of U.S. Provisional Application No. 62/466,587, filed on Mar. 3, 2017, which is incorporated herein by reference in its entirety.

STATEMENT REGARDING FEDERALLY SPONSORED RESEARCH

This invention was made with government support under grant number DK082435 awarded by the National Institutes of Health and grant numbers BX002638 and BX003486 by the United States Department of Veterans Affairs Biomedical Laboratory Research and Development Service. The government has certain rights in the invention.

REFERENCE TO SEQUENCE LISTING

The Sequence Listing submitted on Feb. 5, 2020 as a text file named "37759_0054U2_ST25.txt," created on Feb. 4, 2020, and having a size of 1,086 bytes is hereby incorporated by reference pursuant to 37 C.F.R. § 1.52(e)(5).

BACKGROUND

Hepatic encephalopathy is a term used to describe the broad spectrum of neurological complications that arise from acute liver failure (type A hepatic encephalopathy), portosystemic shunt without liver disease (type B hepatic encephalopathy) and liver cirrhosis (type C hepatic encephalopathy). These complications range from mild confusion, learning and memory impairment (which are hallmarks of minimal hepatic encephalopathy) through to neuromuscular impairment, asterixis, and ataxia (indications of overt hepatic encephalopathy) and ultimately hepatic coma at late stages of the disease progression. Associated with hepatic encephalopathy are cerebral edema, increased intracranial pressure (particularly in acute liver failure), hyperammonemia and neuroinflammation, although the molecular pathogenesis by which hepatic encephalopathy occurs is poorly understood.

A role for aberrant bile acid signaling in the neurological dysfunction associated with hepatic encephalopathy has been demonstrated in a mouse model of acute liver failure (McMillin, M. et al. (2016) *Am. J. Pathol.* 186(2): 312-23). Specifically, total bile acid content is increased in brain tissue during acute liver failure (McMillin, M. et al. (2016) *Am. J. Pathol.* 186(2): 312-23) and these bile acids can be taken up into neurons via the apical sodium bile acid transporter (McMillin, M. et al. (2015) *Mol. Endocrinol.* 29(12):1720-30) where they can activate the bile acid nuclear receptor farnesoid X receptor (FXR) and increase the expression of the FXR target gene, small heterodimer partner (SHP). Furthermore, strategies to reduce the circulating bile acid concentration by cholestyramine feeding, using mice with genetic deletion of Cytochrome p450 7A1 (CYP7A1) or specifically blocking FXR in the brain attenuated the neurological dysfunction associated with hepatic encephalopathy without altering the underlying liver damage (McMillin, M. et al. (2016) *Am. J. Pathol.* 186(2): 312-23). Without wishing to be bound by theory, these data suggest that aberrant bile acid signaling in the brain may play a role in the development of hepatic encephalopathy, although the downstream consequences of this signaling are unknown.

Approximately 25% of the body's cholesterol is found in the brain and the levels are tightly regulated so that fluctuations in dietary cholesterol have minimal effect on brain function (Orth and Bellosta (2012) *Cholesterol* 2012: 292598). In the brain, cholesterol is either incorporated into the cell membrane, where it regulates signal transduction pathways, or it can influence synapse formation, action potentials, and neurotransmitter release (Cartocci et al. (2017) *J. Cell Physiol.* 232(2): 281-6). Furthermore, intracellular cholesterol serves as the precursor for the synthesis of many neurosteroids synthesized in the brain, such as allopregnanolone (Cartocci et al. (2017) *J. Cell Physiol.* 232(2): 281-6). One of the major ways in which the brain clears cholesterol is via its conversion to 24-(S)-hydroxycholesterol, a reaction catalyzed by the enzyme Cytochrome p450 46A1 (Cyp46A1) (Lund et al. (2003) *J. Biol. Chem.* 278(25): 22980-8). 24-(S)-hydroxycholesterol is then able to exit the brain and enter the blood stream where it is integrated into the de novo bile acid synthesis pathway in the liver (Lund et al. (2003) *J. Biol. Chem.* 278(25): 22980-8). Given that bile acids are known to regulate key steps in their biosynthesis pathway, it is conceivable the aberrant bile acid signaling in the brain may influence the cholesterol clearance pathway.

In sum, despite the known severity of hepatoic encephalopathy, current treatment methods are limited by the lack of knowledge surrounding the molecular pathogenesis of the disorder. Thus, there remains a need for methods and compositions for the treatment of hepatic encephalopathy based on improved understanding of the disease.

SUMMARY

In accordance with the purpose(s) of the invention, as embodied and broadly described herein, the invention, in one aspect, relates to methods and compositions for the treatment of hepatic encephalopathy.

Disclosed are methods for the treatment of hepatic encephalopathy in a subject diagnosed with a need for treatment of hepatic encephalopathy, the method comprising administering to the subject a therapeutically effective amount of a cholesterol reducing agent.

Also disclosed are methods for modifying liver X receptor beta (LXRβ) signaling in a subject diagnosed with a need for modification of LXRβ, the method comprising administering to the subject a therapeutically effective amount of a cholesterol reducing agent.

Also disclosed are methods for modifying liver X receptor beta (LXRβ) signaling in at least one cell, the method comprising contacting the cell with an effective amount of a cholesterol reducing agent.

Also disclosed are kits comprising a cholesterol reducing agent and one or more of: (a) at least one agent associated with the treatment of hepatic encephalopathy; (b) at least one agent associated with the treatment of liver failure; (c) at least one liver protective agent; (d) instructions for treating hepatic encephalopathy; (e) instructions for treating liver failure; (f) instructions for administering the cholesterol reducing agent in connection with reducing the risk of liver failure; and (g) instructions for administering the cholesterol reducing agent in connection with protecting a liver.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1A:
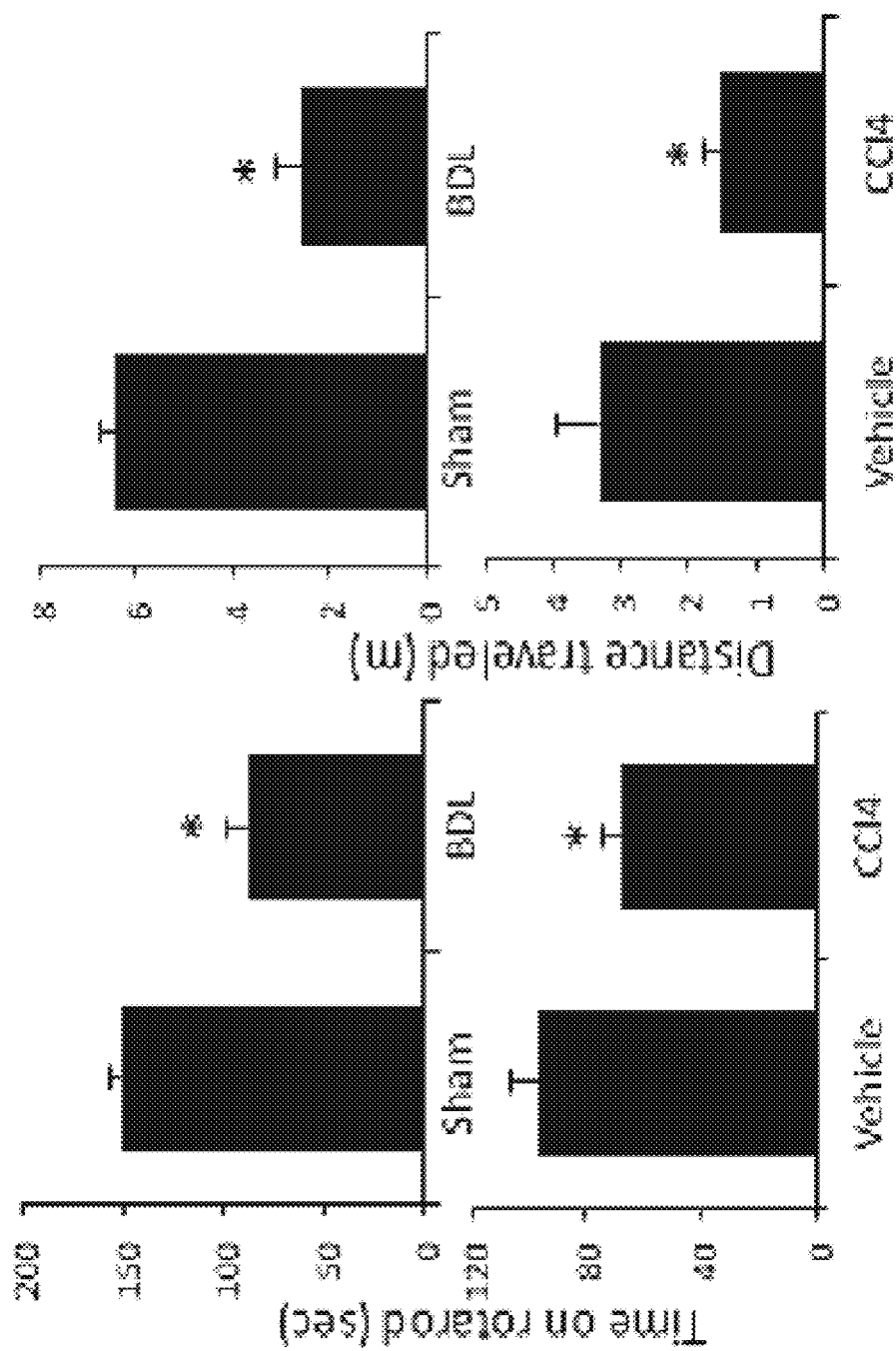
FIG. 1A-D show representative data characterizing HE in BDL rats and CCl4-treated mice.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cholesterol reducing agent" refers an agent that reduces brain cholesterol levels. In certain aspects, a cholesterol reducing agent can be a drug that, upon administration to a subject, decreases brain cholesterol levels by, for example, 1%, 2%, 3%, 4%, 5%, 10%, 15%, 20%, 25%, 30%, 50%, or 75%. In further aspects, the cholesterol reducing agent can be a statin (e.g., atorvastatin, fluvastatin, lovastatin, pravastatin, rosuvastatin, simvastatin). In further aspects, the cholesterol reducing agent can be a cyclodextrin (e.g., α-cyclodextrin, a β-cyclodextrin, methyl-β-cyclodextrin, a γ-cyclodextrin, 2-hydroxypropyl-α-cyclodextrin, 2-hydroxypropyl-β-cyclodextrin, methylated β-cyclodextrin, hydroxyethyl-β-cyclodextrin, sulfobutylether β-cyclodextrin, and 2-hydroxypropyl-γ-cyclodextrin). In further aspects, the cholesterol reducing agent can be a LXR ligand/agonist (e.g., LXR-623, 24-S hydroxycholesterol, GW 3965 hydrochloride, T 0901317, SR 9243, WAY 252623, SR 9238, 27-Hydroxycholesterol). In further aspects, the cholesterol reducing agent can be a bile acid sequestrant (e.g., Cholestyramine, Colestipol, Colesevelam).

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance.

The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compounds and compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. BILE ACID SIGNALING AND HEPATIC ENCEPHALOPATHY

Hepatic encephalopathy (HE) is a serious neuropsychiatric complication of both acute liver failure and chronic liver disease with the potential to affect health-related quality of life, clinical management strategies, priority for liver transplantation and patient survival. HE resulting from acute liver failure (Type A HE) causes altered mental states and cognitive disruptions that can progress to coma in hours or days. In the setting of cirrhosis, Type C HE develops slowly with many patients having altered sleep patterns and cognitive issues that can progress to more severe symptomology if there is no therapeutic intervention given. Given the poor treatment options for the management of liver cirrhosis and the advances in the clinical diagnosis of cognitive symptoms, the prevalence of HE is increasing with an urgent need to develop effective treatment options for these patients. The current understanding of the pathogenesis of hepatic encephalopathy has largely focused on the buildup of serum and cortical ammonia, which can act synergistically with peripheral and central inflammation to precipitate the neurological difficulties observed during HE. However, the increase of circulating bile acids has been identified as another possible culprit contributing to the complex etiology of HE, although the specific mechanisms and downstream consequences of aberrant bile acid signaling in the brain is unknown. Therapies designed to detoxify the blood are often successful in alleviating the symptoms of mild or minimal HE but the treatment options for patients with more severe HE are limited, with liver transplantation being one of the only options that significantly enhances the chance of survival for these patients. Thus, there is significant need for the development of therapeutic strategies to help with quality of life improvement and overall survival of patients with severe HE.

Bile acids are pleiotropic molecules produced predominantly in the liver using cholesterol as their chemical backbone. They are secreted into the intestine where they aide in the digestion and absorption of lipids. Various membrane-bound and nuclear receptors are responsive to different bile acids. The quintessential bile acid receptor is the nuclear receptor farnesoid x receptor (FXR). Bile acid ligands gain entry to the nuclear receptor either by passive diffusion into the cell or via active transport through one of the many bile acid transporters (e.g. apical sodium-dependent bile acid transporter (ASBT), organic anion-transporting polypeptide (OATP), or sodium taurocholate co-transporting polypeptide (NTCP)). More recently, certain bile acids have also been identified as ligands for a number of other nuclear receptors, including pregnane X receptor, vitamin D receptor, and the glucocorticoid receptor.

Interestingly, a number of membrane-bound bile acid receptors have also been identified. Most studies have focused on Takeda G-protein coupled receptor 5 (TGR5) that can bind and be activated by unconjugated bile acids thus increasing intracellular 3',5'-cyclic adenosine monophosphate. However, more recent reports suggest that sphingosine 1-phophate receptor 2 (S1P2R) is also responsive to bile acids, in particular to conjugated bile acids, resulting in the activation of ERK1/2 and Akt-dependent pathways.

The majority of the bile acids secreted into the duodenum from the liver are taken up by the enterocytes of the ileum via active transport, secreted into the portal circulation and are recirculated back into the liver. However, in conditions where the liver is damaged, serum bile acids are increased, possibly due to the release of bile acids from damaged hepatocytes, as well as from impaired reuptake of bile acids in the blood stream. The increase in total bile acid content in the serum, as a result of liver damage, occurs in many acute and chronic liver disorders to varying degrees. Indeed, this increase has been suggested to have predictive value for the onset of acute decompensation and acute-on-chronic liver failure in patients with cirrhosis, both of which are often associated with the development of HE.

The total bile acid concentration in the serum is the summation of the concentrations of each individual bile acid, and as indicated above, the different bile acid species have different properties and affinities for various receptors. Therefore, determining the link between individual bile acid species and the development of HE is important. In an analysis of serum bile acids in patients with early and advanced cirrhosis there was increased total bile acid content, as well as increased levels of conjugated bile acids which correlated with the severity of the disease. There was also increased prevalence of primary bile acids over secondary bile acids in the stool of these patients, which correlated with alterations in the gut microbiome, suggesting a correlation between gut microbiome, individual bile acid species, and the severity of liver cirrhosis.

Early studies have demonstrated that bile acids can be found in the brain. Whether these bile acids are transported to the brain from the periphery or are as a result of de novo bile acid synthesis in the brain via cholesterol oxidation is unknown. Elevation of total bile acid levels in the cerebrospinal fluid (CSF) have been observed in patients with fulminant hepatic failure. More recently, increases in certain bile acids, particularly taurocholic acid (TCA) and glycocholic acid (GCA) were detected in the CSF of patients with Type C HE as part of a larger metabolic screen, although whether bile acids in the CSF can alter neurological function is uncertain. More importantly, it was recently demonstrated increased total bile acid content in brain tissue in a rodent model of Type A HE, specifically, increased levels of TCA. Similarly, increased total bile acid content in brain tissue has been detected as an early event in a model of chronic liver damage prior to the onset of HE, suggesting that bile acids may play a role in HE pathogenesis regardless of the underlying liver pathology. Increased bile acid content in the CSF also has been discovered in a number of other pediatric and adult neurological disorders, including Niemann-Pick Type C, amyotrophic lateral sclerosis, and other neurological disorders. The source of these bile acids and their contribution to the pathogenesis of these diseases are unknown.

A role for aberrant bile acid signaling in the neurological dysfunction associated with HE was previously demonstrated using a mouse model of acute liver failure. Specifically, mice fed a diet enriched with the bile acid sequestrant cholestyramine had reduced serum and brain bile acid content, which alleviated the neurological impairments associated with HE such as reflex deficits and the presence of ataxia. Furthermore, altering the relative composition of the bile acid pool by feeding mice a diet enriched in cholic acid or deoxycholic acid (DCA) worsened the neurological decline associated with acute liver failure. Identification of the mechanism(s) of action by which bile acids may alter the neurological function in mice with acute liver failure began with demonstrating that expression of the bile acid transporter ASBT colocalized with neuronal markers in various brain regions, including the frontal cortex, which has been confirmed in other neurological disorder models. In vitro, the uptake into neurons of a fluorescent bile acid derivative, cholyl-lysyl fluorescein (CLF), was inhibited by the specific knockdown of ASBT expression. Once inside the neuron, it is hypothesized that bile acids exert effects primarily through the activation of FXR. In support of this notion, FXR expression has been demonstrated predominantly in neurons throughout the brain and the expression of FXR and its cofactor SHP is increased in the frontal cortex during acute liver failure. Furthermore, the direct infusion of an FXR-specific vivo morpholino into the frontal cortex proved to be protective against the neurological complications of acute liver failure.

Many possible downstream effects of FXR signaling may be involved in the pathogenesis of HE. One possibility may lie in the mechanisms by which the brain maintains cholesterol homeostasis. Approximately 25% of the body's cholesterol is found in the brain; and the levels are tightly regulated ensuring that fluctuations in dietary cholesterol have a minimal effect on brain function. In the brain, cholesterol is incorporated into the cell membrane, where it regulates signal transduction pathways, or influences synapse formation, action potentials, and neurotransmitter release. Furthermore, intracellular cholesterol serves as the precursor for the synthesis of many neurosteroids that are synthesized in the brain, such as allopregnanolone. One of the major ways in which the brain clears cholesterol is via its conversion to 24-(S)-hydroxycholesterol, a reaction catalyzed by the enzyme Cytochrome p450 46A1(Cyp46A1). 24-(S)-hydroxycholesterol is then able to exit the brain and enter the blood stream where it is integrated into the de novo bile acid synthesis pathway in the liver. In general, the bile acid synthesis pathways in the liver are tightly regulated and controlled by bile acid signaling via a negative feedback loop. It is conceivable that aberrant bile acid signaling in the brain may alter these cholesterol clearance pathways to bring about alterations in neurotransmitter release and/or neurosteroid synthesis, both of which are known to be altered in hepatic encephalopathy.

Neurosteroid synthesis in the brain occurs predominantly in glia and principal neurons using cholesterol as a precursor. Astrocytes and neurons express cytochrome p450 cholesterol side-chain cleavage enzyme (Cyp450scc), which converts cholesterol to pregnenolone, an intermediate necessary for the synthesis of neurosteroids. Neurosteroids, such as allopregnanolone and tetrahydrodeoxycorticosterone, are increased in the frontal cortex, cerebellum and hippocampus of patients with HE as well as in rodent models. These neurosteroids have potent positive allosteric modulatory action on the GABA-A receptor complex, leading to decreased neuronal activity observed in HE.

The biosynthesis of neurosteroids is controlled by the translocator protein (18 kD; TSPO), formerly called peripheral or mitochondrial benzodiazepine receptor. TSPO is widely found in peripheral tissues and in the brain where it is mainly located in the outer mitochondrial membrane and transports cholesterol to the inner mitochondrial membrane, ultimately promoting neurosteroid synthesis. Activation of this protein by certain ligands facilitates the mitochondrial flux of cholesterol, thereby increasing the bioavailability of cholesterol to the CYP450scc and subsequent neurosteroid synthesis. The selective ligands of TSPO can stimulate neurosteroid biosynthesis in the brain, confirming the key role for TSPO in neurosteroidogenesis. TSPO expression and ligand binding activity are also increased in rodent models and patients with HE. Precisely what is driving the increased neurosteroid synthesis and TSPO expression in HE is largely unknown.

United States Veterans have a high risk of developing liver cirrhosis due, at least in part, to the high prevalence of alcohol and drug abuse. The prevalence of cirrhosis has been increasing in the Veteran Affairs Healthcare System (up 59% from 2001 to 2013) with over 1% of VA enrollees in 2013 presenting with cirrhosis. Cirrhosis and other liver diseases are among the most common reasons for both hospitalizations and mortality in this population, making liver disease a great challenge for the Veteran Affairs Healthcare System. Associated with liver cirrhosis is the development of HE with liver transplantation being one of the only effective treatment options for decompensated liver cirrhosis, however the presence of cognitive dysfunction in these patients precludes transplantation. Therefore, gaining greater understanding into the molecular pathology contributing to the development of HE would greatly benefit the Veteran Affairs Healthcare System by improving patient care, quality of life, patient morbidity and mortality, and reducing medical expenditures. Current understanding of the pathogenesis of HE is limited to hyperammonemia and neuroinflammation and therapies currently target these key features. However, current therapies for the treatment of HE are not 100% effective and data suggest that other pathological processes may be involved. Without wishing to be bound by theory, the data detailed herein indicate that aberrant bile acid signaling in the brain can contribute to the development of HE by dysregulating cholesterol homeostasis, resulting in increased neurosteroid synthesis. Thus, strategies to restrict aberrant bile acid signaling in the brain, or to prevent the accumulation of cholesterol, may prove to be viable therapeutic targets for the management of HE.

C. METHODS FOR THE TREATMENT OF HEPATIC ENCEPHALOPATHY

In one aspect, disclosed are methods for the treatment of hepatic encephalopathy in a subject diagnosed with a need for treatment for hepatic encephalopathy, the method comprising administering to the subject a therapeutically effective amount of a cholesterol reducing agent.

Hepatic encephalopathy is a serious neuropsychiatric complication of both acute liver failure and chronic liver diseases with the potential to affect health-related quality of life, clinical management strategies, priority for liver transplantation, and patient survival. Associated with the neuropsychiatric decline observed in hepatic encephalopathy are increased cerebral edema, increased intracranial pressure, and brain herniation. Therapies designed to detoxify the blood are often successful in alleviating the symptoms of low grade hepatic encephalopathy. However, the treatment options for patients with more severe hepatic encephalopathy are limited, with liver transplantation being one of the only options that significantly enhances the chances of survival for these patients. Thus, there is significant need for the development of therapeutic strategies to help with survival of patients with severe hepatic encephalopathy.

During acute and chronic liver failure, the enterohepatic circulation becomes disrupted leading to bile acid accumulation in the blood stream. Previous research has shown that increased serum bile acids induce permeability of the blood-brain barrier and can contribute to the development of hepatic encephalopathy (McMillin, M. et al. (2016) *Am. J. Pathol.* 186: 312-323; McMillin, M. et al. (2015) *Mol. Endocrinol.* 29: 1720-1730; Quinn, M. et al. (2014) *Dig. Liver Dis.* 46: 527-534). It was also recently demonstrated that a downstream consequence of this aberrant bile acid signaling is an increased accumulation of cholesterol in the brain (DeMorrow et al., unpublished observation). The brain contains a disproportionately large amount of the body's cholesterol (approx. 25%), which plays a crucial role in normal brain function. Regulation of the cholesterol content in the brain is independent of the rest of the body. Further, increased brain cholesterol has previously been observed in a number of other disoreders (e.g., Neimann Pick's Type C disease and Cerebrotendinous Xanthomatosis).

Cholesterol reducing agents, as disclosed herein, are useful for treating or controlling hepatic encephalopathy. Thus, provided is methodology for administering a therapeutically effective amount of a cholesterol reducing agent to a subject. In a further aspect, the method can be a method for treating hepatic encephalopathy.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of hepatic encephalopathy.

The cholesterol reducing agent can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, intrathecal administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of hepatic encephalopathy.

The therapeutically effective amount or dosage of the cholesterol reducing agent can vary within wide limits. Such a dosage is adjusted to the individual requirements in each particular case including the specific cholesterol reducing agent(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In a further aspect, the subject has been diagnosed with a need for treatment of hepatic encephalopathy prior to the administering step.

In a further aspect, the subject is a mammal. In a still further aspect, the mammal is a human.

In a further aspect, the method further comprises the step of identifying a subject in need of treatment of hepatic encephalophy.

In a further aspect, the effective amount is a therapeutically effective amount. In a still further aspect, the effective amount is a prophylactically effective amount.

In a further aspect, the cholesterol reducing agent is selected from a statin and a cyclodextrin.

In a further aspect, the cholesterol reducing agent is a cyclodextrin. In a stil further aspect, the cyclodextrin is selected from an α-cyclodextrin, a β-cyclodextrin, and a γ-cyclodextrin. In yet a further aspect, the cyclodextrin is selected from 2-hydroxypropyl-α-cyclodextrin, 2-hydroxypropyl-β-cyclodextrin, methylated β-cyclodextrin, hydroxyethyl-β-cyclodextrin, sulfobutylether β-cyclodextrin, and 2-hydroxypropyl-γ-cyclodextrin. In an even further aspect, the cyclodextrin is 2-hydroxypropyl-β-cyclodextrin.

In a further aspect, the cholesterol reducing agent is a statin. In a still further aspect, the statin is selected from atorvastatin, fluvastatin, lovastatin, pravastatin, rosuvastatin, and simvastatin.

D. METHODS FOR MODIFYING LXRβ SIGNALING IN A SUBJECT

In one aspect, disclosed are methods for modifying liver X receptor beta (LXRβ) signaling in a subject diagnosed with a need for modification of LXRβ, the method comprising administering to the subject a therapeutically effective amount of a cholesterol reducing agent.

During acute liver failure (ALF), the enterohepatic circulation becomes disrupted leading to bile acid accumulation in the blood stream. Previous research has shown that increased serum bile acids induce permeability of the blood-brain barrier and can contribute to the development of hepatic encephalopathy (HE) following ALF. This occurs via activation of farnesoid X receptor (FXR), which, in turn, upregulates transcription of small heterodimer partner (SHP) in neurons. The events downstream of FXR activation contributing to HE are unknown. However, in the liver FXR activation is known to decrease the expression of liver X receptor beta (LXRβ). Highly expressed in neurons in the brain, LXRβ has a role in regulation of Cyp46A1, an enzyme responsible for converting cholesterol to 24(S)-hydroxycholesterol-the main mechanism of cholesterol clearance in the brain. Thus, without wishing to be bound by theory, it is believed that increased levels of cholesterol in the brain during ALF and HE result from bile acid-mediated activation of the FXR/SHP pathway and LXRβ suppression leading to a dysregulation of cholesterol clearance.

In a further aspect, the subject has been diagnosed with a need for treatment of hepatic encephalopathy prior to the administering step.

In a further aspect, modifying is increasing.

In a further aspect, the cholesterol reducing agent exhibits an increase in LXRβ signaling. In a still further aspect, the cholesterol reducing agent exhibits activation of LXRβ signaling.

In a further aspect, the cholesterol reducing agent exhibits activation of LXRβ signaling with an $EC_{50}$ of less than about 30 μM. In a still further aspect, the cholesterol reducing agent exhibits activation of LXRβ signaling with an $EC_{50}$ of less than about 25 μM. In yet a further aspect, the cholesterol reducing agent exhibits activation of LXRβ signaling with an $EC_{50}$ of less than about 20 μM. In an even further aspect, the cholesterol reducing agent exhibits activation of LXRβ signaling with an $EC_{50}$ of less than about 15 μM. In a still further aspect, the cholesterol reducing agent exhibits activation of LXRβ signaling with an $EC_{50}$ of less than about 10 μM. In yet a further aspect, the cholesterol reducing agent exhibits activation of LXRβ signaling with an $EC_{50}$ of less than about 5 μM. In an even further aspect, the cholesterol reducing agent exhibits activation of LXRβ signaling with an $EC_{50}$ of less than about 1 μM. In a still further aspect, the cholesterol reducing agent exhibits activation of LXRβ signaling with an $EC_{50}$ of less than about 0.5 μM.

In a further aspect, the subject is a mammal. In a still further aspect, the subject is a human.

In a further aspect, the subject has been diagnosed with a need for treatment of hepatic encephalophy prior to the administering step. In a still further aspect, the method further comprises the step of identifying a subject in need of treatment of hepatic encephalophy.

In a further aspect, the subject has been diagnosed with a need for treatment of a disorder associated with LXRβ signaling dysfunction prior to the administering step. In a still further aspect, the method further comprises the step of identifying a subject in need of treatment of a disorder associated with LXRβ signaling dysfunction. In yet a further aspect, the disorder associated with LXRβ signaling dysfunction is hepatic encephalophy.

In a further aspect, the subject has been diagnosed with a need for modifying LXRβ signaling prior to the administering step. In a still further aspect, the subject has been diagnosed with a need for activating LXRβ signaling prior to the administering step.

E. METHODS FOR MODIFYING LXRβ SIGNALING IN AT LEAST ONE CELL

In one aspect, disclosed are methods for modifying liver X receptor beta (LXRβ) signaling in at least one cell, the method comprising contacting the cell with an effective amount of a cholesterol reducing agent.

In a further aspect, modifying is increasing.

In a further aspect, the cell is human. In a still further aspect, the cell has been isolated from a subject prior to the contacting step.

In a further aspect, contacting is via administration to a subject.

F. PHARMACEUTICAL COMPOSITIONS

In one aspect, disclosed are pharmaceutical compositions comprising a cholesterol reducing agent, or a pharmaceutically acceptable salt thereof and a pharmaceutically acceptable carrier.

In various aspects, the cholesterol reducing agent can be administered in pharmaceutical compositions, which are formulated according to the intended method of administration. The cholesterol reducing agent, as described herein, can be formulated in a conventional manner using one or more physiologically acceptable carriers or excipients. For example, a pharmaceutical composition can be formulated for local or systemic administration, e.g., intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory composition can be formulated in various ways, according to the corresponding route of administration. For example, liquid solutions can be made for administration by drops, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the pharmaceutical compositions of this invention can include a pharmaceutically acceptable carrier and a cholesterol reducing agent or a pharmaceutically acceptable salt of the cholesterol reducing agents of the invention. The cholesterol reducing agents of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a cholesterol reducing agent (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat hepatic encephalopathy.

In certain aspects, the disclosed compounds and compositions can be used in the disclosed methods in combination with other therapeutic agents. For example, the disclosed cholesterol reducing agents (e.g., statins) can be used in combination with N acetylcysteine to restore hepatic glutathione. In a further example, the disclosed cholesterol reducing agents (e.g., statins) can be used in combination with S adenosylmethionine to support methionine metabolism. In a further example, the disclosed cholesterol reducing agents (e.g., statins) can be used in combination with hepatoprotective herbal agents (e.g., silymarin, eclipta alba). In a further example, the disclosed cholesterol reducing agents (e.g., statins) can be used in combination with CoQ10 for antioxidant and anti-inflammatory effect.

In a further example, for subjects with Primary biliary cholangitis (PBC), the disclosed cholesterol reducing agents (e.g., statins) can be used in combination with TUDCA, UDCA, and/or Obetacholic acid (OCALIVA®). In a further example, for subjects with Wilson's disease, the disclosed cholesterol reducing agents (e.g., statins) can be used in combination with metal chelators (e.g., Penicillimine). In a further example, for subjects with Hepatitis C, the disclosed cholesterol reducing agents (e.g., statins) can be used in combination with Vitamin D for benefit with respect to fibrosis.

It is understood that the disclosed compositions can be prepared from the disclosed cholesterol reducing agents. It is also understood that the disclosed compositions can be employed in the disclosed methods of using.

G. MANUFACTURE OF A MEDICAMENT

In one aspect, the invention relates to a method for the manufacture of a medicament for treating hepatic encephalopathy in a subject having hepatic encephalopathy, the method comprising combining a therapeutically effective amount of a cholesterol reducing agent with a pharmaceutically acceptable carrier or diluent.

As regards these applications, the present method includes the administration to an animal, particularly a mammal, and more particularly a human, of a therapeutically effective amount of the cholesterol reducing agent effective in the treatment of hepatic encephalopathy. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the cholesterol reducing agent administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a cholesterol reducing agent, or a pharmaceutically acceptable salt, solvate, or polymorph thereof, with a pharmaceutically acceptable carrier or diluent.

H. KITS

In one aspect, disclosed are kits comprising a cholesterol reducing agent and one or more of: (a) at least one agent associated with the treatment of hepatic encephalopathy; (b) at least one agent associated with the treatment of liver failure; (c) at least one liver protective agent; (d) instructions for treating hepatic encephalopathy; (e) instructions for treating liver failure; (0 instructions for administering the cholesterol reducing agent in connection with reducing the risk of liver failure; and (g) instructions for administering the cholesterol reducing agent in connection with protecting a liver.

In a further aspect, at least one compound and at least one agent associated with the treatment of hepatic encephalopathy are co-formulated. In a further aspect, at least one compound and at least one agent associated with the treatment of hepatic encephalopathy are co-packaged.

In a further aspect, the compound and the agent associated with the treatment of hepatic encephalopathy are administered sequentially. In a still further aspect, the compound and the agent associated with the treatment of hepatic encephalopathy are administered simultaneously.

In a further aspect, at least one compound and the at least one agent associated with the treatment of liver failure are co-formulated. In a further aspect, at least one compound and at least one agent associated with the treatment of liver failure are co-packaged.

In a further aspect, the compound and the agent associated with the treatment of liver failure are administered sequentially. In a still further aspect, the compound and the agent associated with the treatment of liver failure are administered simultaneously.

In a further aspect, at least one compound and the at least one liver protective agent are co-formulated. In a further aspect, at least one compound and the at least one liver protective agent are co-packaged.

In a further aspect, the compound and the liver protective agent are administered sequentially. In a still further aspect, the compound and the liver protective agent are administered simultaneously.

In a further aspect, the agent associated with the treatment of hepatic encephalopathy is lactulose. In a still further aspect, the agent associated with the treatment of hepatic encephalopathy is an antibiotic. In yet a further aspect, the antibiotic is selected from neomycin and rifaximin.

In a further aspect, the agent associated with the treatment of liver failure is acetylcysteine. In a still further aspect, the agent associated with the treatment of liver failure is selected from a corticosteroid and an interferon. In yet a further aspect, the corticosteroid is selected from cortisol, cortisone, prednisone, prednisolone, methylprednisolone, triamcinolone, betamethasone, and dexamethasone. In an even further aspect, the interferon is selected from peginterferon and interferon α-2B.

In a further aspect, the liver protective agent is selected from caffeic acid phenylester, milk thistle, turmeric, and bupleurum.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of use.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

I. EXAMPLES

Herein, it has been demonstrated, using a mouse model of hepatic encephalopathy, that agents aimed at lowering brain cholesterol are useful in alleviating the neurological impairment associated with liver failure (i.e., hepatic encephalopathy). Specifically, mice were infused with 2-hydroxypropyl-cyclodextrin into the cerebroventricular space prior to the induction of liver damage. Without wishing to be bound by theory, this treatment dramatically delayed the onset of neurological complications and increased the time it took the mice to reach hepatic coma. Thus, agents that lower brain cholesterol including, but not limited to, cyclodextrins and statins, may be useful in the treatment of patients with hepatic encephalopathy.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Experimentals a. Materials

All chemicals were purchased from MilliporeSigma (Burlington, Mass.) unless otherwise noted and were of the highest grade available. Total Cholesterol and Cholesteryl Ester Colorimetric/Fluorometric Assay Kit was purchased from BioVision Inc (Milpitas, Calif.). Nile Red was purchased from Tokyo Chemical Industry (Tokyo, Japan). The Cyp46A1 antibody was purchased from GeneTex (Irvine, Calif.). The glycderaldehyde-3 phosphate dehydrogenase (GAPDH) antibody was purchased from GeneTex (Irvine, Calif.). The primer for Cyp46A1 (Catalog no: PPM03965A) and GAPDH (Catalog no: PPM02946E) were purchased from Qiagen, SABiosciences (Frederick, Md.). FXR Vivo-Morpholino sequences (FXR Morpholino;
 5'-CTGAAACTGCATCACCATCCTTAGC-3', SEQ ID NO: 1), FXR Mismatch Vivo-Morpholino sequences (FXR Mismatch;
 5'-CTCAAAGTGGATCACCATCGTTACC-3', SEQ ID NO: 2)

and Endo-Porter were purchased from Gene Tools (Philomath, Oreg.). Guggulsterone was purchased from Tocris (Minneapolis, Minn.). Hematoxylin was purchased from Vector Laboratories (Burlingame, Calif.). Eosin was purchased from MilliporeSigma. Liver enzyme blood chemistry assays were purchased from IDEXX Laboratories, Inc (Westbrook, Mass.).

b. Mouse Model of Acute Liver Failure

In vivo experiments were performed using male C57Bl/6 mice (25-30 g; Charles River Laboratories, Wilmington Mass., USA) or Cyp7A1−/− mice bred on a C57Bl/6 background (Kind gift from Dr. Sandra Erickson, University of California, San Francisco, Calif. (Erickson, S. K. et al. (2003) *J. Lipid Res.* 44(5): 1001-9)). All animal experiments were approved by the Baylor Scott & White Research Institute IACUC committee and were performed in accordance with the Animal Welfare Act and the Guide for the Care and Use of Laboratory Animals.

Acute liver failure and HE was induced using the hepatotoxin azoxymethane (AOM) as previously described (McMillian, M. et al. (2016) *Am. J. Pathol.* 186(2): 312-23; McMillin, M. et al. *Front Cell Neurosci.* (2017) 11: 191; McMillin, M. et al. (2014) *Journal of Hepatology* 6(1): 1260-6; McMillin, M. et al. (2016) *J. Neuroinflammation* 13(1): 198). Briefly, C57Bl/6 or Cyp7A1−/− mice were injected with AOM (100 mg/kg ip) and placed on heating pads set to 37° C. to ensure normothermia. To reduce serum and cortical bile acid levels, C57Bl/6 mice were fed a diet supplemented with 2% cholestyramine (Dyets Inc.; Bethelhem, Pa.), or the control diet AIN-93G, for 3 days prior to the injection of AOM. In parallel, C57B/6 mice underwent surgery to implant Alzet brain infusion cannulas coupled to subcutaneous implanted minipumps (Alzet; Cupertino, Calif., USA) to directly infuse FXR Morpholino or FXR Mismatch (1 mg/kg) made up in a 10 µM Endo-Porter solution to knock down FXR expression in the brain, which effectively knocked down the expression of FXR in neurons located adjacent to the injection site shown and characterized in previous studies (McMillin, M. et al. (2016) *Am. J Pathol.* 186(2): 312-23). This same approach was used to infuse 2-hydroxypropyl-β-cyclodextrin (2-HβC; 6 mg/kg/day, MilliporeSigma) to inhibit cholesterol accumulation. The infusion cannulas were implanted using the co-ordinates AP −0.34, ML −1.0, DV −2.0. This surgery was performed 3 days prior to the injection of AOM to allow the mice to recover prior to the onset of acute liver failure to minimize mortality.

Starting at 12 hr after injection, mice were monitored at least every 2 hours for body temperature, weight and neurological score as previously described (McMillin, M. et al. *Front Cell Neurosci.* (2017) 11: 191; McMillin, M. et al. (2016) *J. Neuroinflammation* 13(1): 198). The neurological score was assessed by an investigator blind to the treatment groups and is a summation of the scores given for the following parameters: pinna reflex, corneal reflex, tail flexion, escape response, righting reflex and gait. Each parameter was assigned a score between 2 (normal) and 0 (absence of reflexes and presence of severe ataxia), and summed to give a neurological score out of 12. At approximately 16 hours after AOM injection, the gait of these experimental mice was further examined using ventral plane imaging technology (DigiGait, Mouse Specifics Inc, Framingham, Mass., USA) which images the underside of animals walking atop a motorized, transparent treadmill belt thereby generating digital paw prints. These paw prints were analyzed using DigiGait Analysis and Imager software (Mouse Specifics Inc, Framingham, Mass., USA) and measures of neuromuscular function were quantified, including the paw angle in fore- and hind limbs (to measure the degree of external rotation), gait symmetry (ratio of forelimb stepping frequency to hindlimb stepping frequency) and the ataxia coefficient for fore and hind limbs (calculated by [maximum stride length−minimum stride length]/average stride length).

Tissue was collected prior to the onset of neurological symptoms (preneurological), when minor ataxia and weakened reflexes were present (minor neurological), when major ataxia and deficits in reflexes were evident (major neurological) and at coma, as defined by a loss of righting and corneal reflexes. In experiments involving Cyp7A1−/− mice, cholestyramine-supplemented mice or 2-HβC-infused mice only the coma time point was investigated.

c. Assessment of Liver Damage and Function

Liver damage was assessed by H&E staining according to previously published protocols (McMillin, M. et al. (2017) *Front Cell Neurosci.* 11: 191). Paraffin-embedded livers were cut into 4 µm sections and mounted onto positively-charged slides (VWR, Radnor, Pa.). Slides were deparaffinized and stained with Hematoxylin QS (Vector Laboratories, Burlingame, Calif.) for one minute followed by staining for one minute with eosin Y (Amresco, Solon, Ohio) and rinsed in 95% ethanol. The slides were then dipped into 100% ethanol and subsequently through 2 xylene washes. Coverslips were mounted onto the slides using CytoSeal XYL mounting media (ThermoFisher). The slides were viewed and imaged using an Olympus BX40 microscope with an Olympus DP25 imaging system (Center Valley, Pa.).

Liver function was assessed by measuring plasma alanine aminotransferase (ALT) and aspartate aminotransferase (AST) using the IDEXX Catalyst One machine from IDEXX Laboratories, Inc (Westbrook, Mass.).

d. In Vitro Primary Neuronal Culture

Primary cortical neurons were isolated and cultured using methodology previously described (McMillin, M. et al. (2014) *Journal of hepatology* 61(6): 1260-6). Primary neurons were isolated from P1 mouse pups. Mice were decapitated and whole brains were removed. The cortex was isolated and meninges and dura were removed. Cortical tissue was mechanically disrupted and filtered through a 100 µm filter. Neurons were pelleted by centrifugation at 1400 g. Neurons were suspended in media and plated on 12-well plates with 750,000 cells per well. After 24 hours, cells were washed and media was replaced and supplemented with 2% B27 growth supplement. Cells were cultured for 10-12 days and subsequently treated with deoxycholic acid (DCA) (10 µM) in the presence or absence of the FXR antagonist guggulsterone (10 µM) for 24 hr. At this point, cells were lysed and used for immunoblot or RTPCR analyses.

e. Assessment of Bile Acid Content in the Brain

The bile acid content of cortex tissue was determined using methodology previously employed for other studies (McMillin, M. et al. (2016) *Am. J. Pathol.* 186(2): 312-23). When AOM-treated mice progressed to coma, they were euthanized and transcardially perfused with ice-cold saline to remove the blood from the brain. Cortex homogenates were prepared by calculating wet weight of brain tissue with subsequent homogenization in 100 mg/ml in ultrapure water using a Miltenyi Biotec gentleMACS™ Dissociator (San Diego, Calif.). Homogenates were spun down for 5 min at 16,100 g and supernatants were collected. Total bile acid content was assessed in homogenates of the frontal cortex following the manufacturer's instructions (IDEXX, Westbrook, Me.). Data are reported as nmol of bile acid per mg of cortex tissue protein for each respective analysis.

f. Measurement of Brain Cholesterol

Total, free and esterified cholesterol was assessed in brain homogenates using a BioVision Total Cholesterol and Cholesteryl Ester Assay Kit following the instructions from the vendor. The subcellular location of cholesterol was assessed using Nile Red staining (for intracellular cholesterol (Pol, A. et al. (2001) *J. Cell Biol.* 152(5): 1057-70)) and Filipin III staining (for membrane bound cholesterol (Vanier and Latour (2015) *Methods Cell Biol.* 126: 357-75)). Briefly, mice were transcardially perfused with ice-cold phosphate buffered saline (PBS), followed by 4% paraformaldehyde (PFA) in PBS. Whole brains were rapidly removed and post-fixed in PFA overnight at 4° C. Brains were cryoprotected in 30% sucrose (in PBS) and embedded in OCT compound. Thirty micrometer sections were cut through the frontal cortex region; sections were rinsed in PBS and further fixed in 4% PFA for 10 minutes at room temperature. Free-floating sections were incubated with Filipin III (0.5 µg/mL in 10% bovine serum albumin/PBS) for 2 hours at room temperature, or with Nile Red (10 µg/mL in PBS) for 30 minutes at room temperature. Sections were washed in PBS, mounted onto microscope slides and imaged using a Bio-Rad Zoe™ Fluorescent Cell Imager (Hercules, Calif.). Field images were quantified for percent-positive area of Nile Red or Filipin III staining using ImageJ software (National Institutes of Health, Bethesda, Md.).

g. Expression of CYP46A1

RNA was extracted from tissue or primary neurons using an RNeasy Mini Kit (Qiagen, Germantown, Md.) according to the manufacturer's instructions. Synthesis of cDNA was accomplished using a Bio-Rad iScript™ cDNA Synthesis Kit. RT-PCR was performed as previously described (Frampton, G. et al. (2012) *Gut* 61(2): 268-77) using commercially available primers designed against mouse Cyp46A1 and glyceraldehyde 3-phosphate dehydrogenase (GAPDH) (SABioscience, Frederick, Md.). A ΔΔCT analysis was performed using vehicle-treated tissue or untreated primary neurons as controls for subsequent experiments (DeMorrow, S. et al. (2008) *American Journal of Physiology Gastrointestinal and Liver Physiology* 295(6): G1150-8; Livak and Schmittgen (2001) *Methods* 25(4): 402-8).

Cortex tissue from all treatment groups was homogenized using a Miltenyi Biotec gentleMACS™ Dissociator and total protein was quantified using a ThermoFisher Pierce™ BCA Protein Assay kit. SDS-PAGE gels (10% v/v) were loaded with 10-20 µg of protein diluted in laemmli buffer per each tissue sample. Specific antibodies against Cyp46A1 and β-actin were used. All imaging was performed on an Odyssey 9120 Infrared Imaging System (LI-COR, Lincoln, Nebr.). Data are expressed as fold change in fluorescent band intensity of target antibody divided by β-actin or GAPDH, which are used as loading controls. The values of vehicle or control groups were used as a baseline and set to a relative protein expression value of 1. Band intensity quantifications were performed using ImageJ software.

h. Statistics

All statistical analyses were performed using Graphpad Prism software (Graphpad Software, La Jolla, Calif.). For data that passed normality tests, significance was established using the Student's t-test when differences between two groups were analyzed, and analysis of variance when differences between three or more groups were compared followed by the appropriate post hoc test. If tests for normality failed, two groups were compared with a Mann-Whitney U test or a Kruskal-Wallis ranked analysis when more than two groups were analyzed. Results were expressed as mean±SEM. Differences were considered significant for $p<0.05$.

2. Preliminary Studies a. Models of Type C HE

Two different rodent models of liver cirrhosis that result in the development of HE were used. The first is the bile duct ligation (BDL) model in rats which is a recommended model by a working group of the International Society of Hepatic Encephalopathy and Nitrogen Metabolism. Approximately six weeks after BDL surgery, rats develop liver failure, jaundice, portal hypertension, portalsystemic shunting, hyperammonemia, and the development of moderate encephalopathy. The second model is an accepted model of cirrhosis in mice, involving the chronic administration of the hepatotoxin carbon tetrachloride (CCl4) and has been previously used in many HE studies, although the encephalopathy is not as well-characterized.

In order to validate the use of these models, a number of indices of neurobehavioral and neuromuscular tests were used to characterize these rodents. The Rotarod is a performance test that is a measure of balance and motor co-ordination in which rodents are placed on a rotating rod with increasing speed. The endurance (time on the Rotarod) and distance traveled by each experimental rodent was measured. Both BDL rats and CCl4 mice had a significantly decreased endurance and distance traveled on the apparatus compared to controls (FIG. 1A) suggesting an impairment in motor co-ordination, which is consistent with previously published models of hepatic encephalopathy. Secondly, the locomotor activity of these experimental rodents was assessed using an open field test. FIG. 1B shows representative tracings of the locomotor activity of BDL rats and CCl4 mice over 1 minute, both of which clearly had reduced mobility and locomotor activity when compared to their corresponding control animals. These recordings can be used to measure parameters such as distance traveled and time spent in inner zone versus the outer periphery as a measure of thigmotaxis, or anxiety-related behavior. Furthermore, both BDL rats and CCl4 mice had reduced grip strength and a more significant degree of ataxia (described herein and data not shown), consistent with previous studies of HE. Other key features of HE were observed in these models, including hyperammonemia (data not shown) and neuroinflammation in the frontal cortex (FIG. 1C). Using Iba1 immunoreactivity as a microglia marker, the prevailing microglia phenotype was ramified (small cell body and long processes) in control rodents and amoeboid (larger cell body with retracted processes) in the rodents with HE (FIG. 1C). Furthermore, there was a concomitant increase in TNF-α expression in the frontal cortex (FIG. 1D) consistent with previous models of HE. Without wishing to be bound by theory, these data indicate that both the BDL model in rats and the CCl4 model in mice display robust and consistent features of HE and are suitable for the proposed studies as further detailed herein.

Figure 1B:
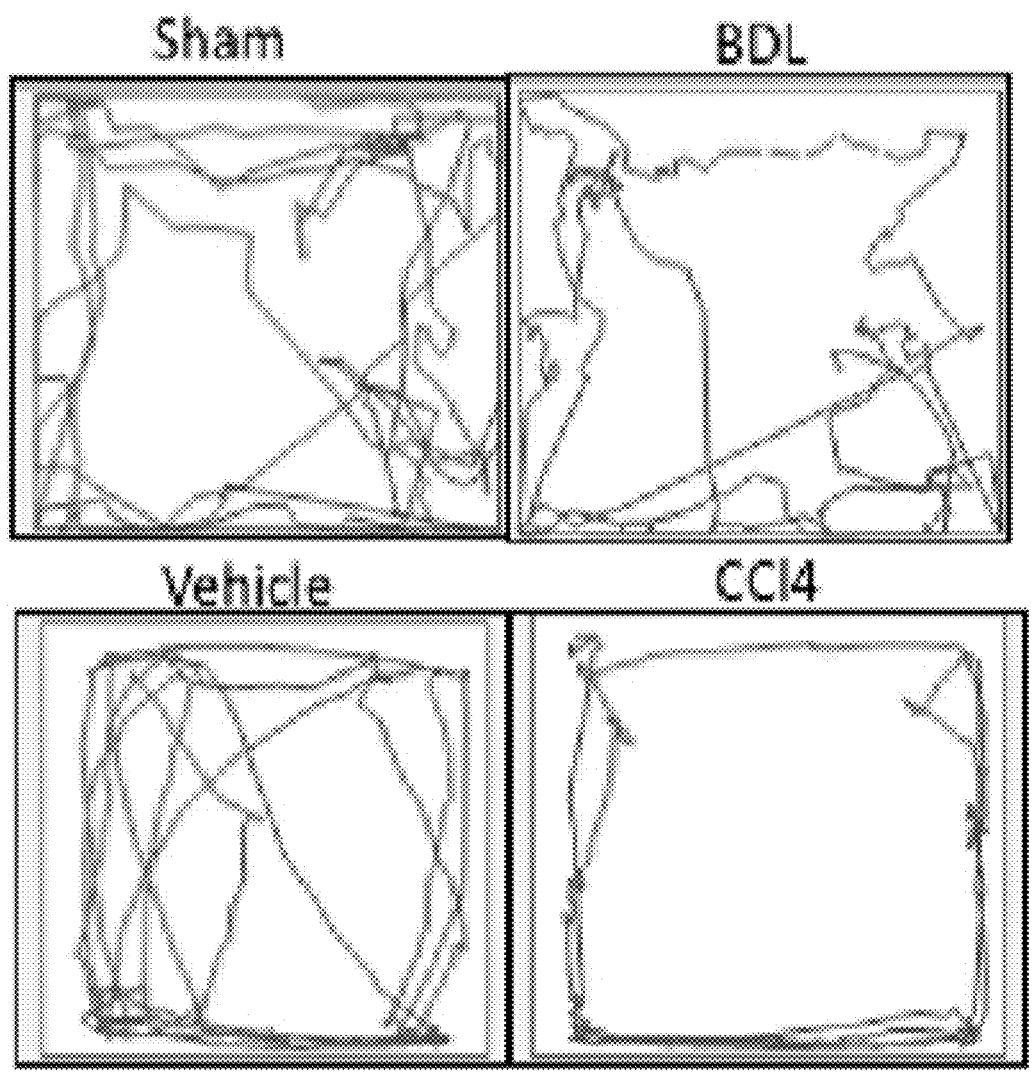
Figure 1C:
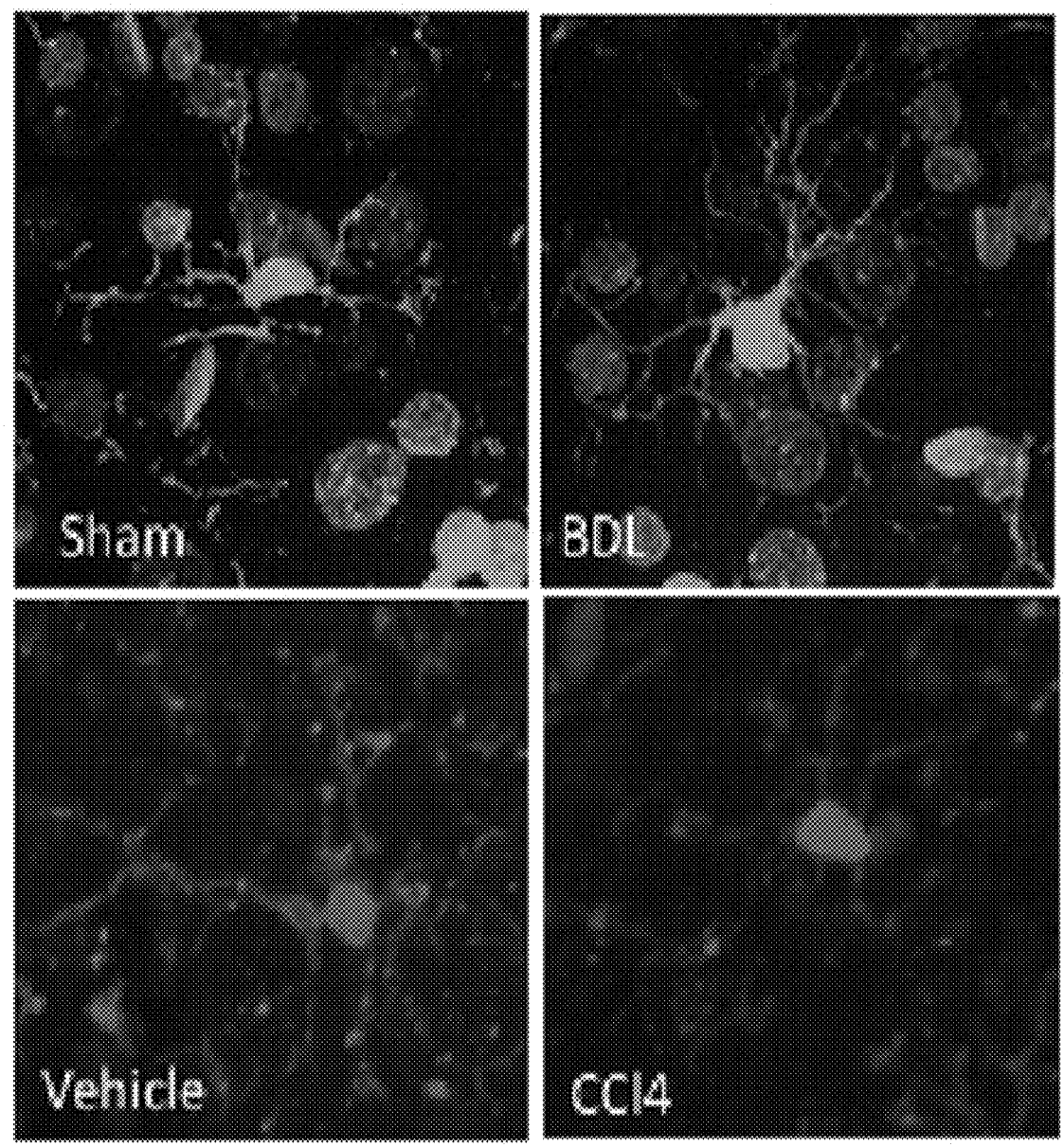
Figure 1D:
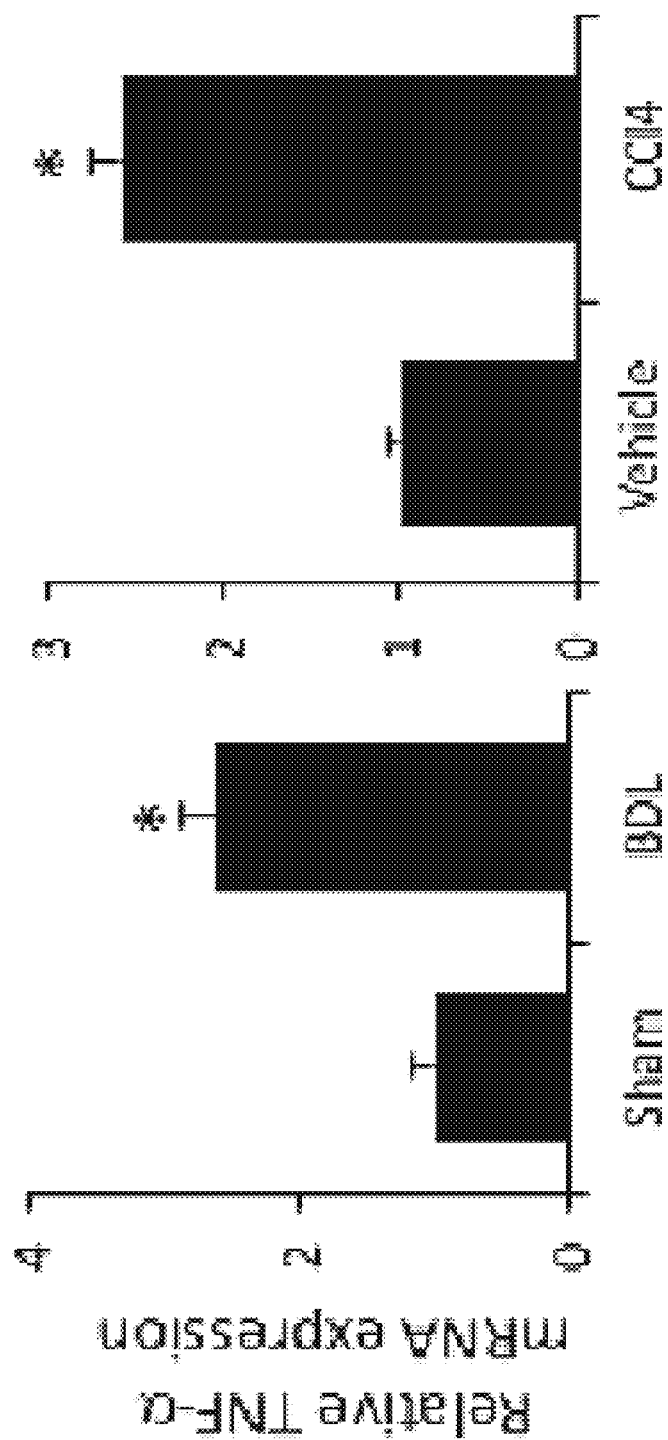

Referring to FIG. 1A, balance and motor co-ordination were assessed using a Rotarod apparatus. Referring to FIG. 1B, locomotion was assessed by an open field test. Referring to FIG. 1C, Iba1 immunostaining was performed to assess microglia activation in the frontal cortex. Sections were counterstained with DAPI. Referring to FIG. 1D, the expression of proinflammatory cytokine TNF-α in the frontal cortex of Type C HE rodents was assessed by qPCR. Data are avg±SEM, *p<0.05 vs sham or vehicle.

b. The Bile Acid Content in Brain Tissue is Increased in Models of Type C HE

Figure 2A:
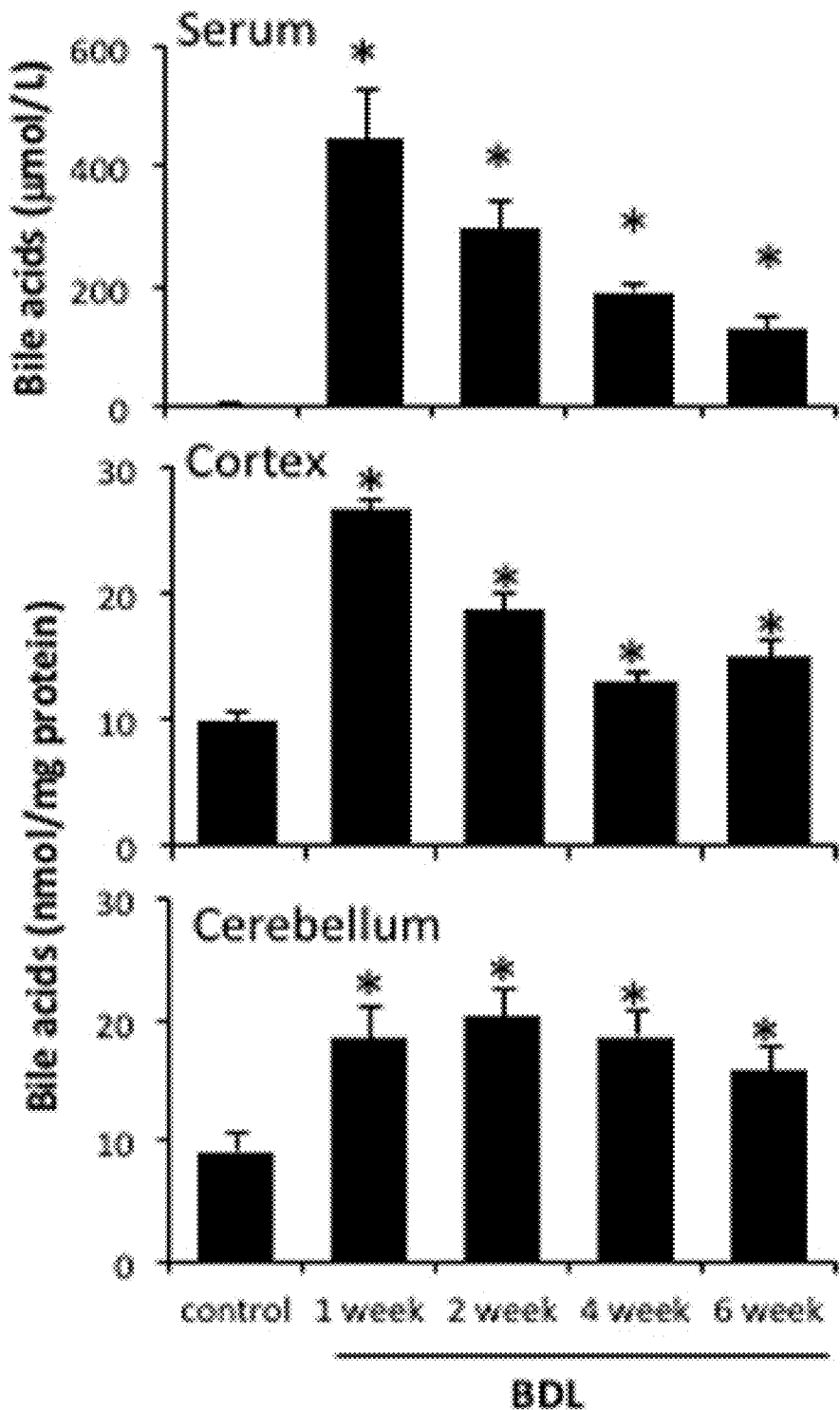
FIG. 2A-D show representative data demonstrating that bile acid content in brain tissue is increased in models of Type C HE.
Figure 2B:
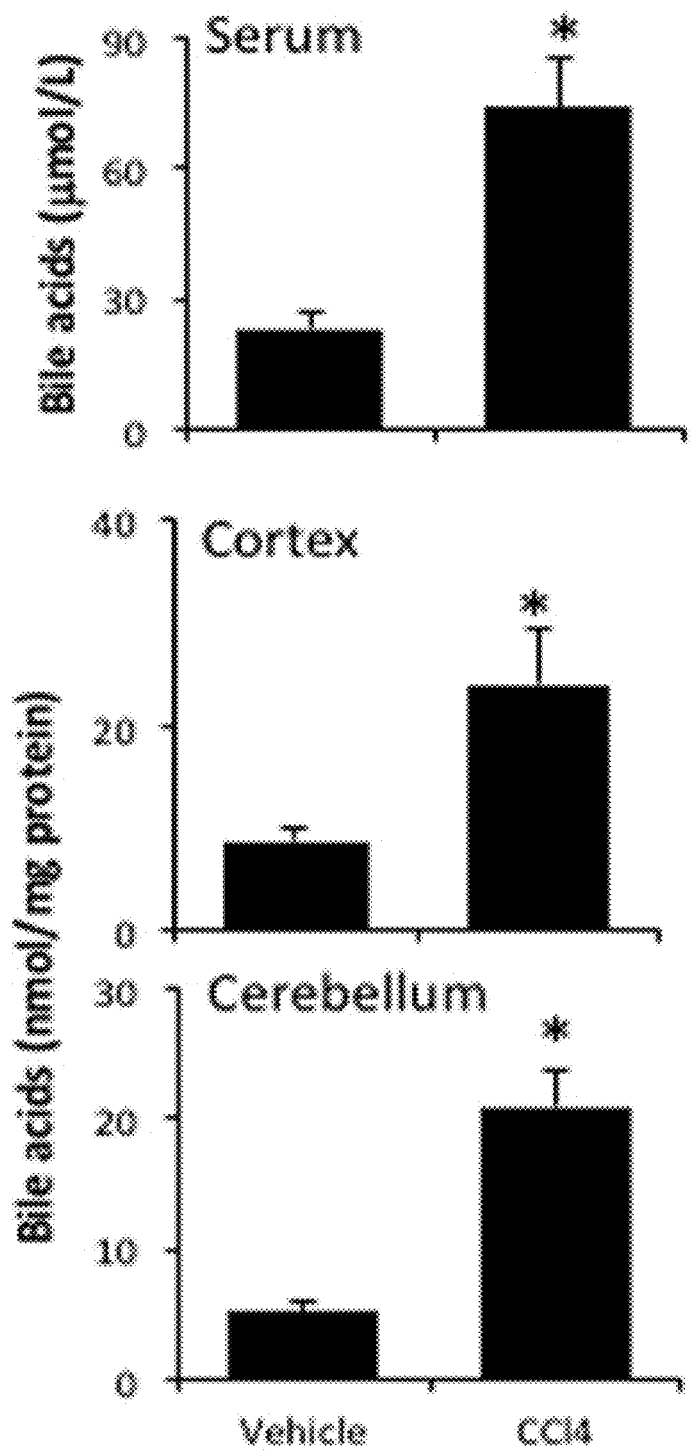
Figure 2C:
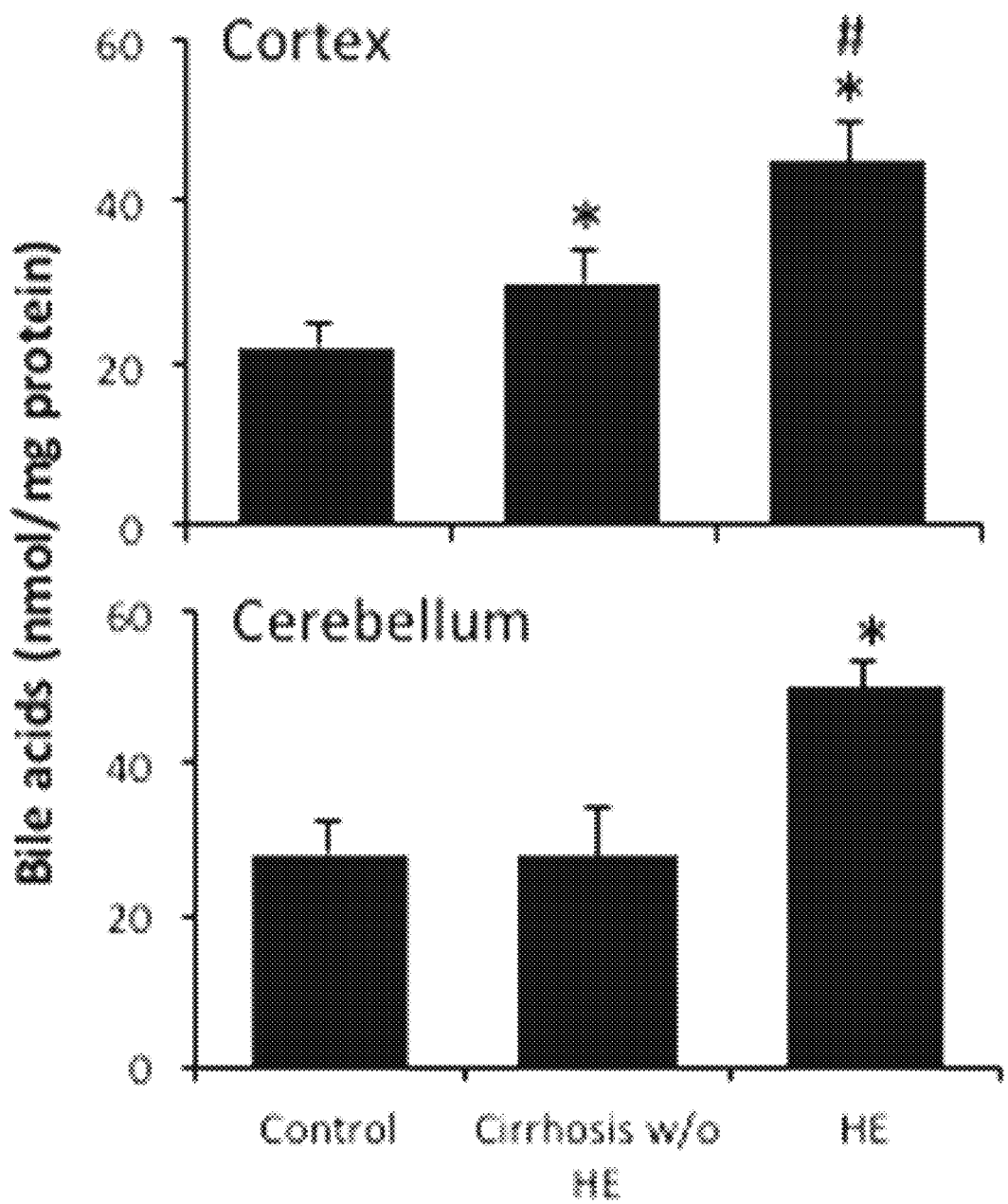
Figure 2D:
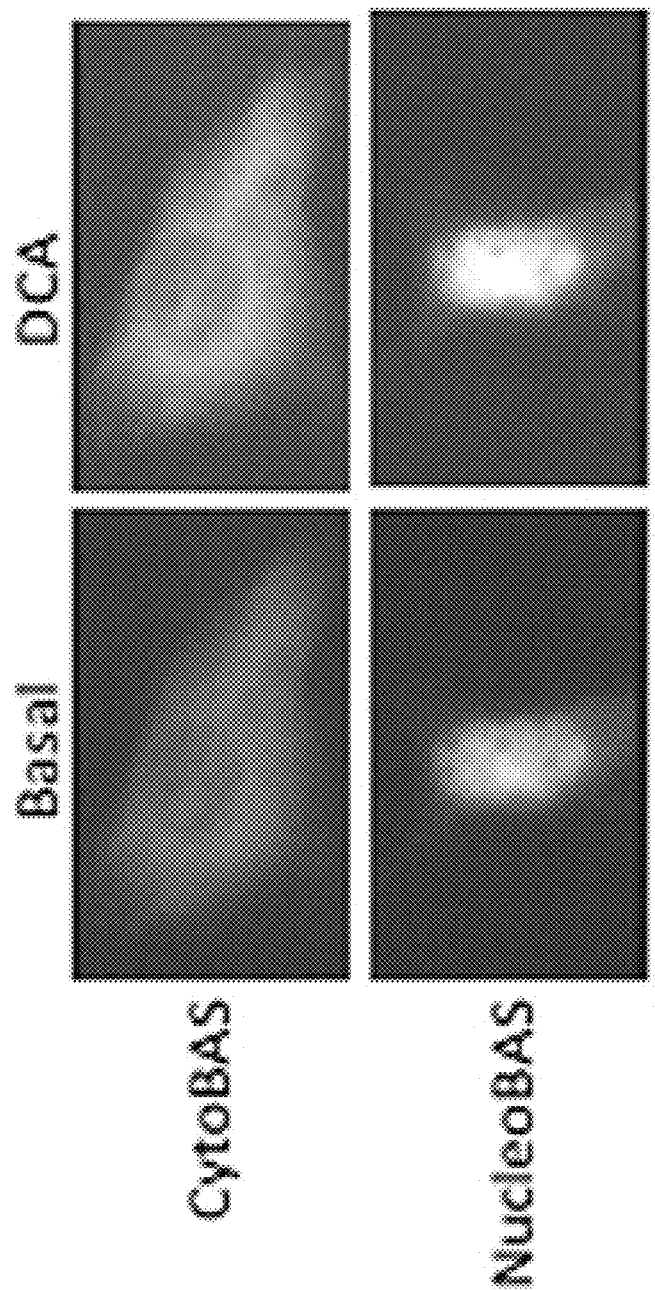

As detailed above, bile acids are increased in the serum in response to liver injury of varying types. Indeed, in both BDL rats and CCl4 mice, serum bile acid levels were increased when compared to controls (FIG. 2A and FIG. 2B). It has been previously demonstrated that bile acids can be detected in the frontal cortex and that the total bile acid levels increase in a rodent model of acute liver failure. Similarly, total bile acid content is increased in the frontal cortex and cerebellum in both rodent models of HE (FIG. 2A), as well as in frozen autopsy samples of the frontal cortex from patients who died of cirrhosis with HE, compared to cirrhotics without HE and non-liver impaired age- and gender-matched controls (FIG. 2C). In a preliminary screen, state-of-the-art, ultra-performance liquid chromatography ion mobility mass spectrometry (UPLCIM-MS) was used to identify which individual bile acid species are increased in the brain during Type C HE. Among the few bile acids tested, the amounts of TCA, lithocholic acid (LCA), and GCA, as well as a peak that could be either DCA or chenodeoxycholic acid (CDCA; resolution of this peak is underway), could be detected in the frontal cortex of BDL rats that were not detected in the sham rats (data not shown). Interestingly, cholic acid could be detected in sham and BDL cortex to a similar degree (data not shown). It has been previously demonstrated that neurons can take up the fluorescent bile acid derivative CLF in vitro via an ASBT-mediated mechanism and in support of these findings, using FRET analysis, DCA treatment resulted in an increased fluorescence intensity of cells transfected with the cytoplasmic bile acid sensor (CytoBAS)48 as well as the nuclear bile acid sensor (NucleoBAS48; FIG. 2D), indicating an efficient uptake of bile acids to both the cytoplasm and nucleus in neurons.

Referring to FIG. 2A-C, total bile acid concentrations were measured in the serum and cortical or cerebellar tissue lysates from BDL rats (FIG. 2A), CCl4-treated mice (FIG. 2B), and human autopsy tissue from patients who died with HE, cirrhosis without HE and age- and gender-matched controls (FIG. 2C). Data are avg±SEM, *p<0.05 vs sham or vehicle.

Referring to FIG. 2D, neurons were transfected with a cytoplasmic bile acid FRET sensor or a nuclear bile acid FRET sensor and an increase in fluorescence intensity in each cell was observed after treatment with DCA.

c. Altered Neuronal Expression of Bile Acid Signaling Machinery During Type C HE It was previously demonstrated that ASBT is expressed in neurons and is upregulated in a number of neurological disorders including Type A HE. The expression of ASBT is increased in the frontal cortex of BDL rats (FIG. 3A) and CCl4 mice (FIG. 3B and FIG. 3D) compared to the corresponding controls. Similarly, ASBT expression was increased in frozen autopsy samples of the frontal cortex from patients who died of cirrhosis with HE, compared to cirrhotics without HE and non-liver impaired age- and gender-matched controls (FIG. 3C). Similar to published studies, ASBT immunoreactivity was predominantly located in neurons in mice and in human samples (FIG. 3D and FIG. 3E). Once inside the cell, bile acids can activate FXR, the expression of which was increased in the cortex of Type A HE. Similar to acute liver failure, the expression of FXR was increased in the cortex of our rodent models of Type C HE (FIG. 4A, FIG. 4B, and FIG. 4G), compared to the corresponding controls and in frozen autopsy samples from patients who died of cirrhosis with HE, compared to cirrhotics without HE and non-liver impaired age- and gender-matched controls (FIG. 4C). FXR immunoreactivity was predominantly located in neurons in mice and in human samples (FIG. 4G and FIG. 4H), which is similar to published studies. To ensure that the increase in FXR expression is functional in these models, the expression of SHP, the downstream target of FXR activation was assessed, and indeed, there was a parallel in increase in SHP expression our rodent models of Type C HE (FIG. 4D and FIG. 4E) compared to the corresponding controls, as well as in HE patients, compared to cirrhotics without HE and non-liver impaired age- and gender-matched controls (FIG. 4F).

Figure 3B:
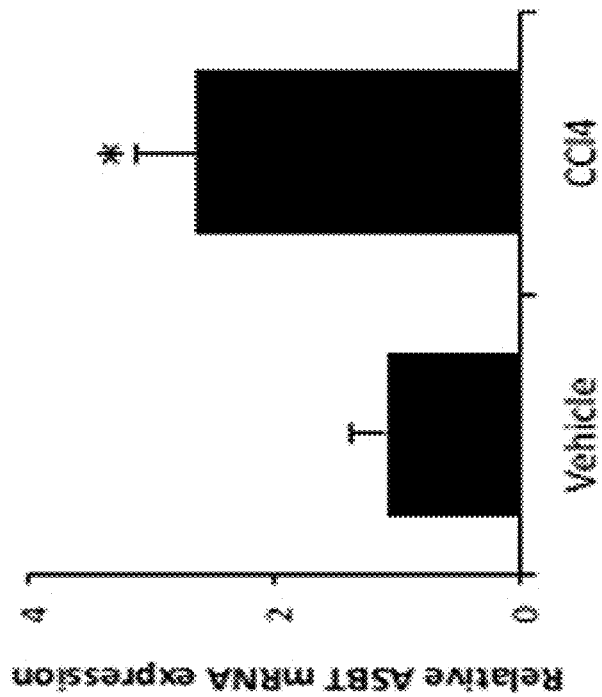
FIG. 3A-E show representative data relating to the expression of ASBT and ASBT immunoreactivity.
Figure 3A:
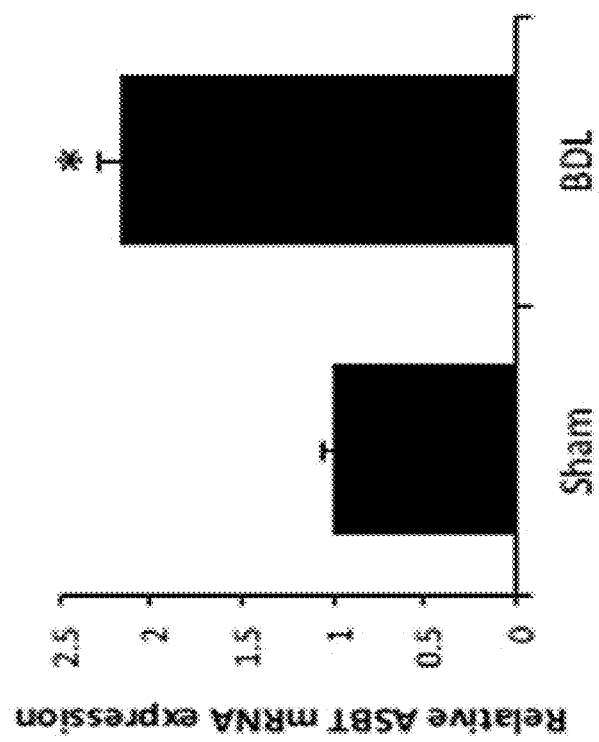
Figure 3D:
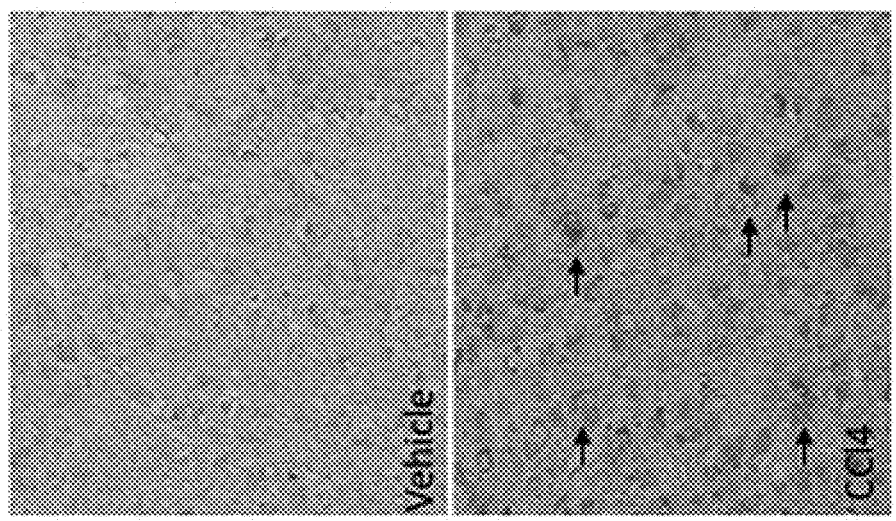
Figure 3C:
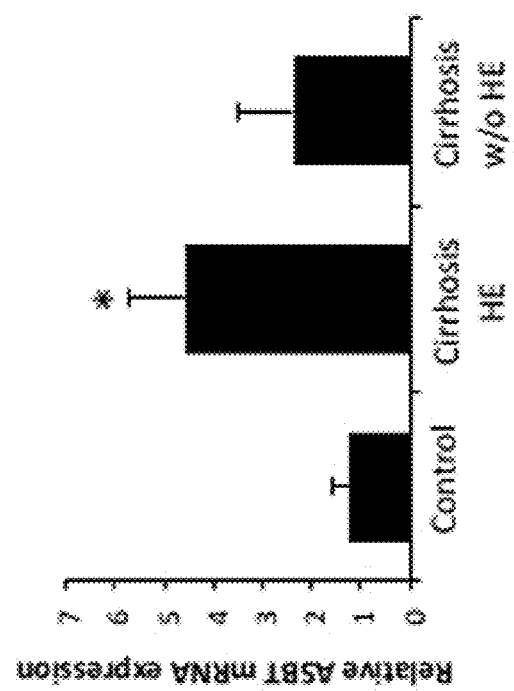
Figure 3E:
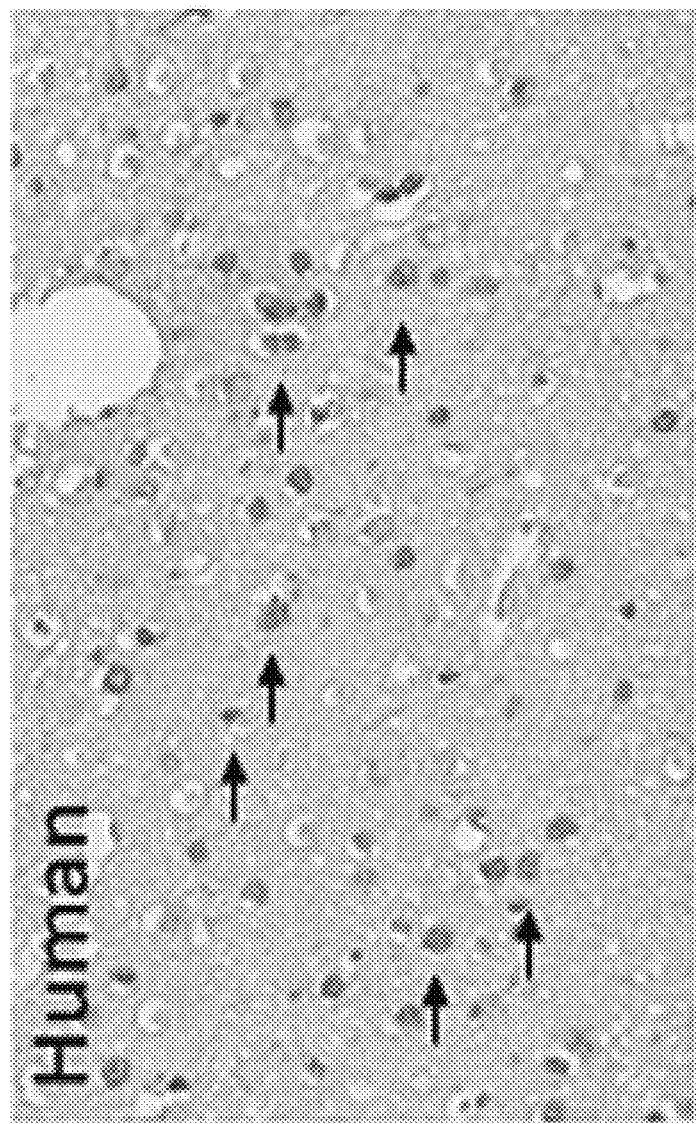
Figure 4B:
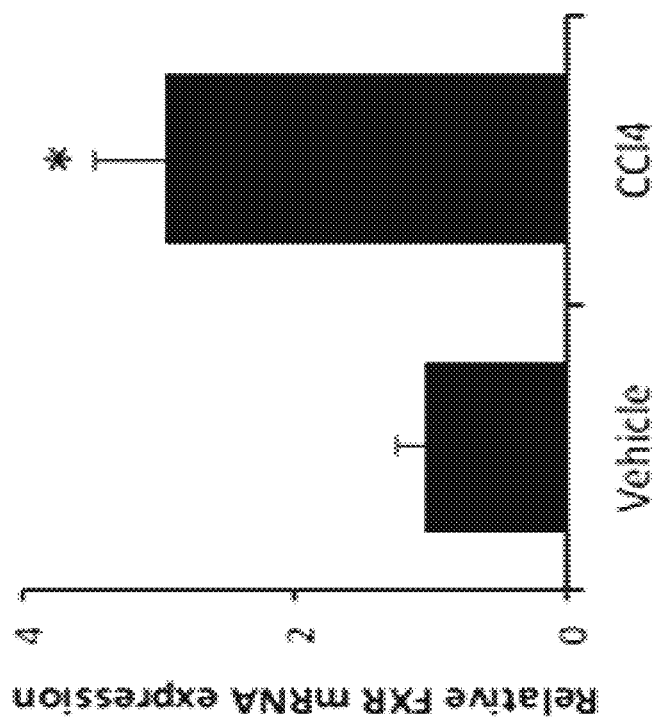
FIG. 4A-H show representative data relating to the expression of FXR and FXR immunoreactivity.
Figure 4A:
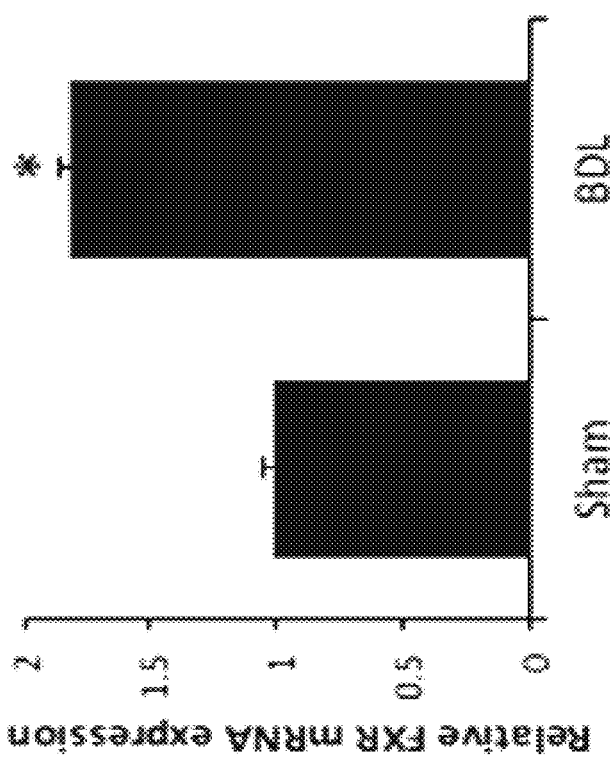
Figure 4D:
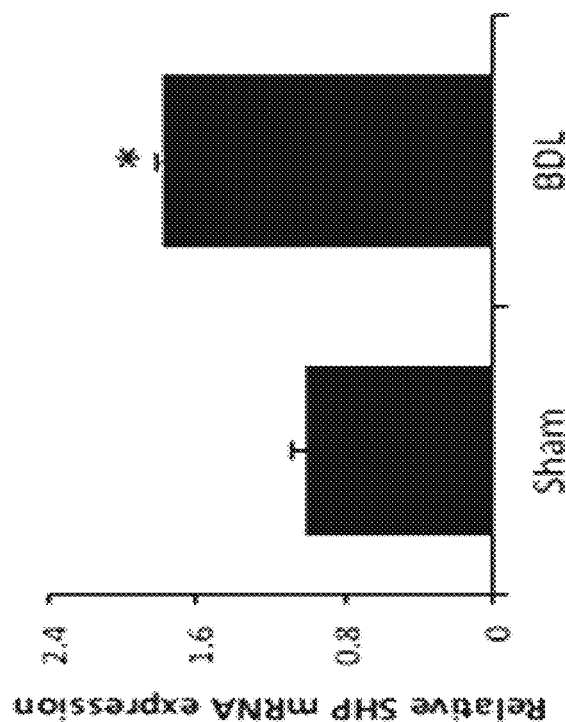
Figure 4C:
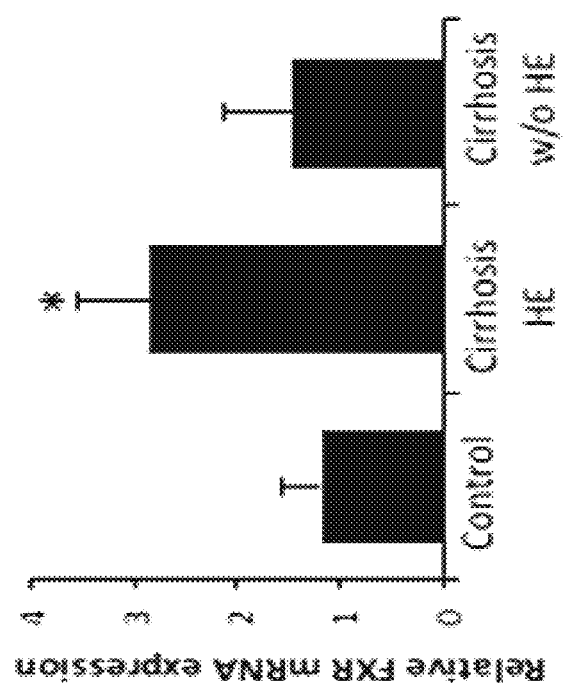

Referring to FIG. 3A-C, the expression of ASBT was assessed in cortical samples from BDL rats (FIG. 3A), CCl4-treated mice (FIG. 3B), and human autopsy tissue from patients who died with HE, cirrhosis without HE, and age- and gender-matched controls (FIG. 3C). Data are avg±SEM, *p<0.05 vs sham or vehicle.

Referring to FIG. 3D and FIG. 3E, ASBT immunoreactivity was also assessed in the cortex from CCl4-treated mice (FIG. 3D) and in human tissue (FIG. 3E) by immunohistochemistry.

Figure 4F:
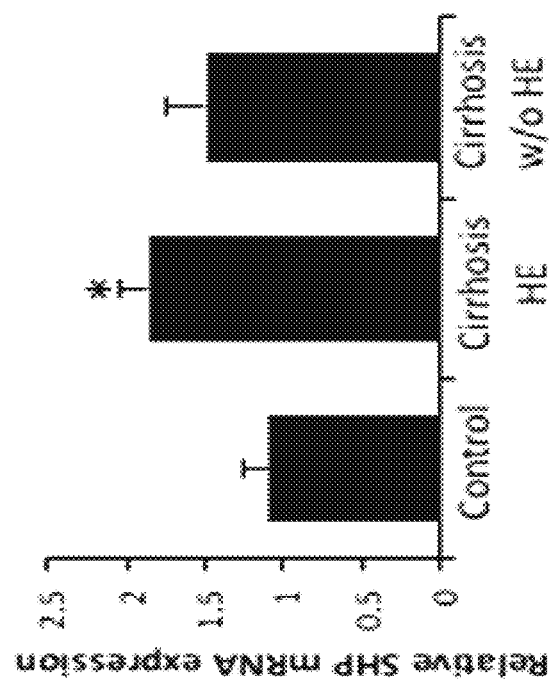
Figure 4E:
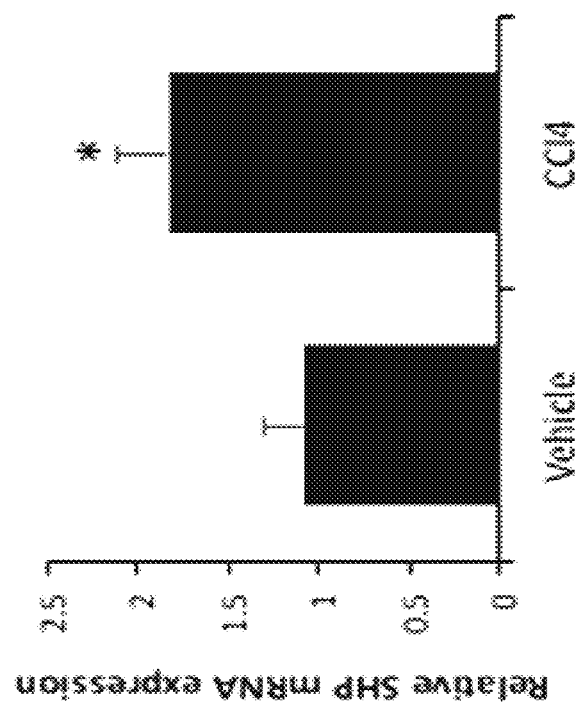

Referring to FIG. 4A-F, the expression of FXR (FIG. 4A-C) and SHP (FIG. 4D-F) were assessed in cortical samples from BDL rats (FIG. 4A and FIG. 4D), CCl4-treated mice (FIG. 4B and FIG. 4E) and human autopsy tissue from patients who died with HE, cirrhosis without HE, and age- and gender-matched controls (FIG. 4C and FIG. 4F). Data are avg±SEM, *p<0.05 vs sham or vehicle.

Figure 4H:
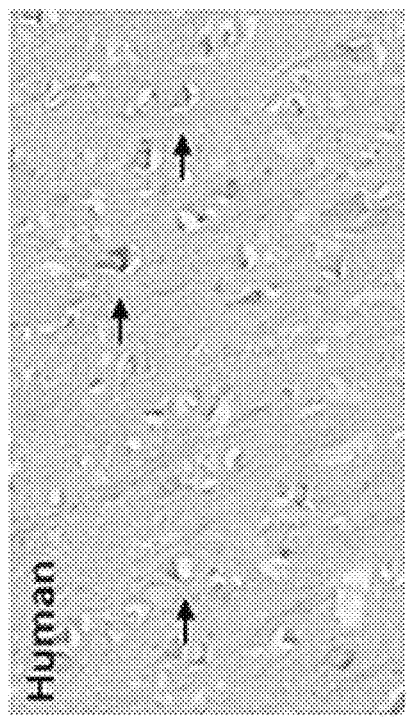
Figure 4G:
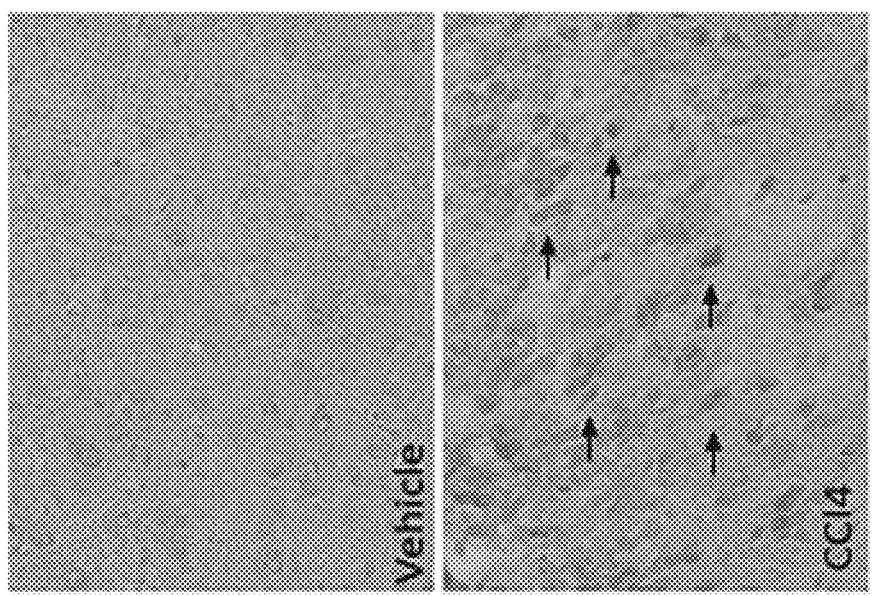
Figure 5B:
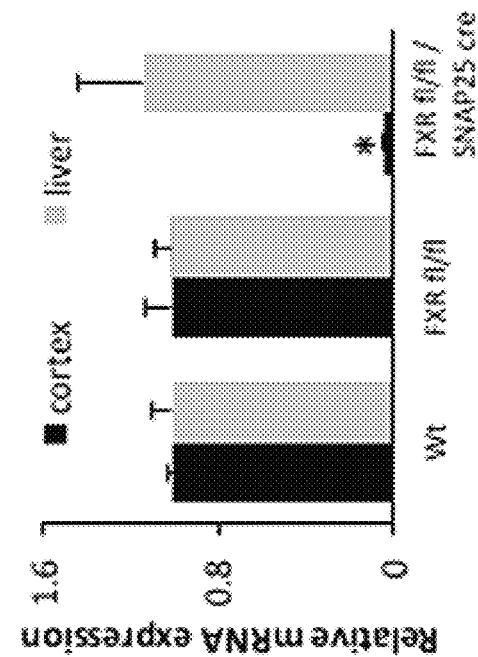
FIG. 5A-H show representative data demonstrating that neuron-specific FXR knockout mice are resistant to the development of Type C HE.
Figure 5A:
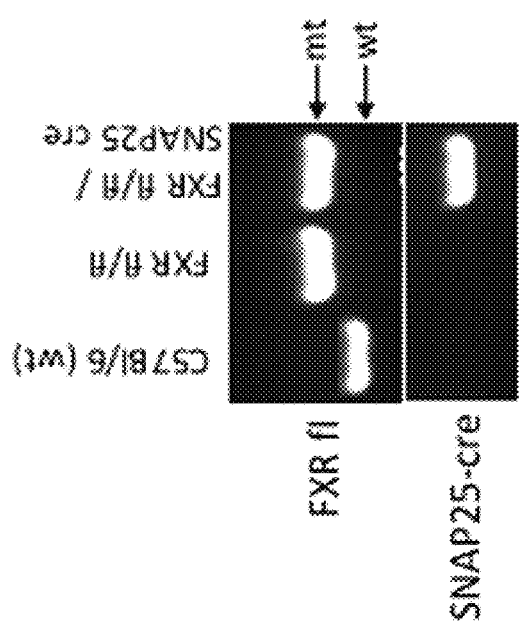
Figure 5D:
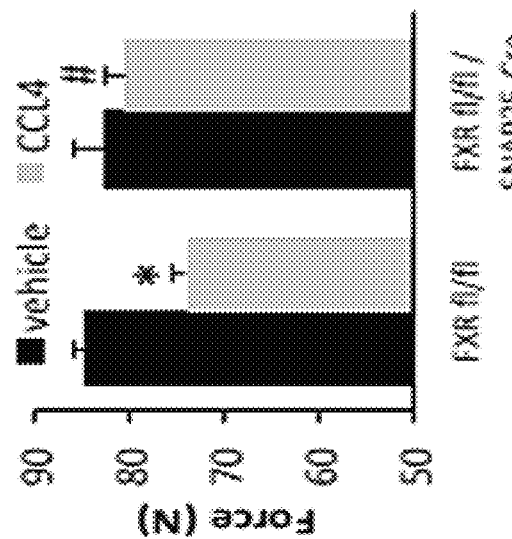
Figure 5C:
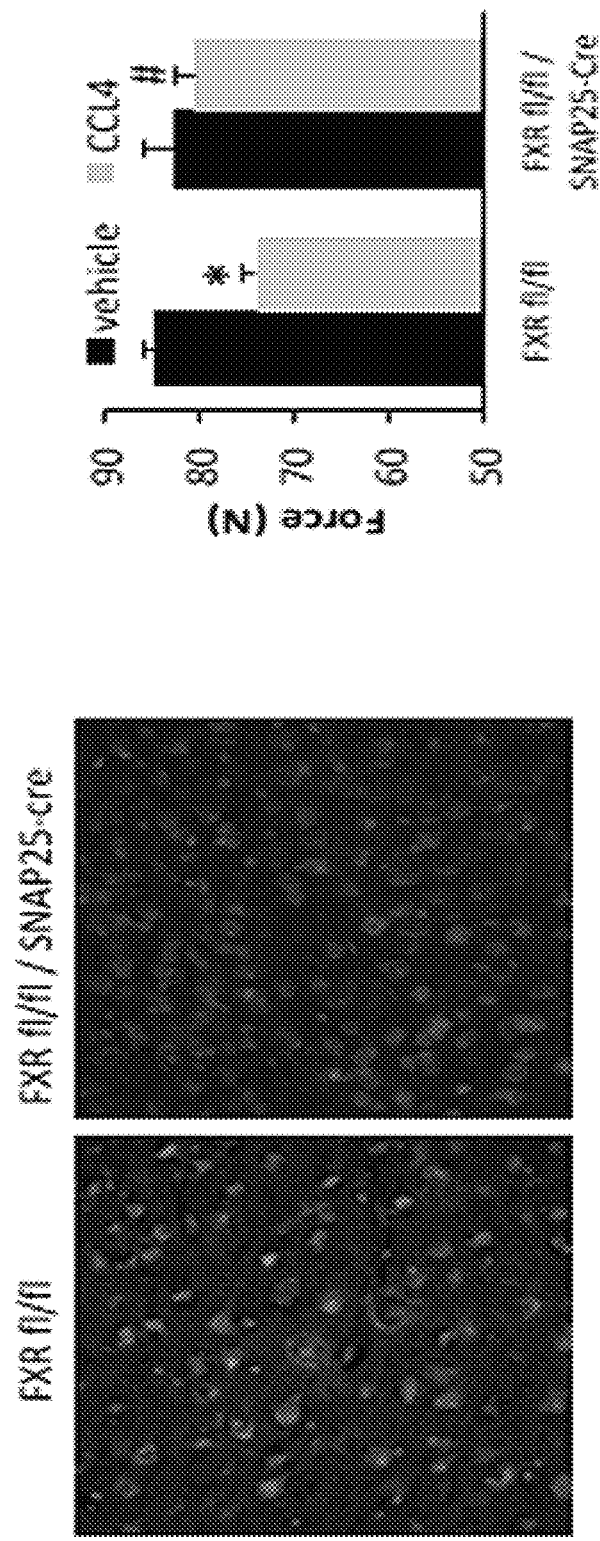
Figure 5F:
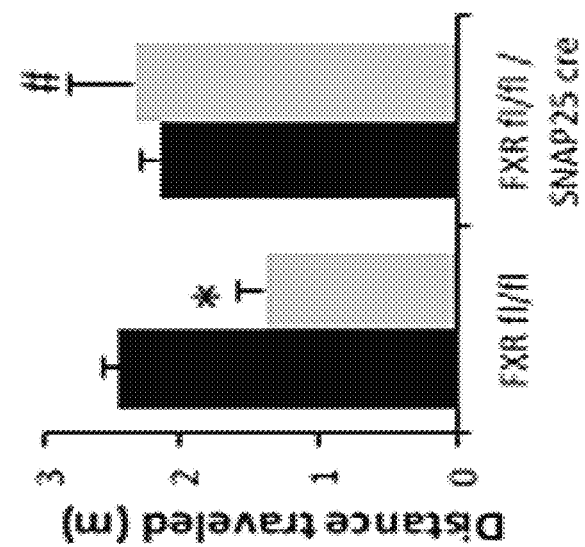
Figure 5E:
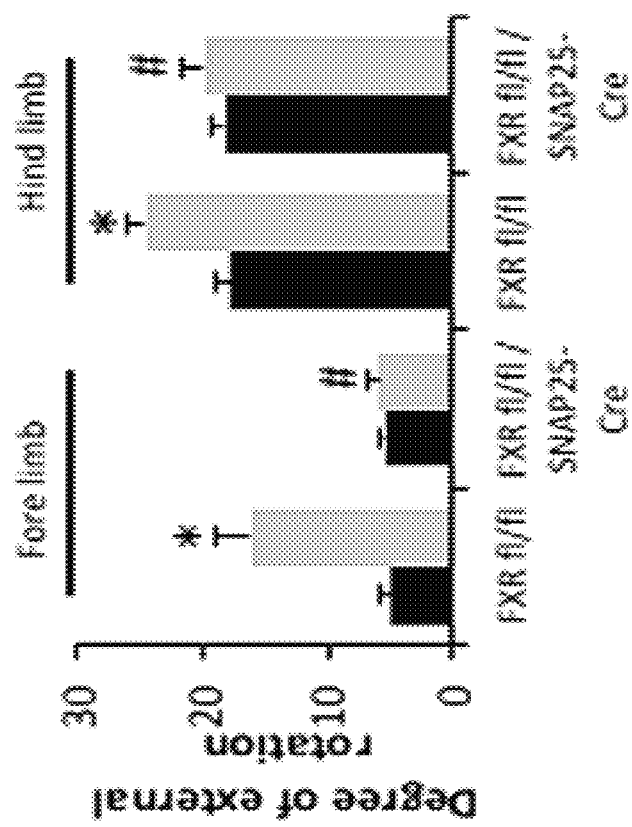
Figures 5G, 5H:
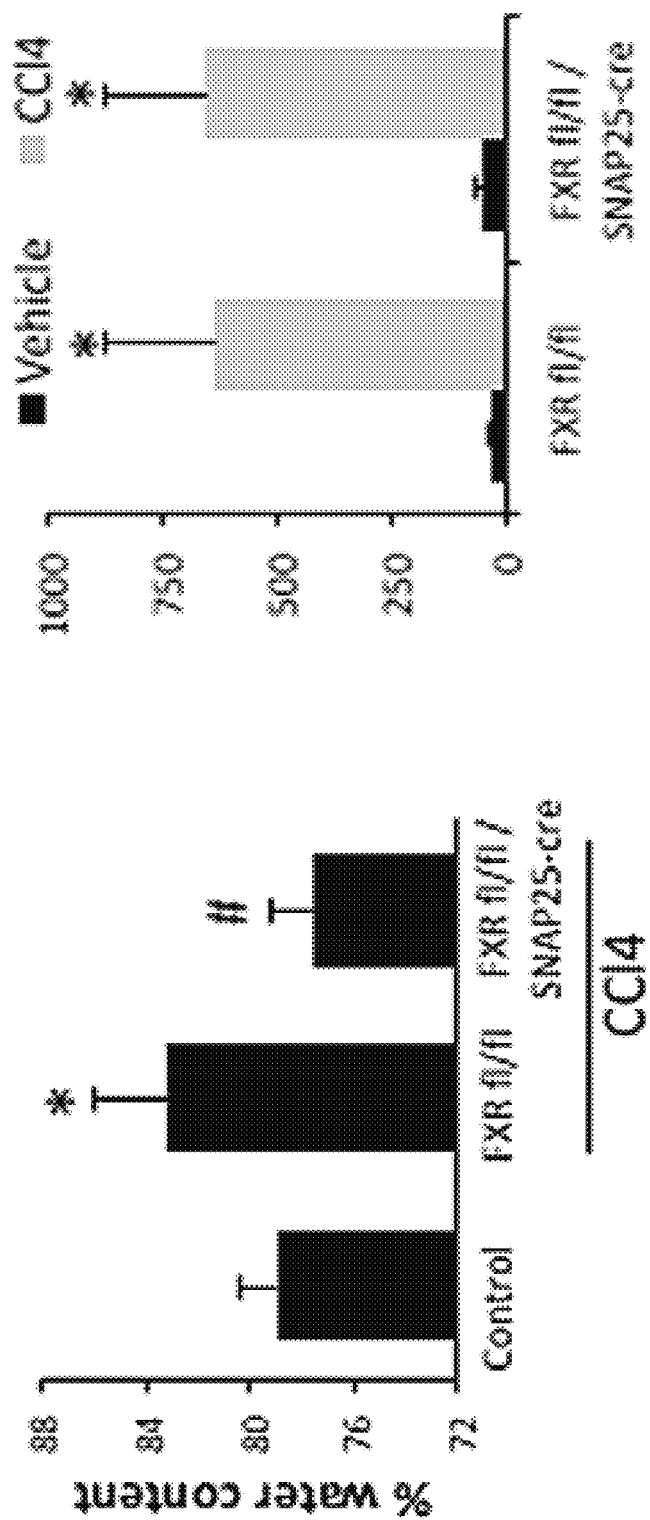

Referring to FIG. 4G and FIG. 4H, FXR immunoreactivity was also assessed in the cortex from CCl4-treated mice (FIG. 4G) and in human tissue (FIG. 4H) by immunohistochemistry.

d. Neuron-Specific Fxr Knockout Mice are Resistant to the Development of Type C HE To assess the effects of FXR signaling in the brain during liver cirrhosis, a neuron-specific FXR knockout mouse line was established by crossing Floxed FXR mice with a mouse line expressing Cre-recombinase under the control of the neuron-specific marker synaptosomal-associated protein 25 (SNAP25). Genotyping protocols in tail snips indicated the presence of the floxed FXR transgene in both the floxed FXR mouse (FXR fl/fl) and the FXR fl/fl/SNAP25 cre mouse, but not C57Bl/6 (wildtype; WT) mice and the transcript for SNAP25 cre was found only in the FXR fl/fl/SNAP25 cre mouse line (FIG. 5A). FXR expression in the cortex and liver were similar between WT and FXR fl/fl mice, but was significantly suppressed specifically in the cortex (brain), but not liver of FXR fl/fl/SNAP25 cre (FIG. 5B). Furthermore, similar to previous studies, FXR immunoreactivity (red) was found to co-localize with the neuronal marker NeuN (green) in the cortex of floxed FXR mice, but was absent in the FXR fl/fl/SNAP25 cre mice (FIG. 5C). To assess the effects of neuron-specific knockout of FXR on the neuromuscular and neurological deficits associated with chronic liver disease, mice were treated chronically with CCl4. There was a decrease in grip strength indicative of neuromuscular impairment in floxed FXR mice treated with CCl4, which was absent in mice lacking neuronal FXR expression (FIG. 5D). Similarly, using the Digigait® gait analysis treadmill to assess indices of ataxia, there was an increased degree of external rotation in the fore and hindlimb paw angle in floxed FXR mice treated with CCl4, which was absent in mice lacking neuronal FXR expression (FIG. 5E), suggesting that indices of ataxia may not develop in mice lacking neuronal FXR expression. Furthermore, CCl4 treatment decreased the distance travelled on the Rotarod in floxed FXR mice, but not in mice lacking neuronal FXR expression (FIG. 5F), suggesting that deficits in motor co-ordination associated with the development of HE were absent in mice lacking neuronal FXR expression. Lastly, cerebral edema, a key biochemical feature of HE, was evident in floxed FXR mice after CCl4 treatment, but absent in mice lacking neuronal FXR expression (FIG. 5G). To ensure that the differences in susceptibility between floxed FXR and FXR fl/fl/SNAP25 cre mice to the development of HE symptoms were not due to a difference in the underlying liver damage, the presence of liver enzymes in the serum was assessed. Serum levels of alanine transferase (ALT), aspartate transferase (AST), and total bilirubin were comparable between the different mouse strains (FIG. 5H and data not shown), indicating that the knockout of FXR expression in the neurons specifically altered the neurological complications without influencing the underlying chronic liver injury.

Referring to FIG. 5A and FIG. 5B, C57Bl/6, FXR fl/fl and FXR fl/fl/SNAP25-Cre mice were genotyped for the presence of the Floxed FXR transgene and SMAP25-cre transgene by PCR (FIG. 5A), and were characterized for the expression of FXR in the liver and cortex by qPCR (FIG. 5B). Referring to FIG. 5C, the cellular location of FXR immunoreactivity in the cortex was also assessed using the neuronal marker NeuN and DAPI as counterstains. Referring to FIG. 5D-F, FXR fl/fl or FXR fl/fl/SNAP25-Cre mice were treated with CCl4 and neurological impairment was assessed by grip strength measurement (neuromuscular function; FIG. 5D), paw angle (index of ataxia; FIG. 5E), and distance traveled on the Rotarod (balance and motor co-ordination; FIG. 5F). Referring to FIG. 5G, cerebral edema was also assessed using the wet weight/dry weight method. Referring to FIG. 5H, the degree of underlying liver damage was assessed by serum ALT. Data are avg±SEM, *$p<0.05$ vs sham or vehicle; #$p<0.05$ vs CCl4-treated FXR fl/fl.

e. Cholesterol Homeostasis is Altered in Type C HE

Figures 6A, 6B:
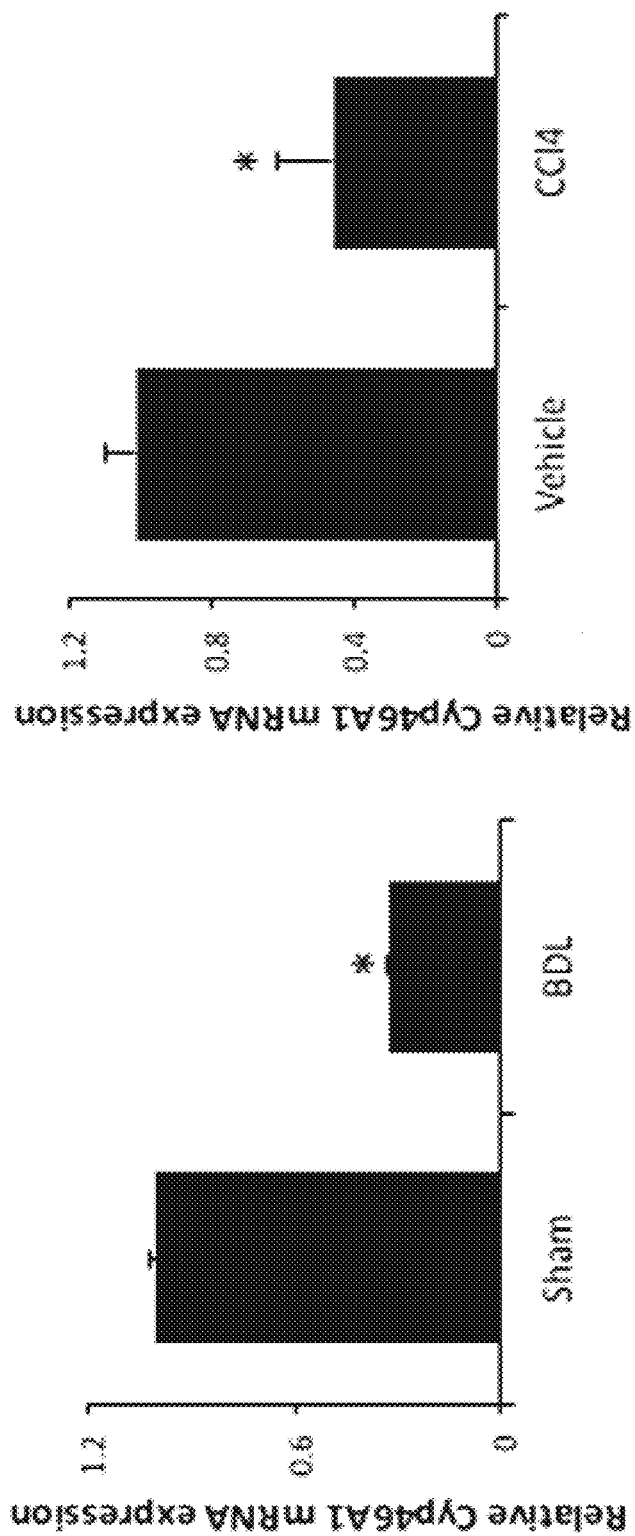
FIG. 6A-H show representative data relating to the expression of Cyp46A1 in models of Type C HE.
Figure 6D:
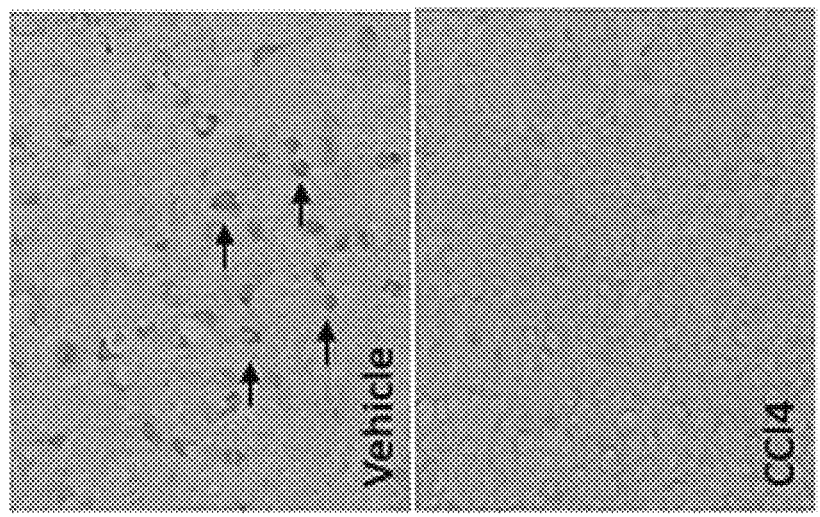
Figure 6C:
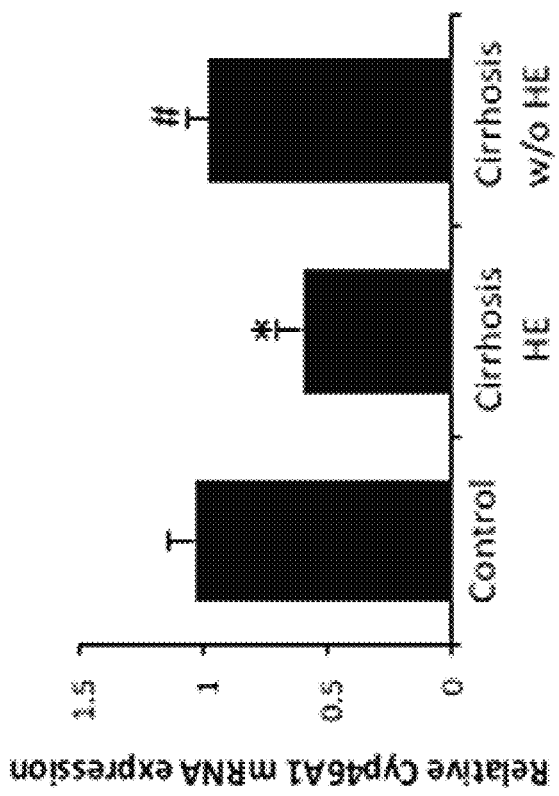
Figure 6F:
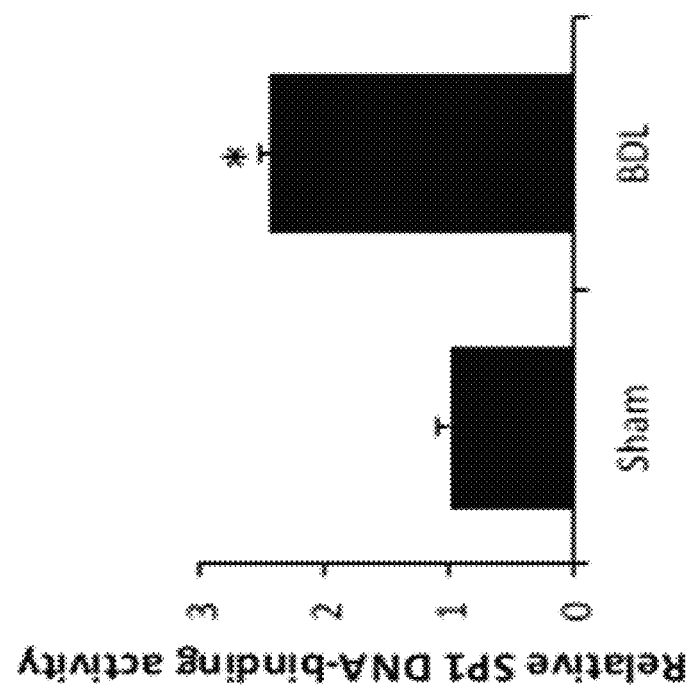

Aberrant bile acid signaling can contribute to the neurological complications of acute liver failure via FXR-mediated events leading to the suppression of Cyp46A1 expression and subsequent dysregulation of cholesterol homeostasis. To determine if a similar consequence of aberrant bile acid signaling in the brain occurs during liver cirrhosis, the expression of Cyp46A1 was assessed in models of Type C HE. Cyp46A1 mRNA expression decreased in the frontal cortex of BDL rats (FIG. 6A), and CCl4-treated mice (FIG. 6B) as well as in patients who died with cirrhosis with HE (FIG. 6C) compared to controls. Furthermore, consistent with previous studies, Cyp46A1 immunoreactivity was found predominantly in neurons in the frontal cortex and was decreased after CCl4 treatment (FIG. 6D). Interestingly, Cyp46A1 expression was not decreased in the neuron-specific FXR knockout mice after CCl4 (FIG. 6E), suggesting that Cyp46A1 may be under the control of FXR. A database screen of the Cyp46A1 promoter sequence failed to identify any canonical FXR DNA-binding sequences, indicating that FXR may not directly control the transcriptional activity of Cyp46A1. However, the transcription factor Sp1 is a negative regulator of Cyp46A1 expression in neurons, and FXR has previously been shown to regulate Sp1 DNA-binding activity, although the mechanism by which this occurs is unclear. Therefore, the feasibility of whether Sp1 may be involved in the FXR-mediated suppression of Cyp46A1 was assessed. Indeed, Sp1 DNA binding activity was significantly increased in the frontal cortex of BDL rats (FIG. 6F), and in floxed FXR mice, but not neuron-specific FXR knockout mice treated with CCl4 (FIG. 6G). Lastly, the mRNA expression of Sp1 was significantly increased in the frontal cortex of patients who died of cirrhosis with HE compared to control or patients who died with cirrhosis without HE (FIG. 6H). Without wishing to be bound by theory, these data suggest that Cyp46A1 expression is suppressed in the frontal cortex in models of Type C HE via a mechanism requiring neuronal FXR expression and perhaps via an increase in Sp1 signaling. The precise mechanism of action of FXR activating Sp1 DNA-binding activity and the subsequent role this action plays on Cyp46A1 expression is unknown.

Figure 6E:
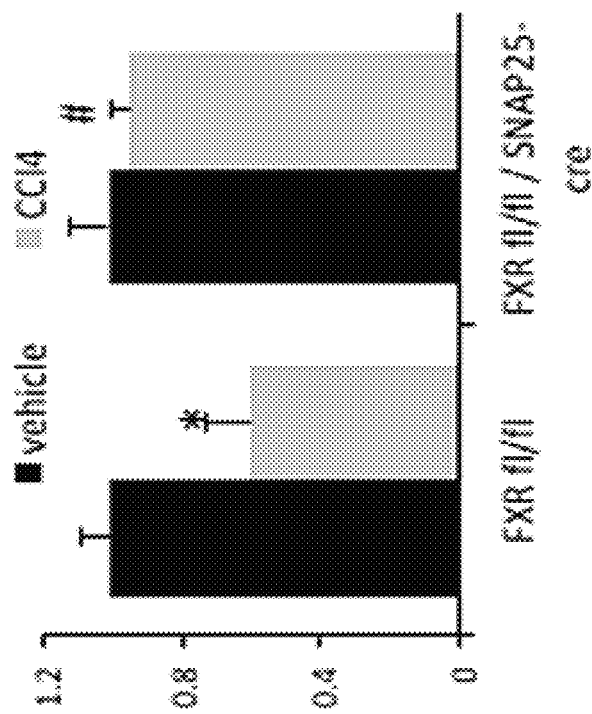
Figure 6H:
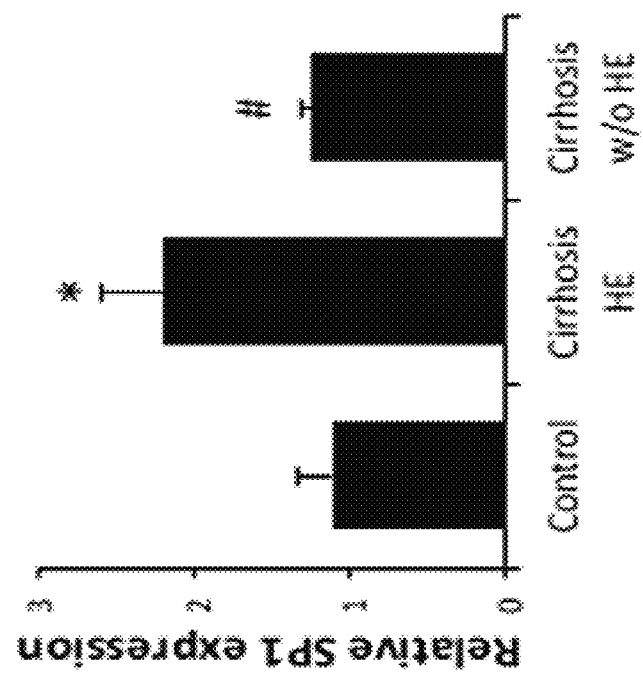
Figure 6G:
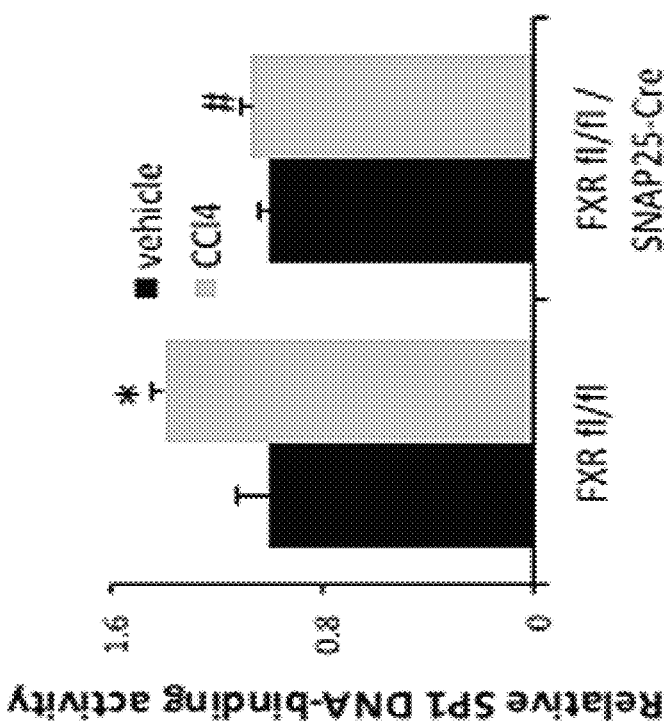

Referring to FIG. 6A-C and FIG. 6E, the expression of Cyp46A1 was assessed in cortical samples from BDL rats (FIG. 6A), CCl4-treated mice (FIG. 6B), and human autopsy tissue from patients who died with HE, cirrhosis without HE, and age- and gender-matched controls (FIG. 6C), as well as FXR fl/fl and FXR fl/fl/SNAP25-Cre mice treated with CCl4 (FIG. 6E) by qPCR. Referring to FIG. 6D, Cyp46A1 immunoreactivity was also assessed in the cortex from CCl4-treated mice. Referring to FIG. 6F-H, the DNA-binding activity of Sp1 was assessed in BDL rats (FIG. 6F) and FXR fl/fl and FXR fl/fl/SNAP25-Cre mice treated with CCl4 (FIG. 6G), and Sp1 mRNA expression was assessed in human autopsy tissue from patients who died with HE, cirrhosis without HE, and age- and gender-matched controls (FIG. 6H). Data are avg±SEM, *$p<0.05$ vs sham or vehicle; #$p<0.05$ vs CCl4-treated FXR fl/fl.

Figure 7A:
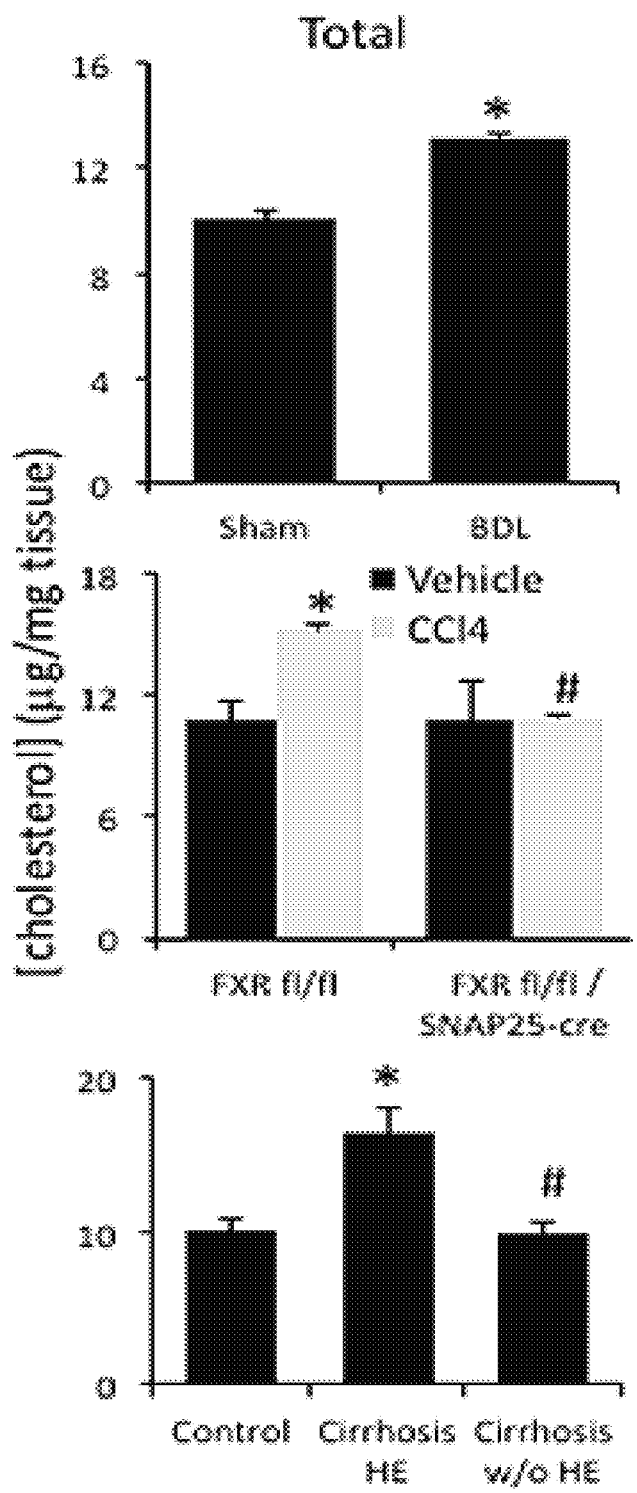
FIG. 7A-C show representative data relating to the down-regulation in Cyp46A1 expression in relation to levels of cholesterol and 24-(S)-hydroxycholesterol.

Next, whether the downregulation in Cyp46A1 expression correlated with an alteration in levels of the substrate (cholesterol) and product (24-(S)-hydroxycholesterol) of the reaction catalyzed by Cyp46A1 was assessed in models of Type C HE. There was increased cholesterol levels in the frontal cortex of BDL rats, floxed FXR mice (but not neuron-specific FXR knockout mice) treated with CCl4, and in autopsy samples from patients who died with cirrhosis with HE compared to control or patients who died with cirrhosis without HE (FIG. 7A). This increase in total cholesterol corresponded to an increase in the unesterified cholesterol (FIG. 7B) but not in the esterified cholesterol in each model (data not shown). Increased cholesterol content could also be observed in cortical sections from CCl4-treated mice by Nile red staining which co-localized with both glial fibrillary acidic protein (GFAP; astrocyte marker) and NeuN (neuronal marker) staining (data not shown), indicating the cholesterol accumulation was likely in neurons and astrocytes. There was a concomitant decrease in the tissue levels of 24-(S)-hydroxycholesterol in the frontal cortex of BDL rats, floxed FXR mice (but not neuron-specific FXR knockout mice) treated with CCl4 and in autopsy samples from patients who died of cirrhosis with HE compared to control or patients who died with cirrhosis without HE (FIG. 7C).

Figure 7B:
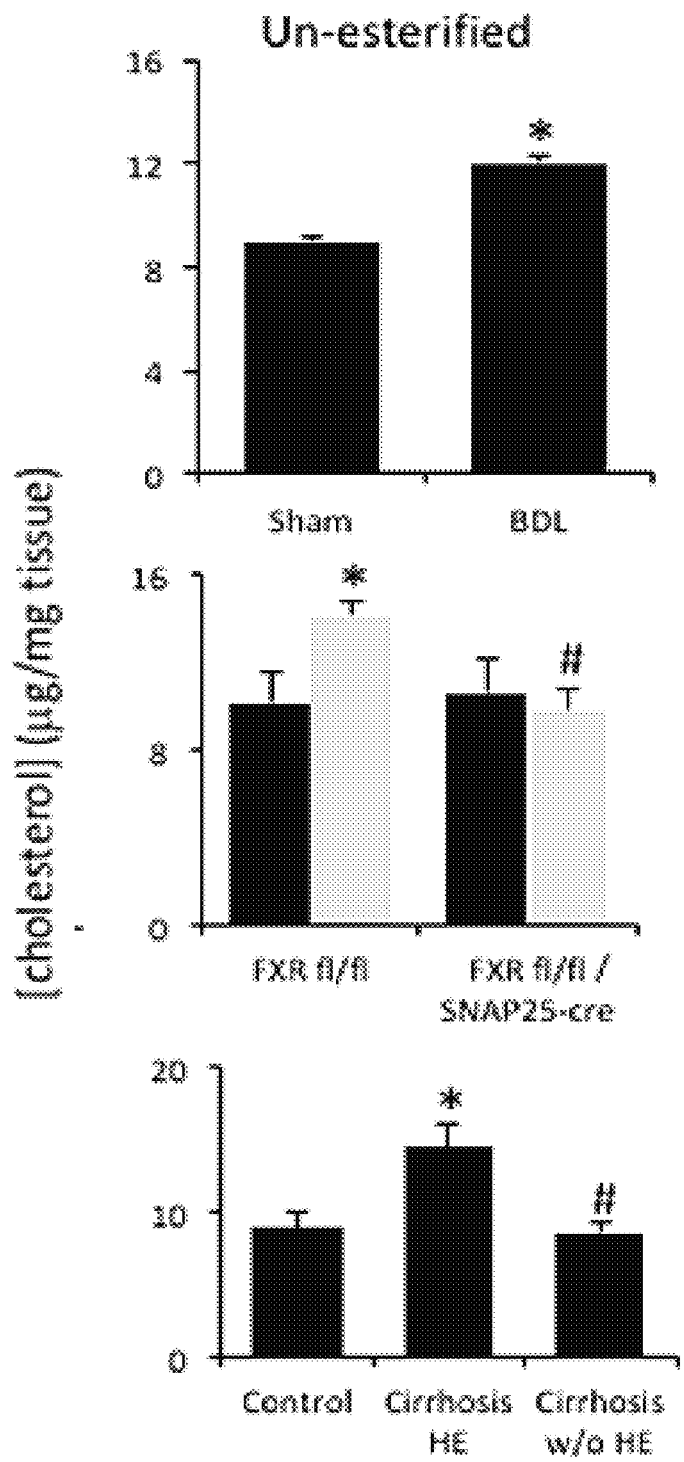
Figure 7C:
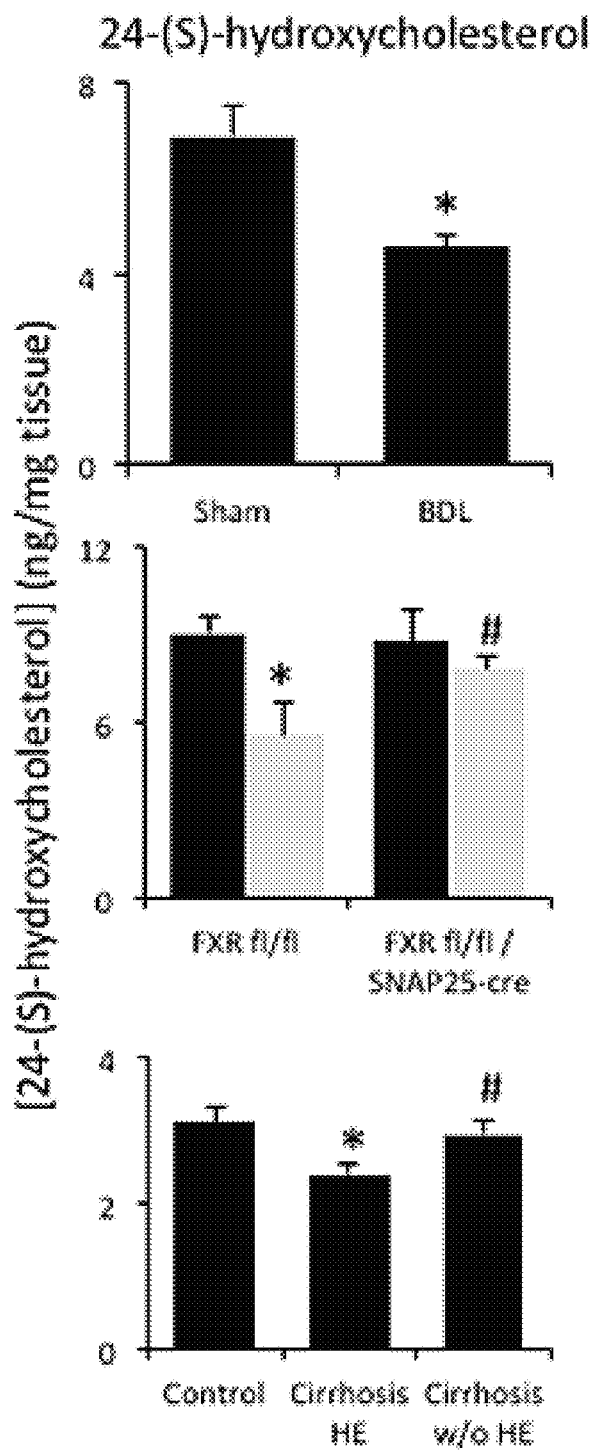

Referring to FIG. 7A-C, total cholesterol (FIG. 7A), un-esterified cholesterol (FIG. 7B), and 24-(S)-hydroxycholesterol (FIG. 7C) were assessed in BDL rats (upper), FXR fl/fl and FXR fl/fl/SNAP25-Cre mice treated with CCl4 (middle), and in human autopsy tissue from patients who died with HE, cirrhosis without HE, and age- and gender-matched controls (lower). Data are avg±SEM, *p<0.05 vs sham or vehicle; #p<0.05 vs CCl4-treated FXR fl/fl.

f. Aberrant Fxr Activation During HE has Implications on Neurosteroid Synthesis

One of the major implications of disrupted cholesterol homeostasis in the brain may be a dysregulation of neurosteroid synthesis. The expression of the cholesterol transporter TSPO is thought to be upregulated in the cortex of rodent models and human samples of hepatic encephalopathy, although not much is known about the expression of Cyp450scc, the major enzyme responsible for neurosteroid synthesis. TSPO and Cyp450scc were increased in the cortex of (i) BDL rats compared to sham (FIG. 8A); (ii) floxed FXR mice treated with CCl4 compared to vehicle-treated, but not in neuron-specific FXR knockout mice (FIG. 8B); and (iii) in autopsy samples from patients who died of cirrhosis with HE, compared to patients who died with cirrhosis without HE or control patients (FIG. 8C). Furthermore, there was a concomitant increase in the levels of allopregnanolone in cortical tissue from BDL rats (FIG. 8D) and from floxed FXR mice, but not in neuron-specific FXR knockout mice, after CCl4 treatment (FIG. 8E). Without wishing to be bound by theory, these data indicate that the expression of the key genes, TSPO and Cyp450scc are altered in the models of Type C HE disclosed herein and appear to be dependent on FXR signaling in the brain.

Figure 8B:
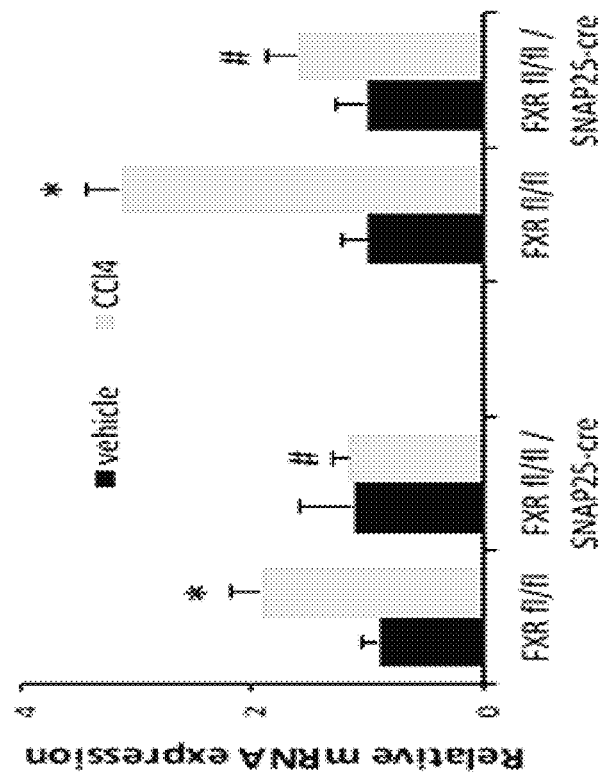
FIG. 8A-E show representative data demonstrating that aberrant FXR activation during HE has implications on neurosteroid synthesis.
Figure 8A:
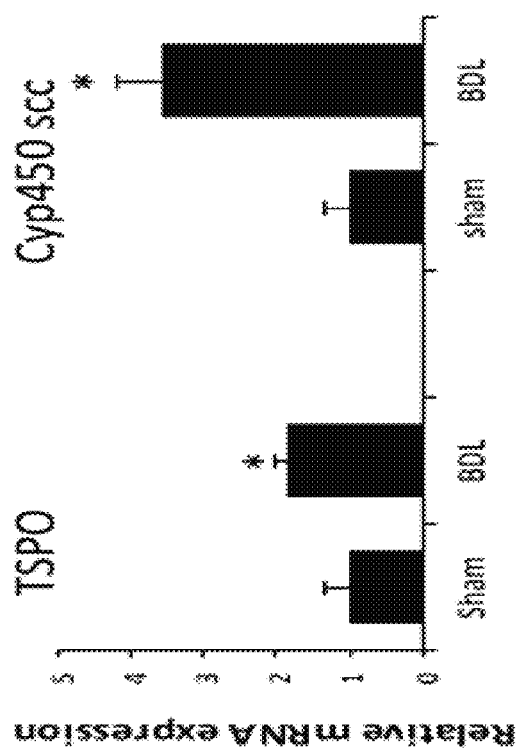
Figure 8C:
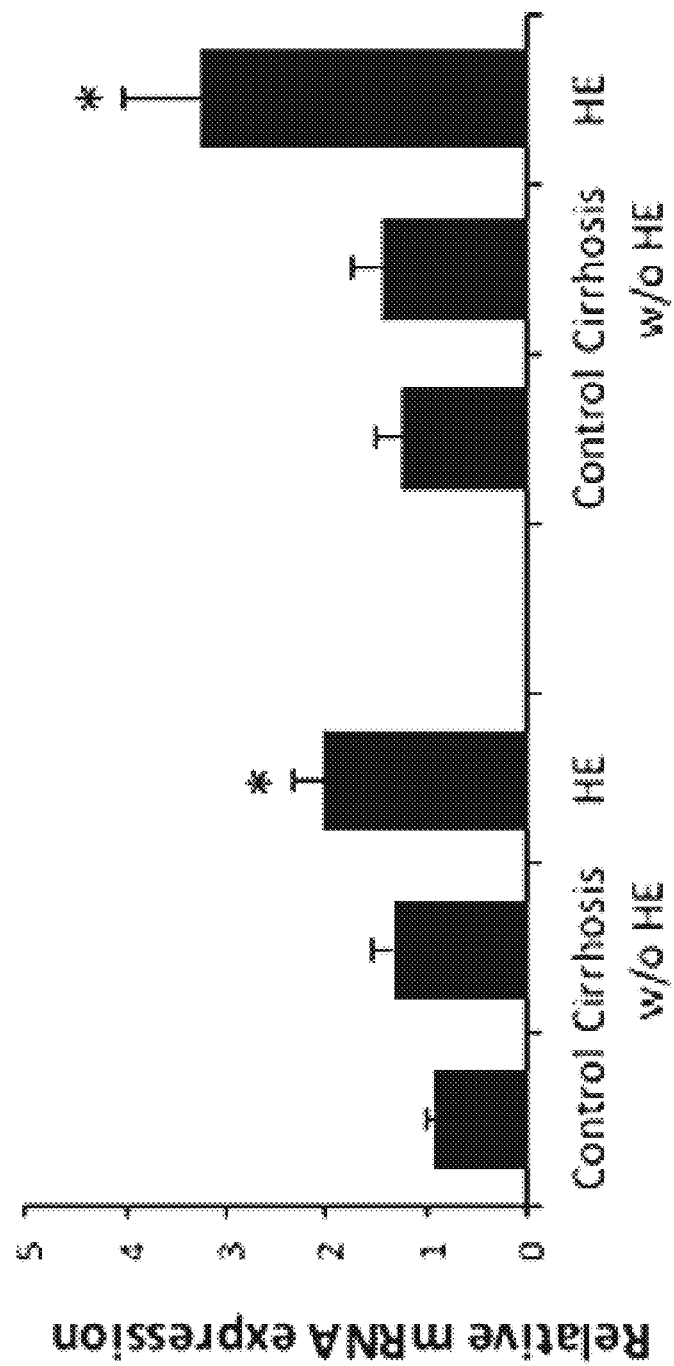
Figure 8E:
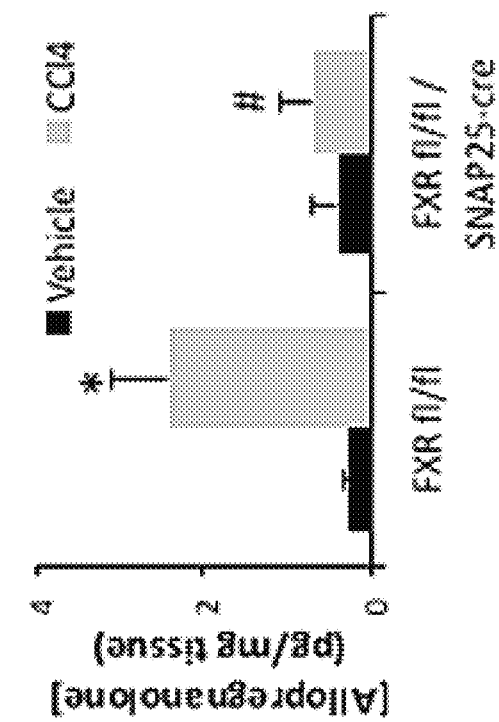
Figure 8D:
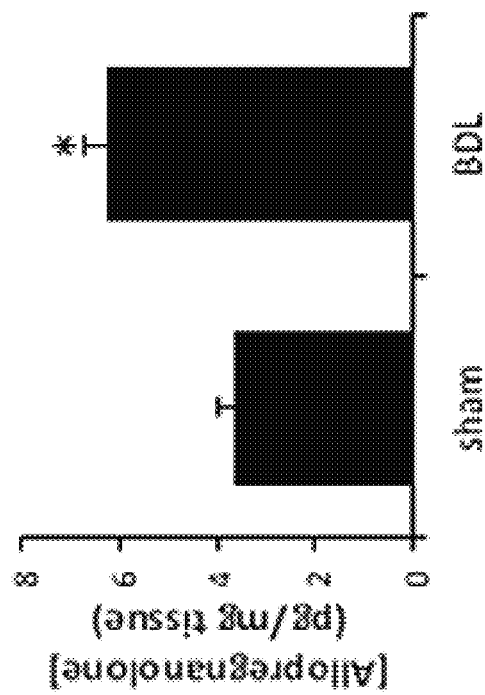

Referring to FIG. 8A-C, TSPO and Cyp450scc expression was assessed in cortical extracts from BDL rats (FIG. 8A), FXR fl/fl and FXR fl/fl/SNAP25-Cre mice treated with CCl4 (FIG. 8B), and human autopsy tissue from patients who died with HE, cirrhosis without HE, and age- and gender-matched controls (FIG. 8C) by qPCR. Referring to FIG. 8D and FIG. 8E, allopregnanolone levels were assessed in cortical extracts from BDL rats (FIG. 8D) and FXR fl/fl and FXR fl/fl/SNAP25-Cre mice treated with CCl4 (FIG. 8E). Data are avg±SEM, *p<0.05 vs sham or vehicle; #p<0.05 vs CCl4-treated FXR fl/fl.

g. Summary of Preliminary Data

Figure 9:
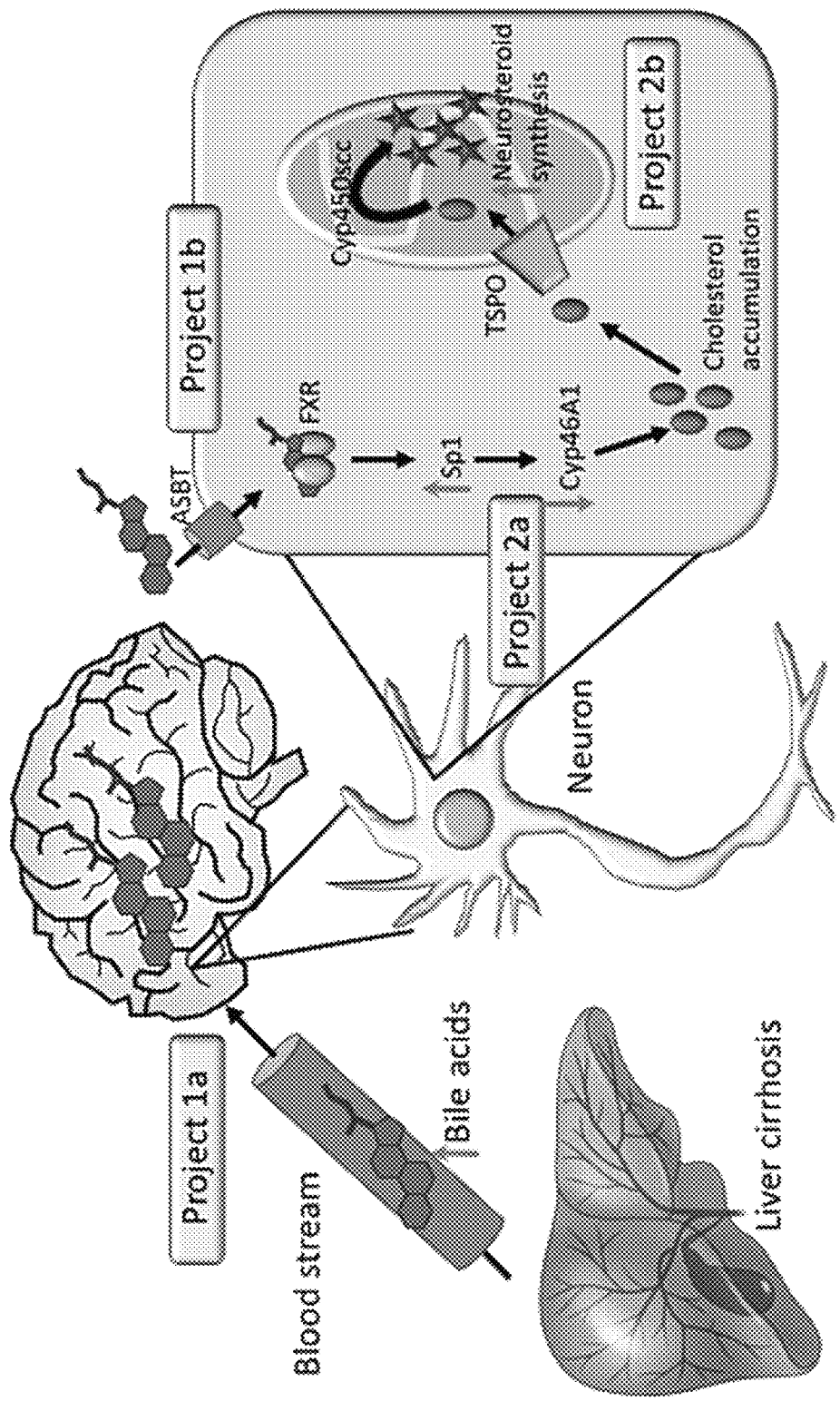
FIG. 9 shows a representative schematic diagram illustrating the pathogenesis of HE due to chronic liver cirrhosis.

Without wishing to be bound by theory, these data suggest that (i) aberrant bile acid signaling may be playing a key pathogenic role in the development of Type C HE; (ii) the increased bile acid content in the brain is exerting effects on neurological function, at least in part, via the activation of neuronal FXR signaling; (iii) downstream of aberrant FXR signaling in neurons is suppression of Cyp46A1 expression and subsequent increase in cholesterol accumulation; and (iv) the increased cholesterol availability may be driving neurosteroid synthesis which may ultimately have an impact on neurological function during HE. A hypothesis based on these data is shown in FIG. 9. Without wishing to be bound by theory, it appears that increased bile acid content in the brain occurs as an early event during the pathogenesis of HE due to chronic liver cirrhosis. This aberrant bile acid content may enter neurons of the affected brain regions where it can alter expression of key enzymes responsible for cholesterol homeostasis in the brain via FXR-mediated actions, and subsequently, alter neurosteroid synthesis. Thus, strategies to prevent the aberrant bile acid signaling and cholesterol accumulation in the brain, or to counteract the enhanced neurosteroid release, may prove effective treatment targets for the management of HE, especially in patients who have no treatment for their underlying liver disease or who are not transplantation candidates.

3. Cortical Cholesterol Concentrations are Increased in AOM-Treated Mice

Figure 10B:
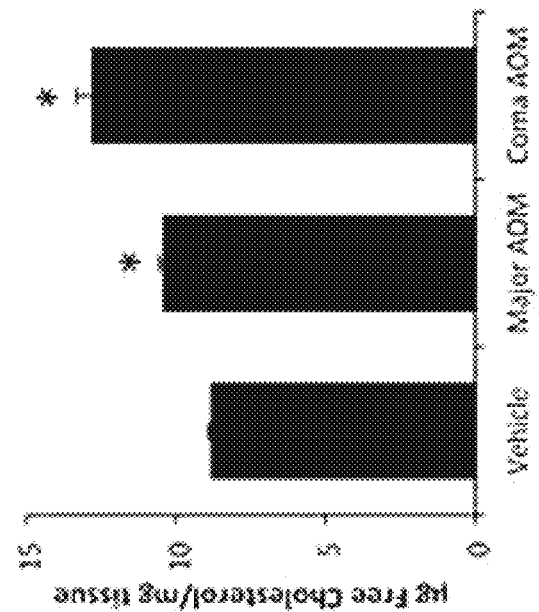
FIG. 10A-E show representative data demonstrating that cholesterol levels are increased in the cortex during AOM-induced hepatic encephalopathy.

It has been previously demonstrated that aberrant bile acid signaling may contribute to the neurological complications of acute liver failure (McMillin, M. et al. (2016) *Am. J. Pathol.* 186(2): 312-23). Little is known about the effects of bile acid signaling in the brain. However, the enzymatic machinery for bile acid synthesis has been shown to be present in the brain and is the predominant method by which the brain regulates cholesterol homeostasis (Lund, E. G. et al. (2003) *J. Biol. Chem.* 278(25): 22980-8). Therefore, without wishing to be bound by theory, it was hypothesized that aberrant bile acid signaling during HE may disrupt cholesterol homeostasis in the brain. Indeed, total cholesterol (FIG. 10A) and free cholesterol (FIG. 10B), but not esterified cholesterol (FIG. 10C) were significantly increased with the onset of major neurological complications in AOM-treated mice. This increase in cholesterol content correlated with increases in both Nile Red (intracellular) and Filipin III (membrane-bound) staining in the brain (FIG. 10D-E). Without wishing to be bound by theory, these data indicate that the total cholesterol content is increased in the brain during acute liver failure, which is distributed both intracellularly and in the membrane.

Figure 10A:
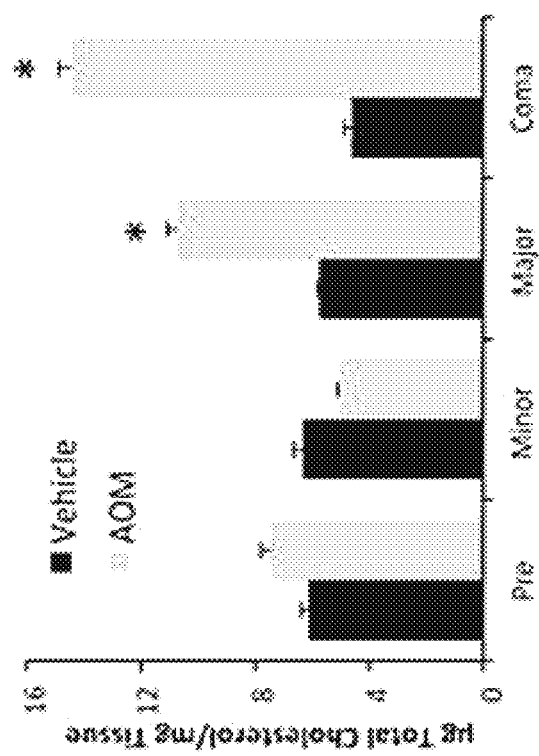
Figure 10C:
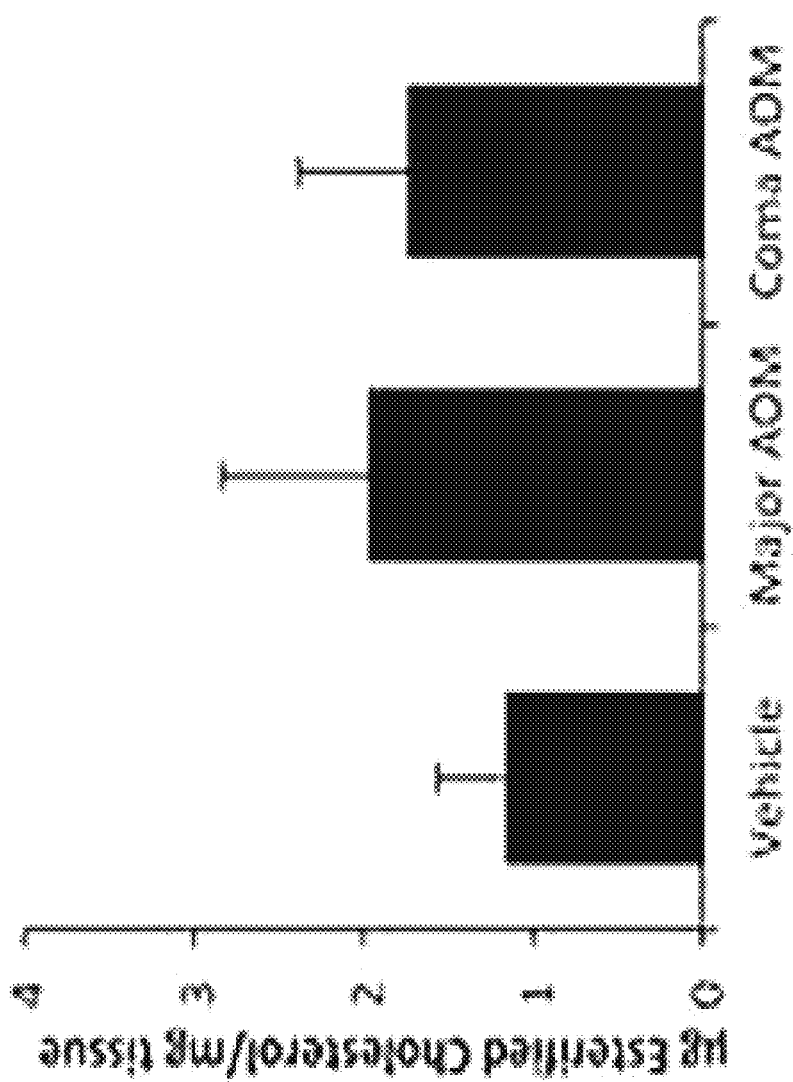
Figure 10D:
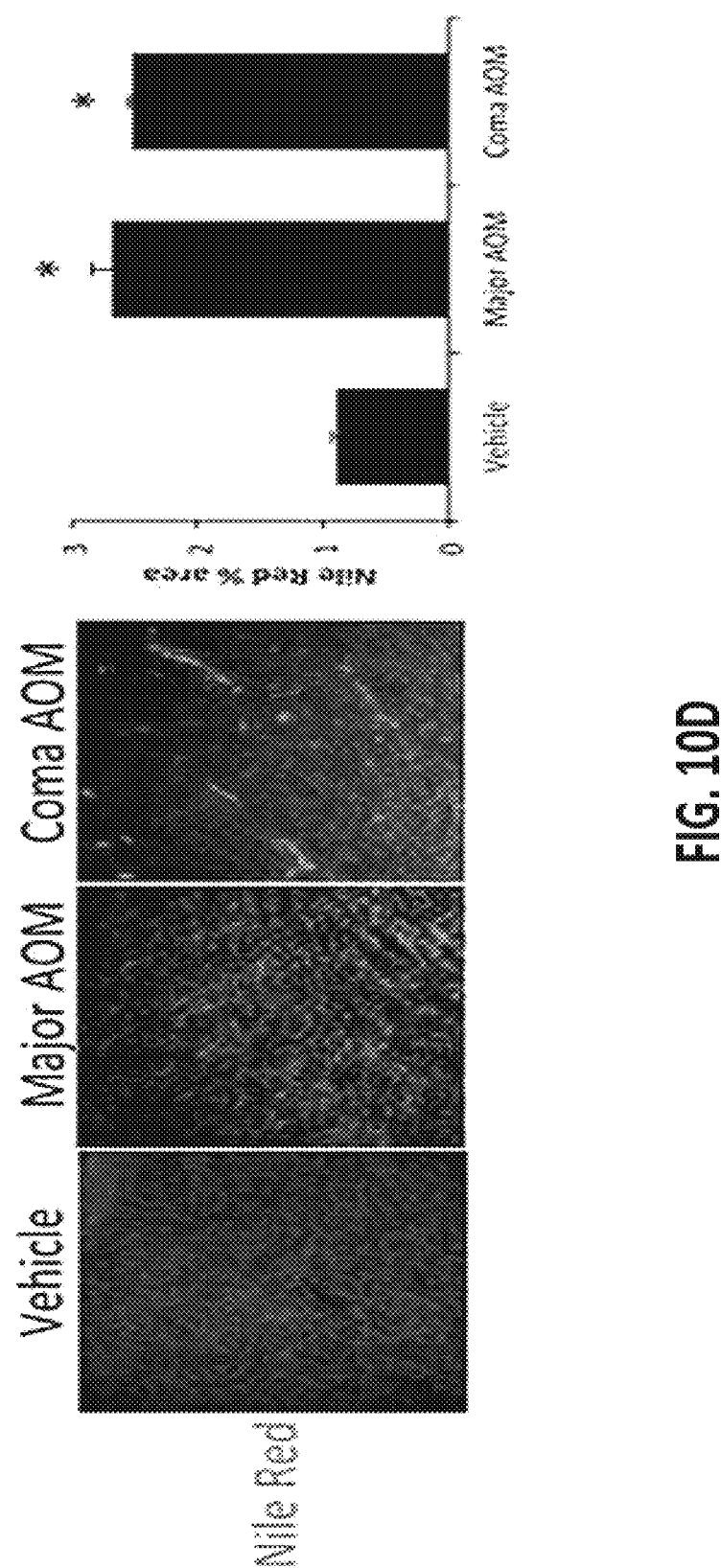
Figure 10E:
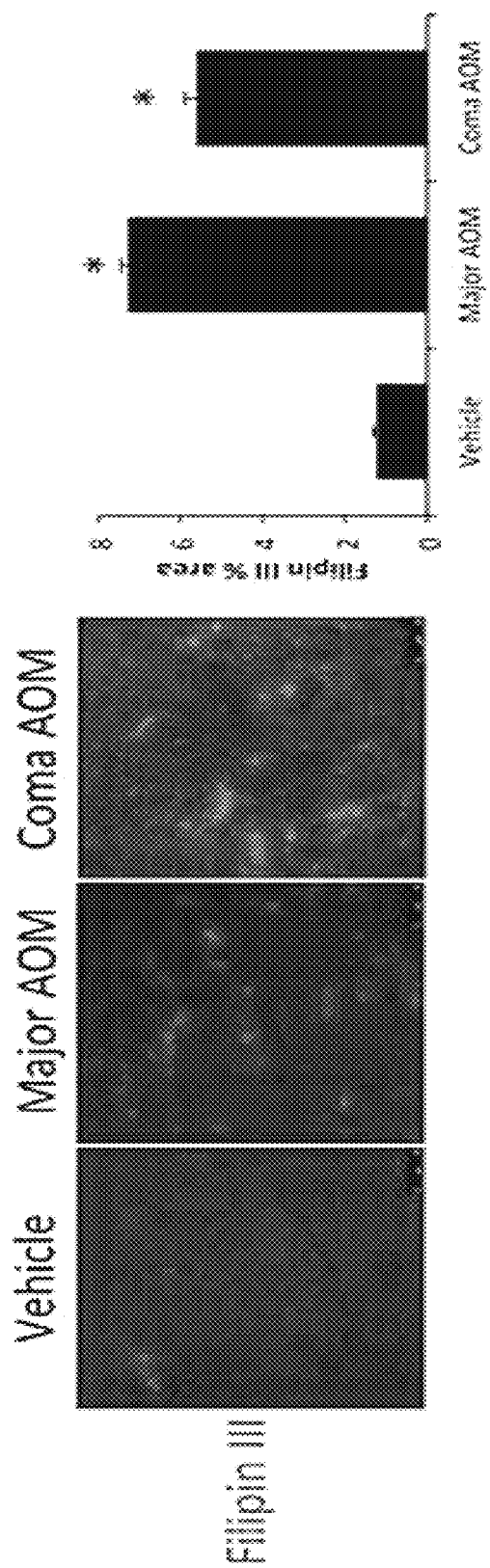

Referring to FIG. 10A, the total cholesterol levels in the cortex of AOM-treated mice at various stages of neurological decline including prior to neurological decline (Pre), when minor neurological decline is evident (Minor), when major neurological decline is evident (Major) and at coma (Coma) are shown. Total cholesterol levels are expressed as µg of cholesterol per mg of cortex tissue. Referring to FIG. 10B, free cholesterol levels in the cortex of vehicle and AOM-treated mice at the stages of major neurological decline and coma are shown. Free cholesterol levels are expressed as µg of cholesterol per mg of cortex tissue. Referring to FIG. 10C, the concentration of esterified cholesterol in vehicle and AOM-treated mice at the stages of major neurological decline and coma are shown. Esterified cholesterol levels are expressed as µg of esterified cholesterol per mg of cortex tissue. Referring to FIG. 10D, Nile Red staining and quantification are presented as percent area in the cortex of vehicle and AOM-treated mice at the major and coma stages of neurological decline. Referring to FIG. 10E, Filipin III staining and quantification are presented as percent area in the cortex of vehicle and AOM-treated mice at the major and coma stages of neurological decline. *=p<0.05 compared to vehicle-treated mice.

4. AOM-Treated Mice have Reduced Cortical Cyp46A1 Activity

To determine if the cholesterol buildup may be due to an impaired clearance pathway, the expression of Cyp46A1 was assessed in mice with acute liver failure. Expression of Cyp46A1 mRNA and protein were downregulated in the cortex of AOM-treated mice exhibiting neurological symptoms of hepatic encephalopathy (FIG. 11A), suggesting that the buildup in cholesterol in the brain may be attributable to an impaired clearance pathway. Interestingly, this downregulation of Cyp46A1 was not evident in mouse models exhibiting attenuated AOM-induced aberrant bile acid signaling in the brain (McMillin, M. (2016) *Am. J. Pathol.*

Figure 11B:
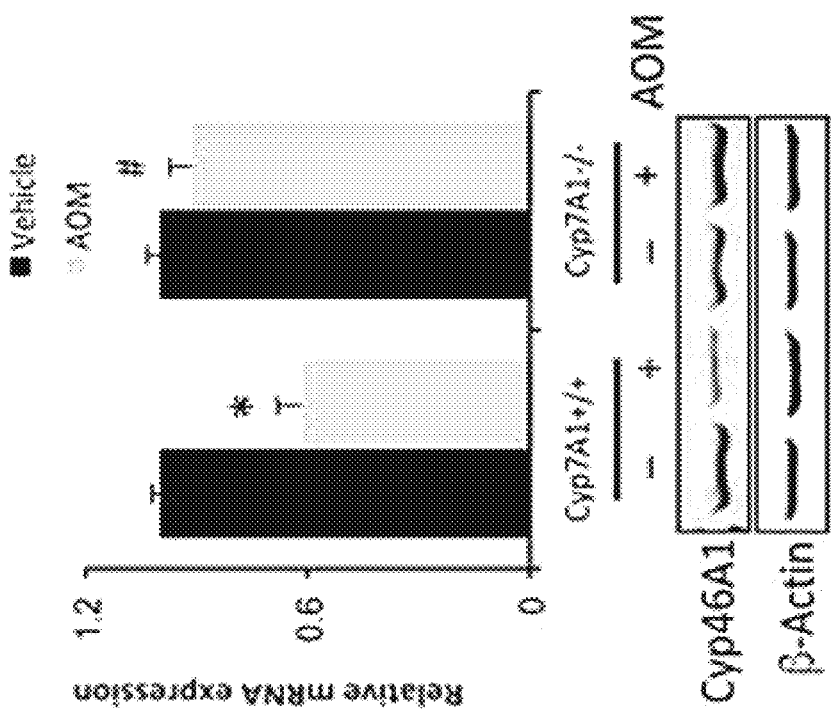
FIG. 11A-E show representative data demonstrating that cortex Cyp46A1 is suppressed in AOM-treated mice via bile acid dependent FXR signaling.

186(2): 312-23). Specifically, it has been previously shown that increases in serum and cortical bile acid content are not evident in Cyp7A1−/− mice after AOM injection, which correlated with a delay in the neurological decline associated with acute liver failure (McMillin, M. (2016) *Am. J. Pathol.* 186(2): 312-23). Furthermore, it has been previously demonstrated that the effects of bile acid signaling in the development of hepatic encephalopathy are, in part, attributable to FXR signaling in neurons and specific knockdown of FXR activity in the brain using a cholestyramine supplemented diet or direct infusion of FXR Morpholino delayed the neurological decline associated with AOM-induced acute liver failure (McMillin, M. (2016) *Am. J. Pathol.* 186(2): 312-23). In Cyp7A1−/− mice, cholestyramine-fed mice or mice infused with FXR morpholino, the downregulation of Cyp46A1 expression in response to AOM injection was attenuated (FIG. 11B-D). To determine if the suppression of Cyp46A1 was attributable to a direct action of FXR-mediated signaling and not a reflection of the degree of neurological impairment in these mice, primary neurons were treated with DCA, a known agonist of FXR (Song, P. et al. (1999) *Physiol. Behav.* 67(5): 819-21), which decreased the expression of Cyp46A1. Without wishing to be bound by theory, this could be prevented by pre-treatment with the FXR antagonist guggulsterone (FIG. 11E).

Figure 11A:
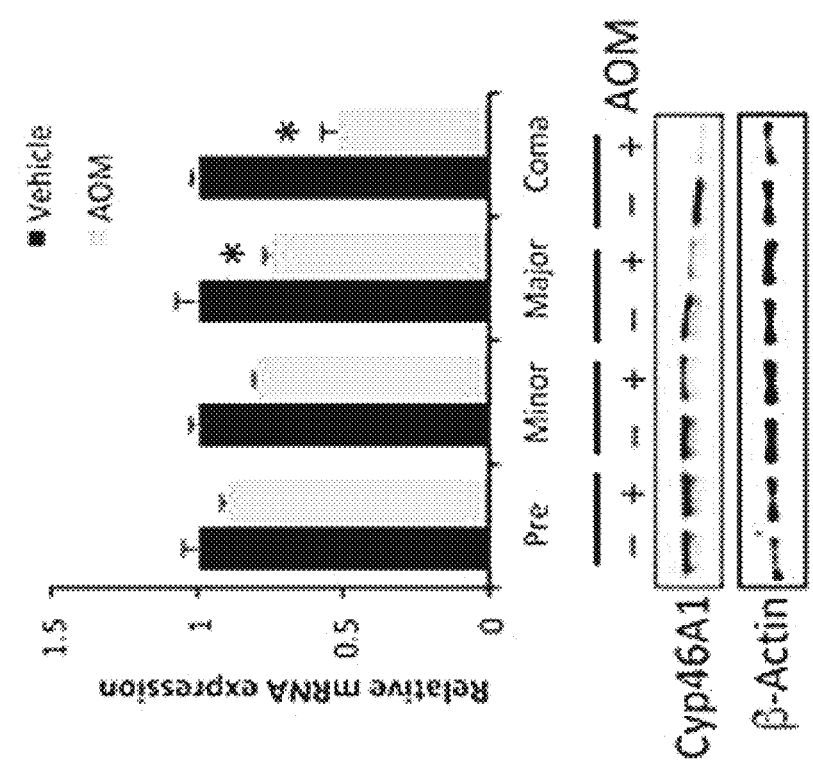
Figures 11C, 11D:
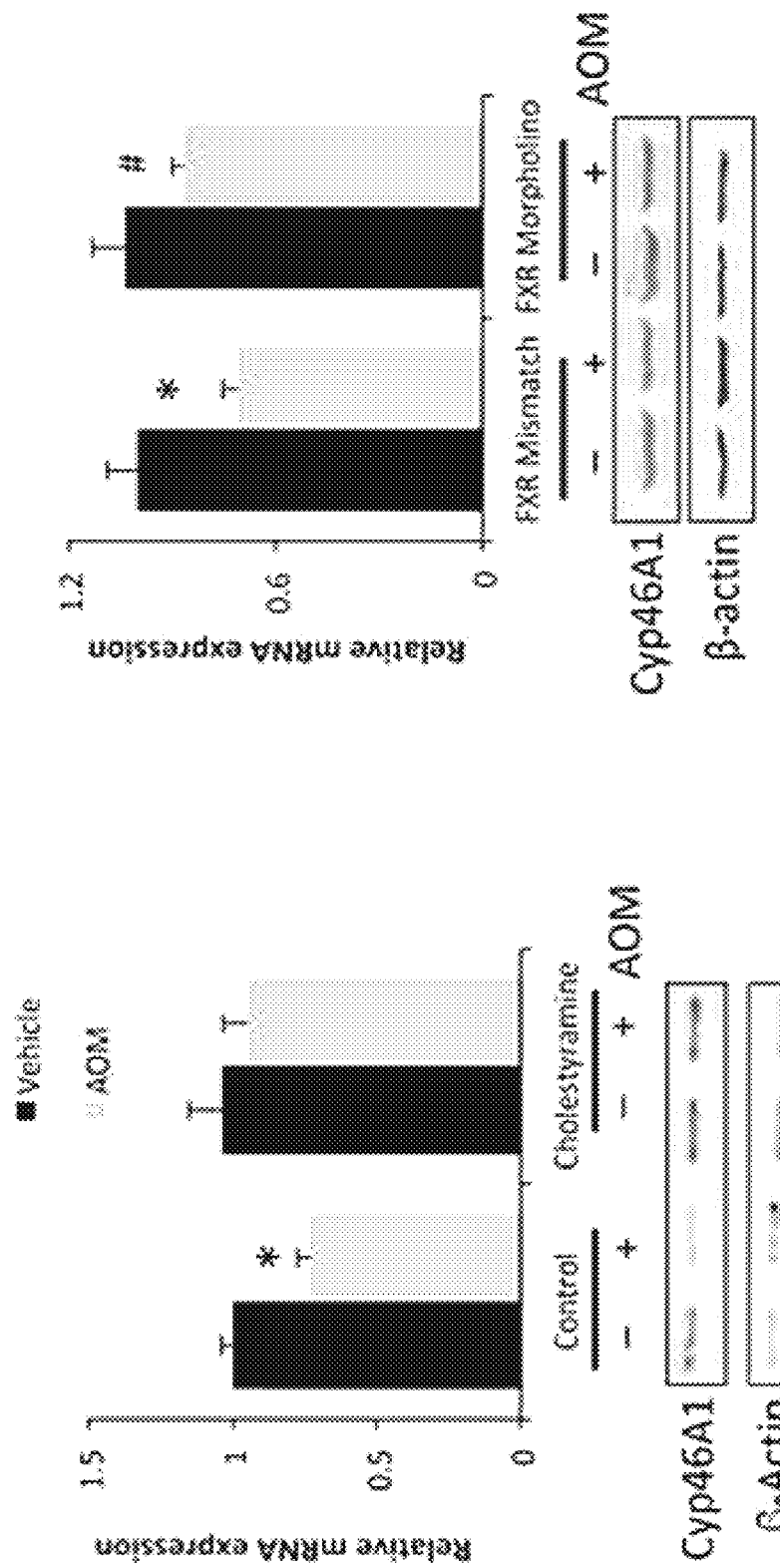
Figure 11E:
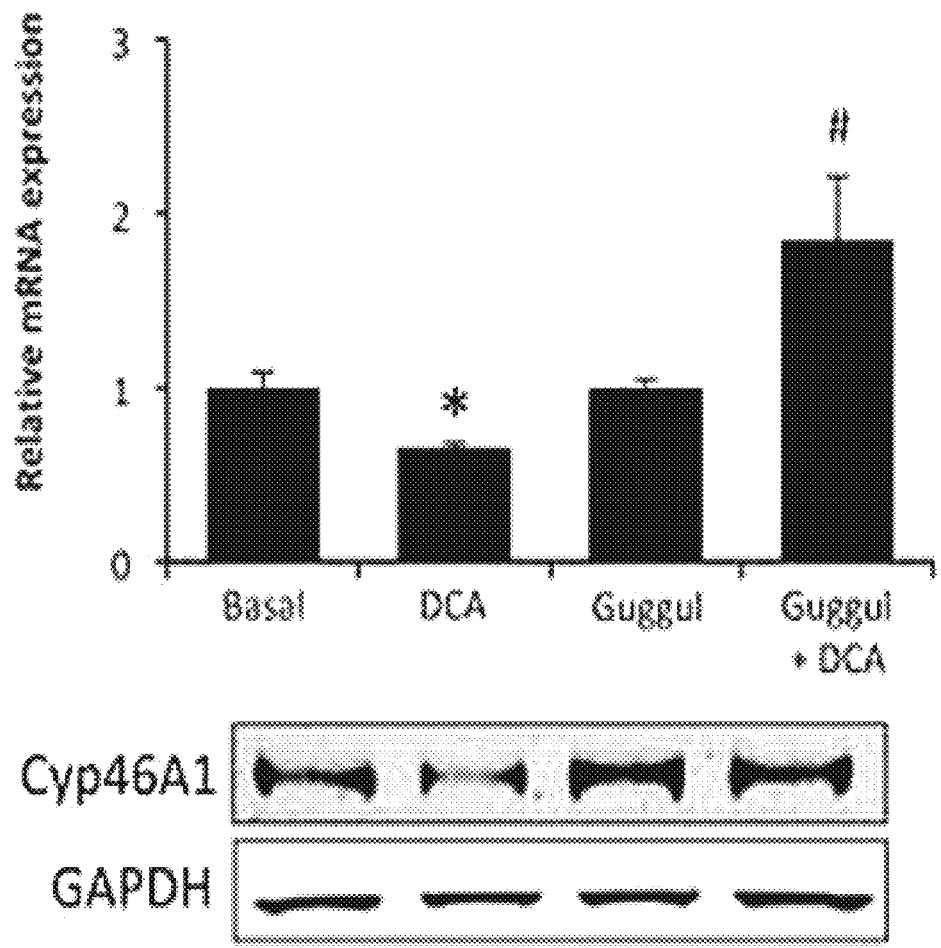

Referring to FIG. 11A, relative Cyp46A1 mRNA expression (top) and protein expression (bottom) in the cortex of AOM-treated mice at various stages of neurological decline including prior to neurological decline (Pre), when minor neurological decline is evident (Minor), when major neurological decline is evident (Major) and at coma (Coma) are shown. Referring to FIG. 11B, relative Cyp46A1 mRNA expression (top) and protein expression (bottom) in the cortex of Cyp7A1+/+ and Cyp7A1−/− vehicle and AOM-treated mice are shown. Referring to FIG. 11C, relative Cyp46A1 mRNA expression (top) and protein expression (bottom) in the cortex of control and cholestyramine-fed vehicle and AOM-treated mice are shown. Referring to FIG. 11D, relative Cyp46A1 mRNA expression (top) and protein expression (bottom) in the cortex of FXR Mismatch and FXR Morpholino vehicle and AOM-treated mice are shown. Referring to FIG. 11E, relative Cyp46A1 mRNA expression (top) and protein expression (bottom) in primary mouse neurons treated with 10 µM DCA and/or 10 µM guggulsterone (Guggul) are shown. *=$p<0.05$ compared to vehicle treated mice of the respective group, #=$p<0.05$ compared to AOM-treated Cyp7A1+/+, FXR Mismatch mice or DCA-treated primary neurons.

Figure 12A:
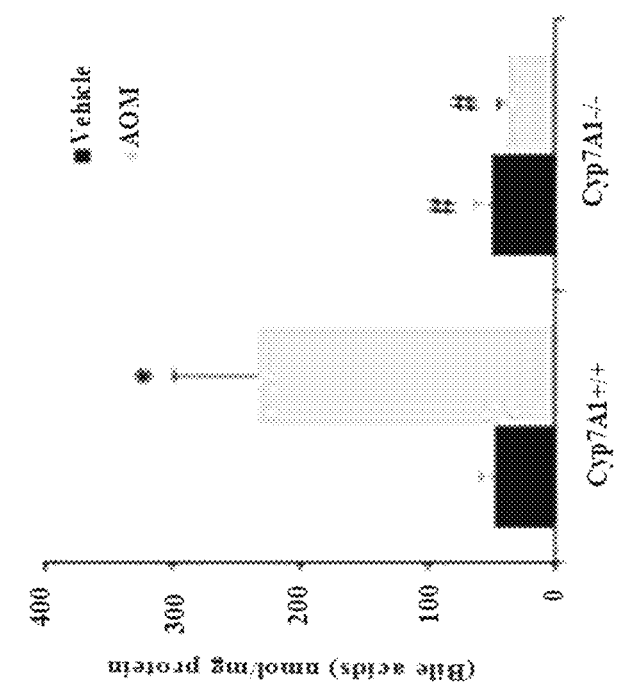
FIG. 12A-E show representative data demonstrating that genetic ablation of Cyp7A1 reduces AOM-induced cholesterol accumulation in the brain.
Figure 12B:
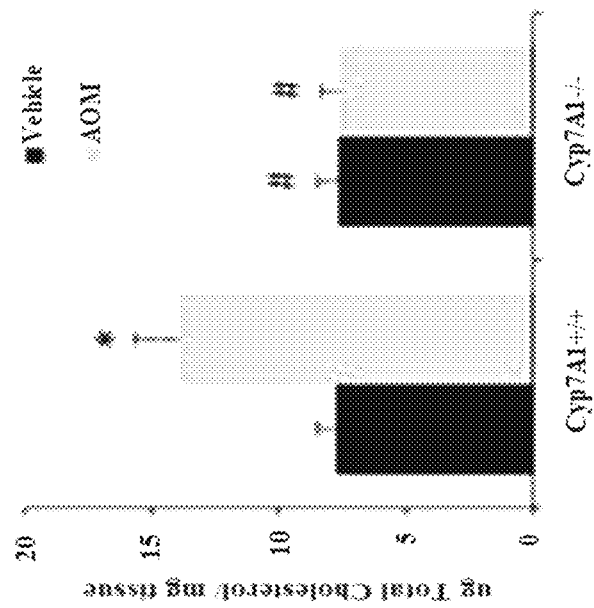
Figure 12C:
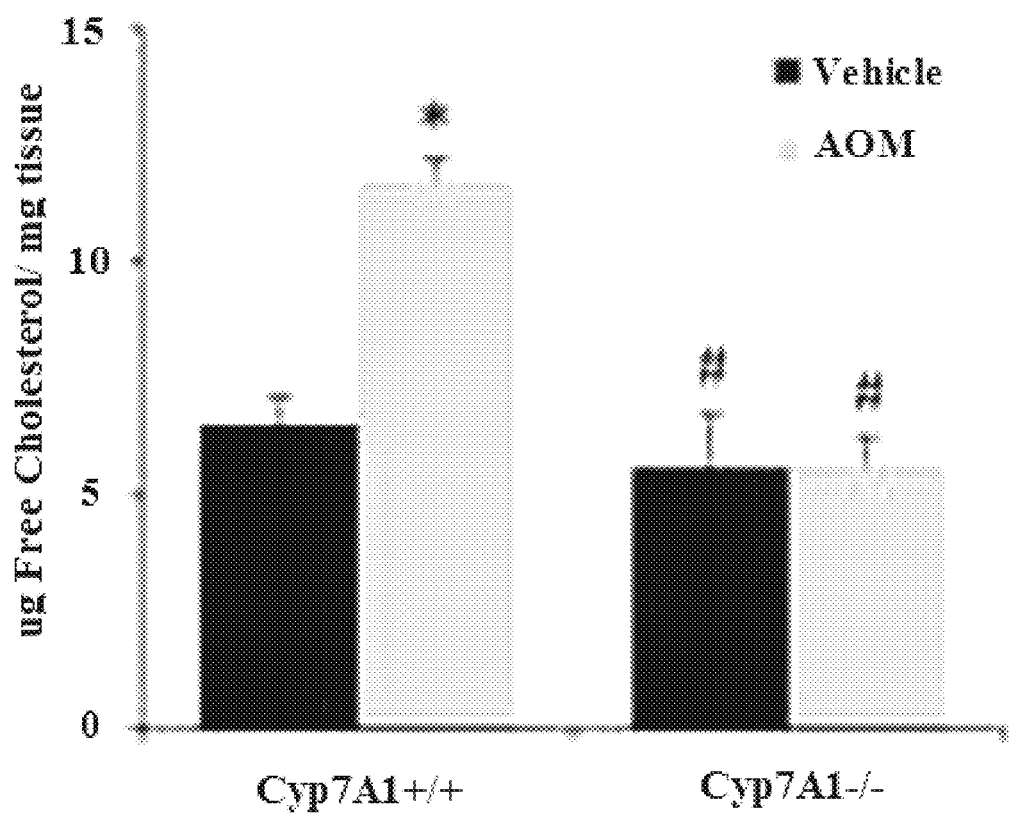
Figure 12D:
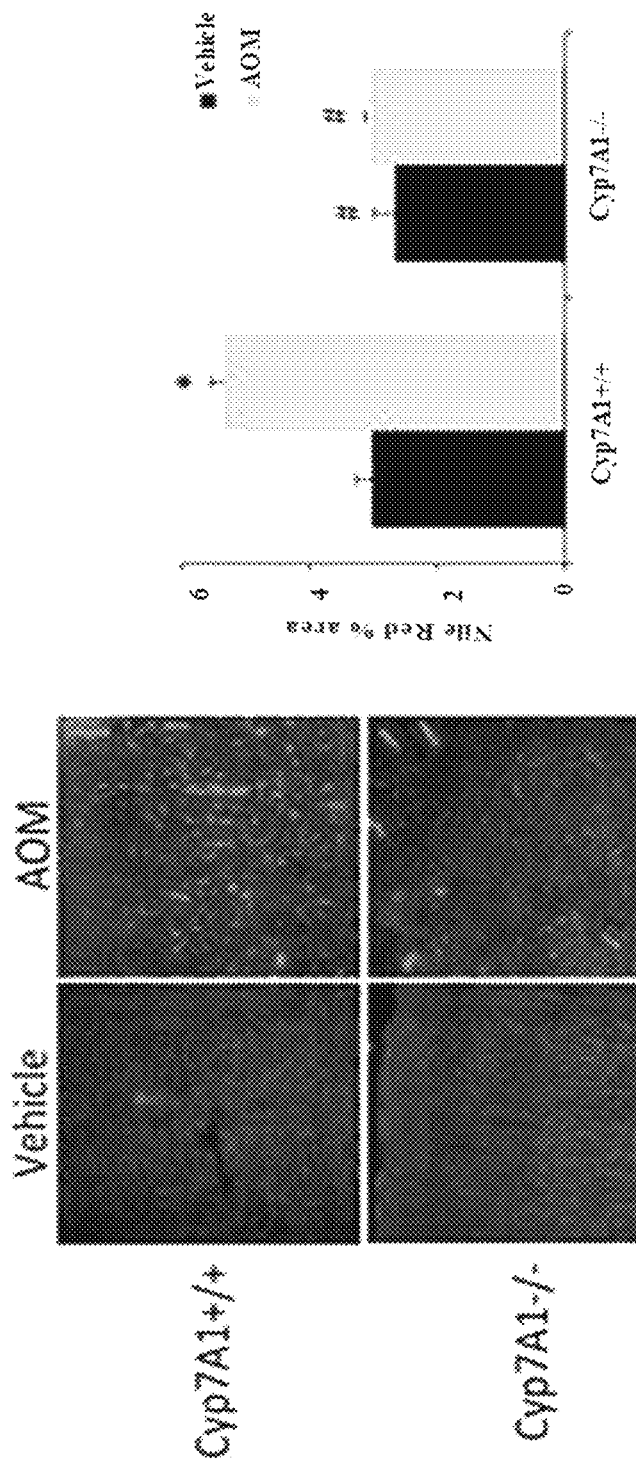
Figure 12E:
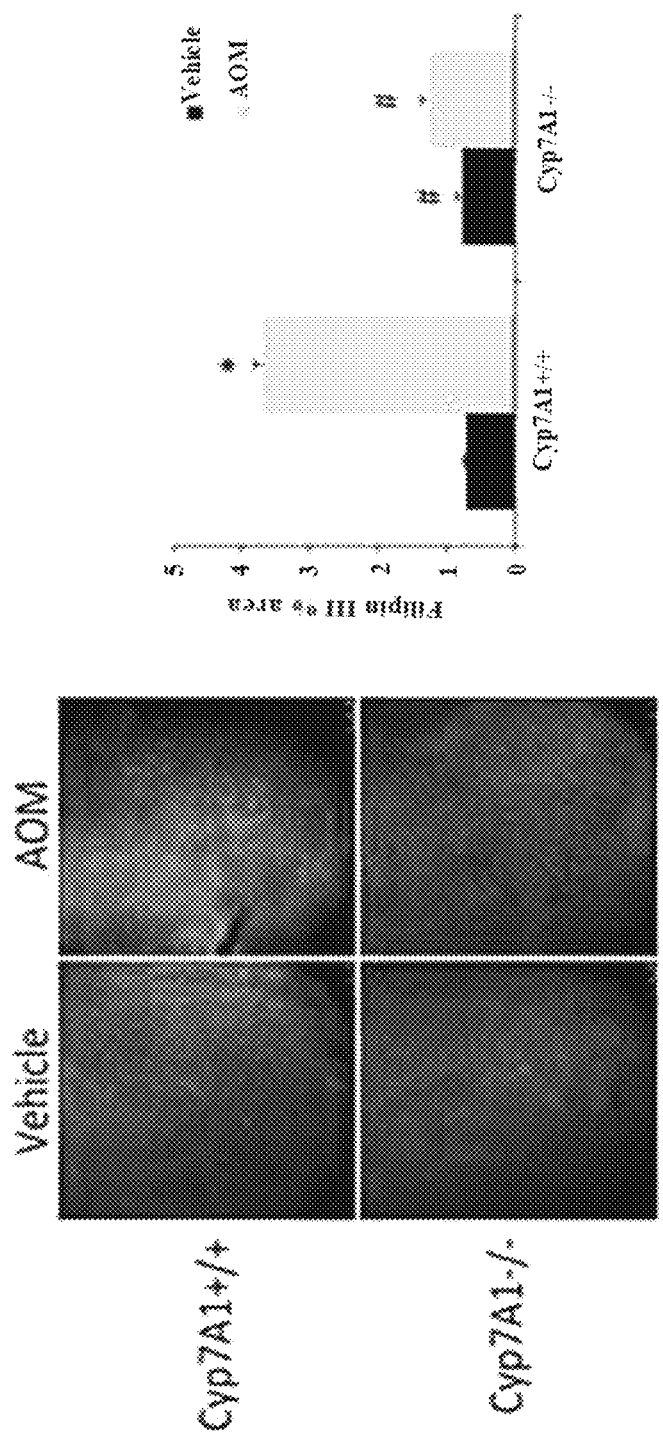

5. Reducing a Cortical Bile Acid Levels Alleviates Cholesterol Accumulation in AOM-Treated Mice The pathway mediated by Cyp46A1 is a primary method regulating cholesterol homeostasis in the brain (Lund, E. G. et al. (2003) *J. Biol. Chem.* 278(25): 22980-8). Therefore, it was assessed whether preventing the suppression of Cyp46A1 expression in mouse models where aberrant cortical bile acid signaling was attenuated could influence the degree of cholesterol buildup. Initially Cyp7A1−/− mice were assessed during AOM-induced hepatic encephalopathy for their relative increase of cortical bile acids compared to Cyp7A1+/+ (WT) mice. Concentrations of cortical bile acids were significantly increased in WT AOM-treated mice and this effect was absent in Cyp7A1−/− mice (FIG. 12A). A similar trend was seen regarding cholesterol as an increase in total and free cholesterol content was observed in the WT mice after AOM injection that was not evident in Cyp7A1−/− mice (FIG. 12B and FIG. 12C). Furthermore, the increase in intracellular cholesterol (Nile Red staining; FIG. 12D) and membrane-bound cholesterol (Filipin III staining; FIG. 12E) observed in WT mice after AOM injection was absent in Cyp7A1−/− mice.

Referring to FIG. 12A, bile acid concentrations in the cortex of vehicle and AOM-treated Cyp7A1+/+ and Cyp7A1−/− mice reported as nmol of bile acid per mg of protein are shown. Referring to FIG. 12B and FIG. 12C, total cholesterol levels (FIG. 12B) and free cholesterol levels (FIG. 12C) in the cortex of vehicle and AOM-treated Cyp7A1+/+ and Cyp7A1−/− mice are shown. Cholesterol levels are expressed as µg of cholesterol per mg of cortex tissue. Referring to FIG. 12D, Nile Red staining and quantification reported as percent area in the cortex of vehicle and AOM-treated Cyp7A1+/+ and Cyp7A1−/− mice are shown. Referring to FIG. 12E, Filipin III staining and quantification reported as percent area in the cortex of vehicle- and AOM-treated Cyp7A1+/+ and Cyp7A1−/− mice are shown. *=$p<0.05$ compared to vehicle-treated Cyp7A1+/+ mice, #=$p<0.05$ compared to AOM-treated Cyp7A1+/+ mice.

Figure 13B:
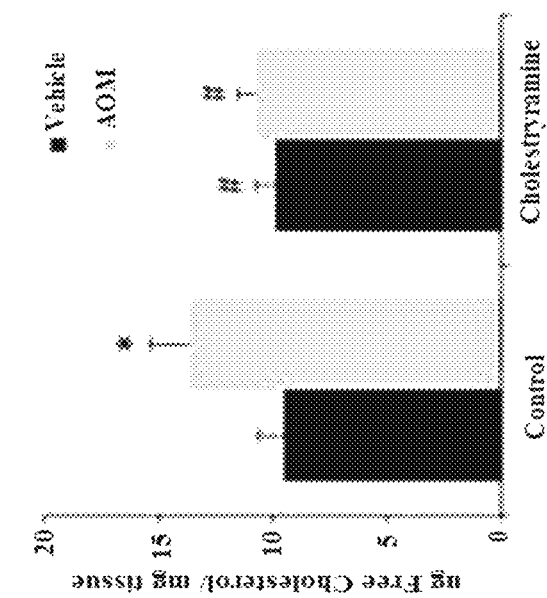
FIG. 13A-E show representative data demonstrating that bile acids induce neural cholesterol accumulation in AOM-treated mice.
Figure 13A:
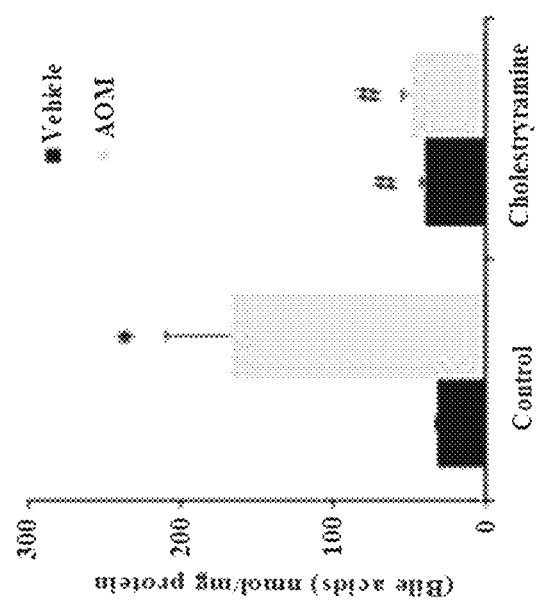
Figure 13C:
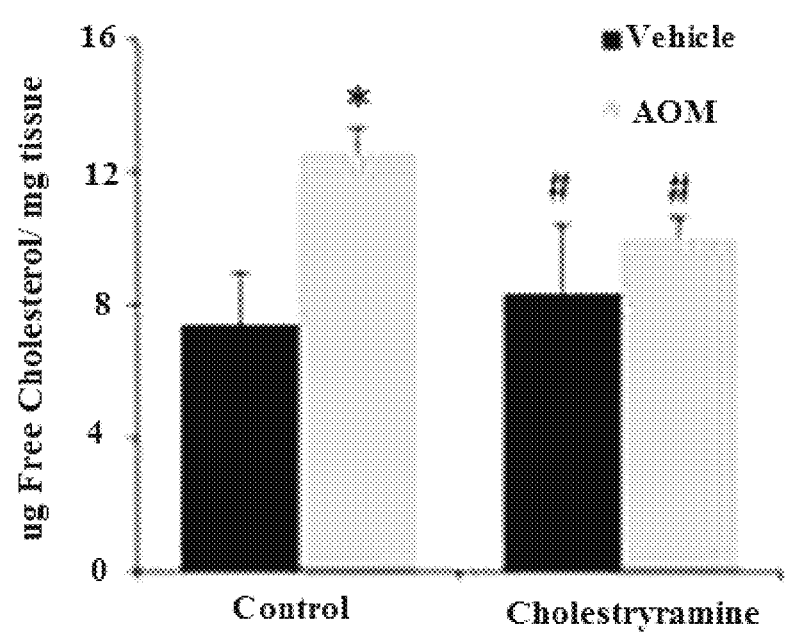

In order to better validate that the effects observed in Cyp7A1−/− mice were due to bile acids alone and not a congenital or strain-specific effect, C57Bl/6 mice were fed a diet supplemented with 2% cholestyramine to reduce bile acid levels. Cholestyramine supplementation was found to significantly reduce the concentration of cortical bile acids in AOM-treated mice compared to the AOM-treated control diet-fed mice (FIG. 13A). This effect correlated with a reduction in total and free cholesterol levels in the AOM-treated cholestyramine-supplemented mice compared to AOM-treated controls (FIG. 13B and FIG. 13C). In addition, the increase in Nile Red (FIG. 13D) and Filipin III staining (FIG. 13E) observed after AOM treatment was reduced by cholestyramine pretreatment, which demonstrates a reduction of intracellular and free cholesterol respectively following cholestyramine supplementation.

Figure 13D:
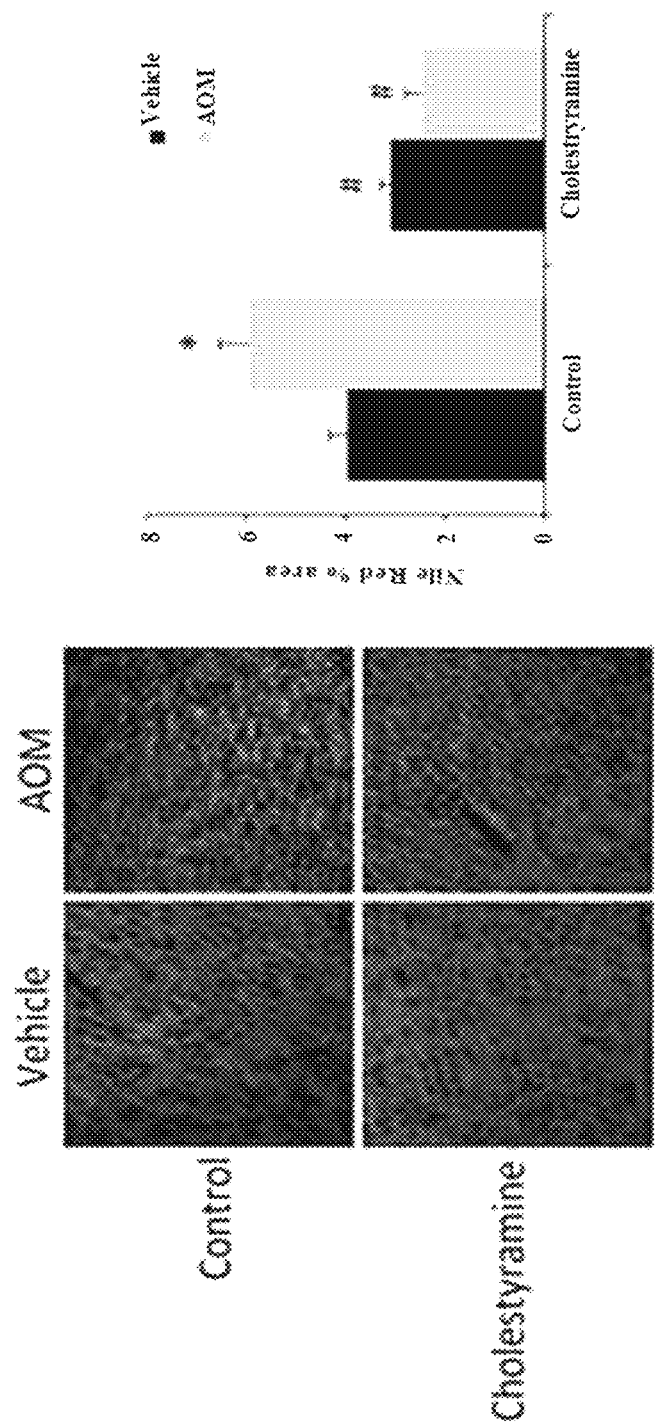
Figure 13E:
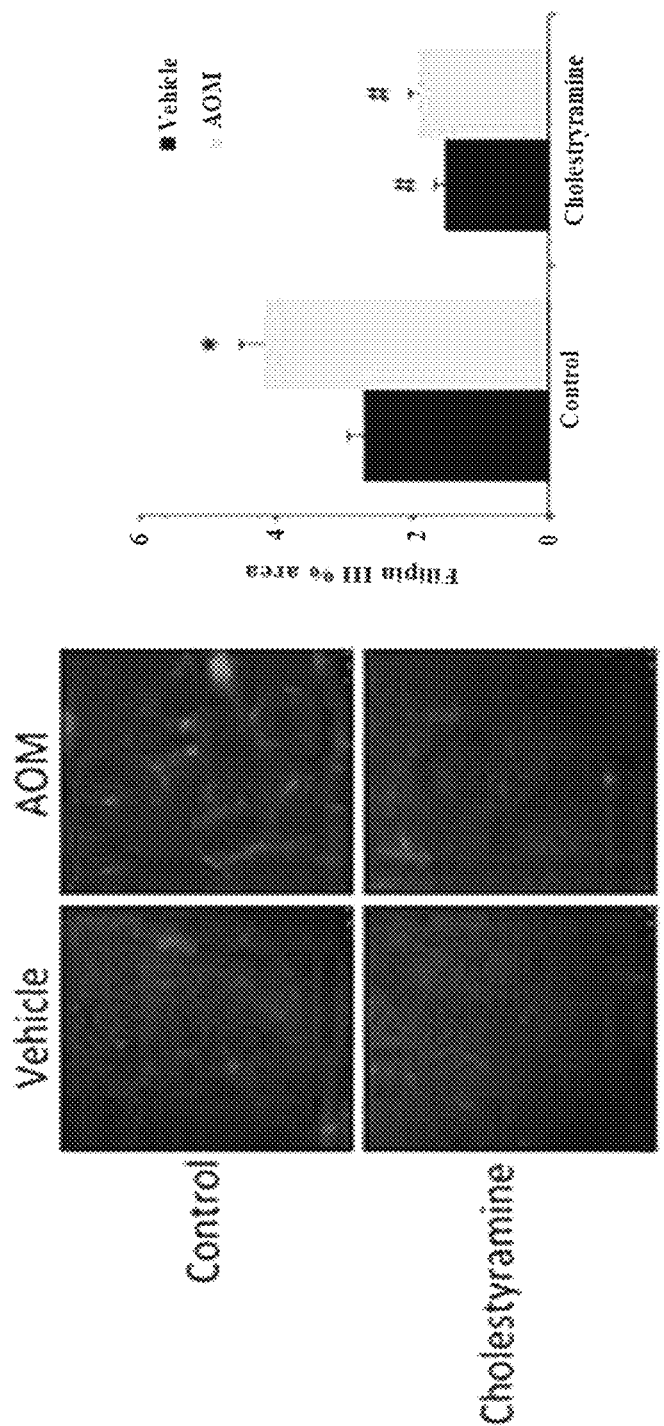

Referring to FIG. 13A, bile acid concentrations in the cortex of vehicle and AOM-treated Cyp7A1$^{+/+}$ and Cyp7A1$^{-/-}$ mice reported as nmol of bile acid per mg of protein are shown. Referring to FIG. 13B and FIG. 13C, total cholesterol levels (FIG. 13B) and free cholesterol levels (FIG. 13C) in the cortex of vehicle and AOM-treated Cyp7A1$^{+/+}$ and Cyp7A1$^{-/-}$ mice are shown. Cholesterol levels are expressed as µg of cholesterol per mg of cortex tissue. Referring to FIG. 13D, Nile Red staining and quantification reported as percent area in the cortex of vehicle and AOM-treated Cyp7A1$^{+/+}$ and Cyp7A1$^{-/-}$ mice are shown. Referring to FIG. 13E, Filipin III staining and quantification reported as percent area in the cortex of vehicle and AOM-treated Cyp7A1$^{+/+}$ and Cyp7A1$^{-/-}$ mice are shown. *=$p<0.05$ compared to vehicle-treated Cyp7A1+/+ mice, #=$p<0.05$ compared to AOM-treated Cyp7A1+/+ mice.

6. FXR Signaling Promotes Cholesterol Accumulation in the Cortex

If bile acids are the primary contributor to the accumulation of cortical cholesterol observed in AOM-treated mice, then this effect could be a result of bile acid receptor-mediated signaling. While bile acids can signal through both G-protein coupled receptors and nuclear receptors, it has been previously demonstrated that FXR is present in neurons and FXR signaling contributes to neurological decline in AOM-treated mice (McMillin, M. et al. (2016) *Am. J. Pathol.* 186(2): 312-23). Therefore, the approach taken was to reduce neuronal FXR protein expression through FXR Morpholino infusion in vehicle and AOM-treated mice and assess cholesterol concentrations. Similar to what was observed in Cyp7A1−/− and cholestyramine-supplemented mice, total and free cholesterol (FIG. 14A and FIG. 14B), as well as intracellular (FIG. 14C) and membrane-bound (FIG. 14D) cholesterol, were increased in AOM-treated mice infused with a control mismatched Vivo morpholino sequence and this effect was attenuated in mice infused with FXR Morpholino.

Figure 14B:
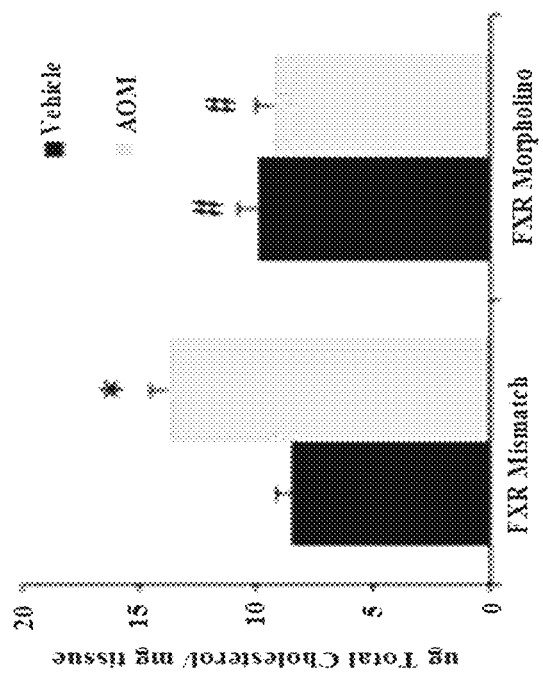
FIG. 14A-D show representative data demonstrating that FXR exacerbates neural cholesterol accumulation in AOM-treated mice.
Figure 14A:
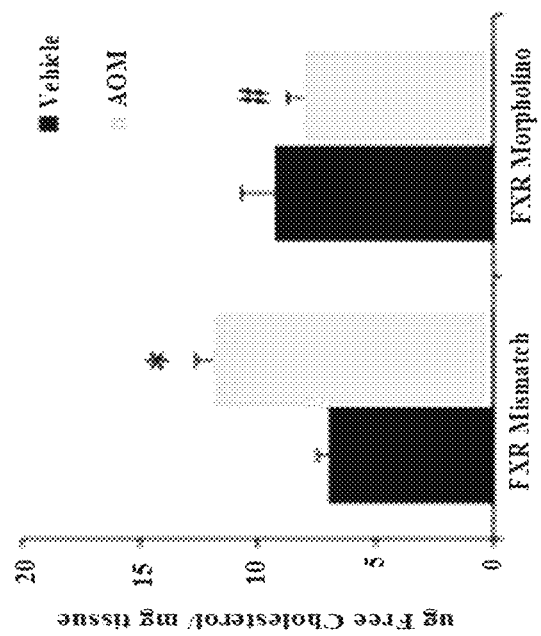
Figure 14C:
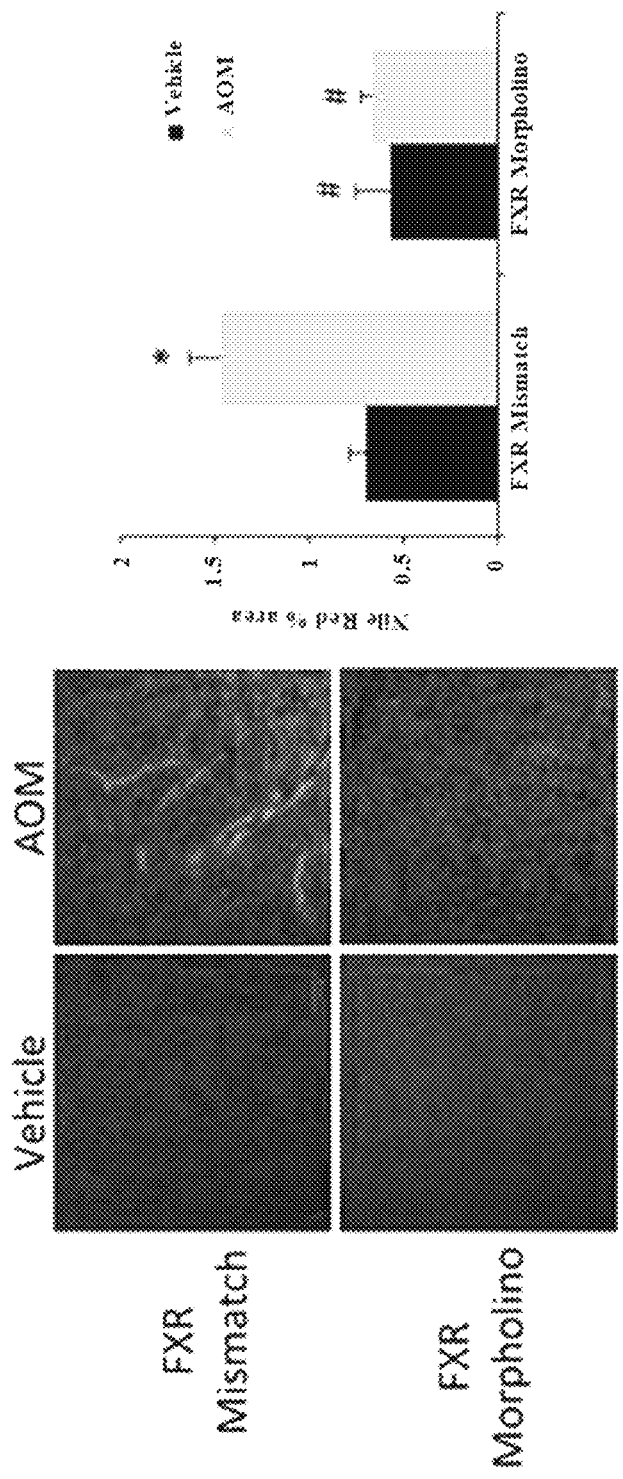
Figure 14D:
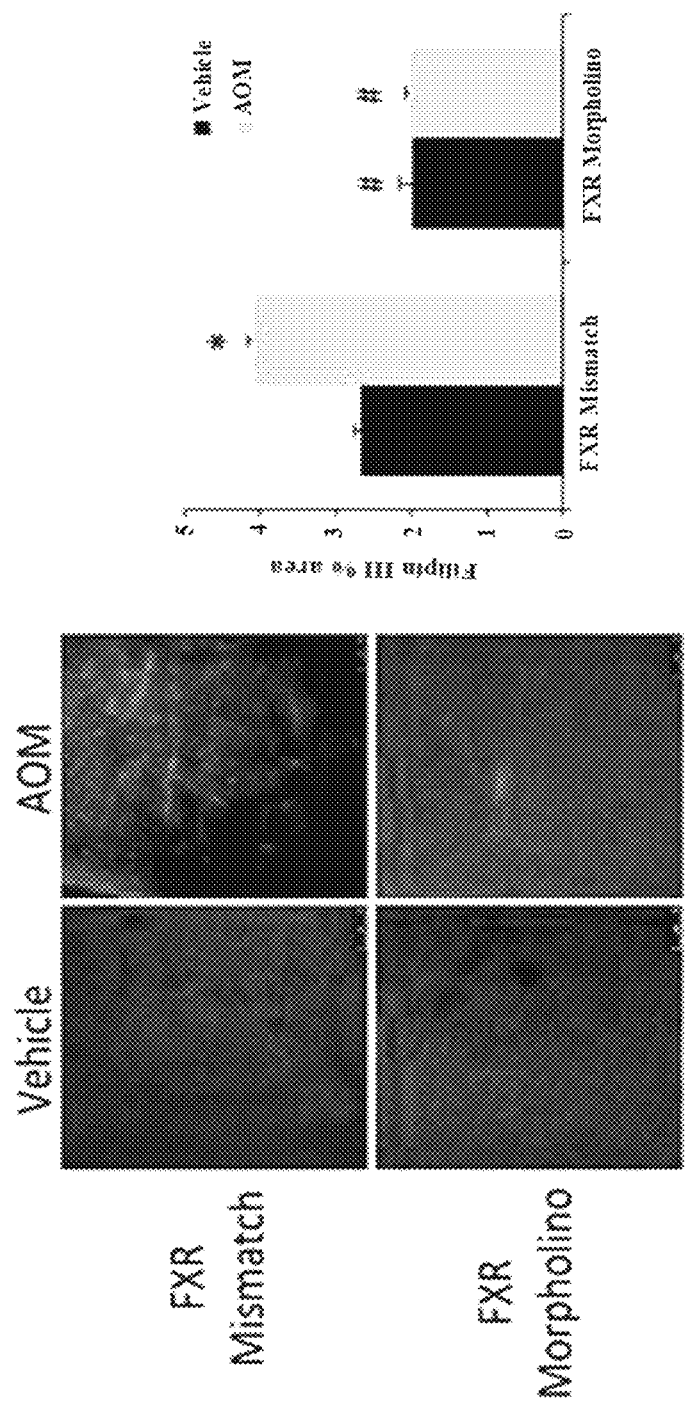

Referring to FIG. 14A and FIG. 14B, total cholesterol levels (FIG. 14A) and free cholesterol levels (FIG. 14B) in the cortex of vehicle and AOM-treated FXR Mismatch and FXR Morpholino-infused mice are shown. Cholesterol levels are expressed as µg of cholesterol per mg of cortex tissue. Referring to FIG. 14C, Nile Red staining and quantification reported as percent area in the cortex of vehicle and AOM-treated FXR Mismatch and FXR Morpholino-infused mice are shown. Referring to FIG. 14D, Filipin III staining and quantification reported as percent area in the cortex of vehicle and AOM-treated FXR Mismatch and FXR Morpholino-infused mice are shown. *=$p<0.05$ compared to vehicle-treated FXR Mismatchinfused mice, #=$p<0.05$ compared to AOM-treated FXR Mismatch-infused mice.

Figures 15A, 15B:
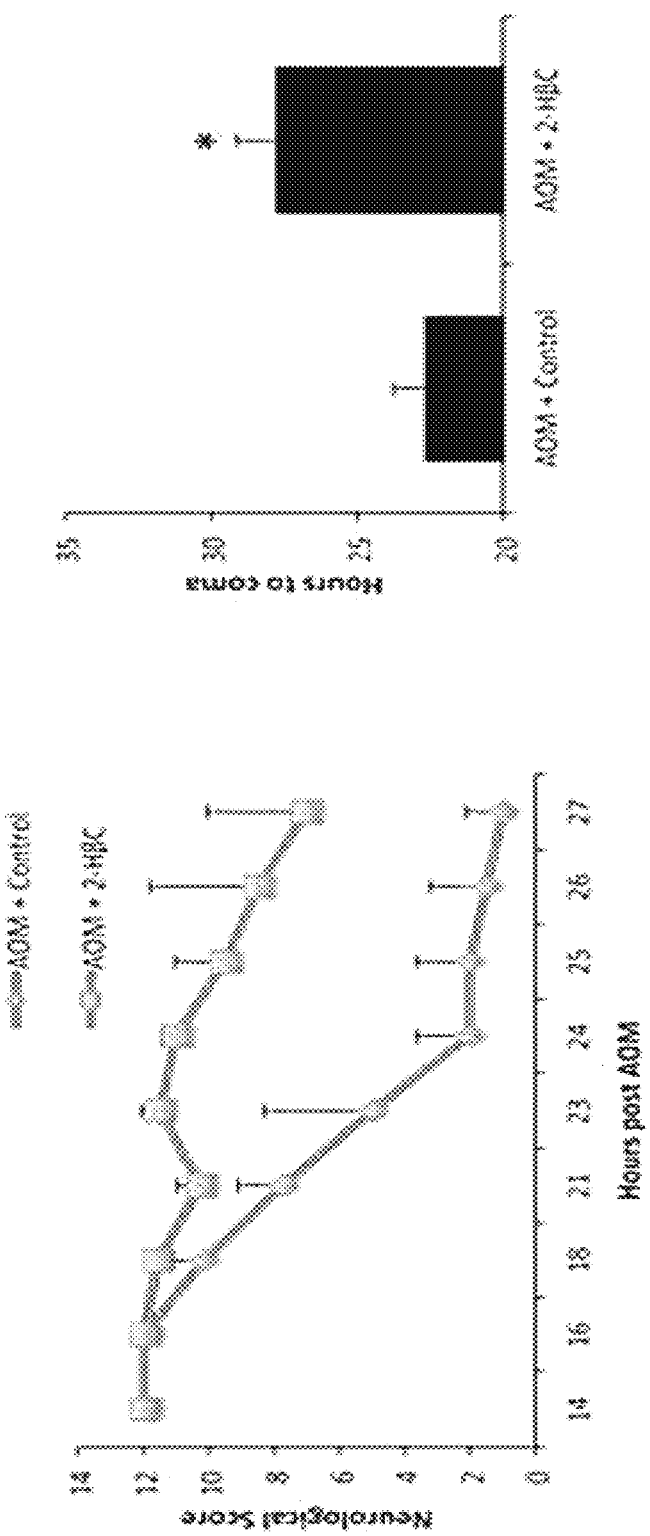
FIG. 15A-E show representative data demonstrating that intracerebroventricular (ICV) infusion of 2-HβC reduces neurological decline in AOM-treated mice.
Figure 15D:
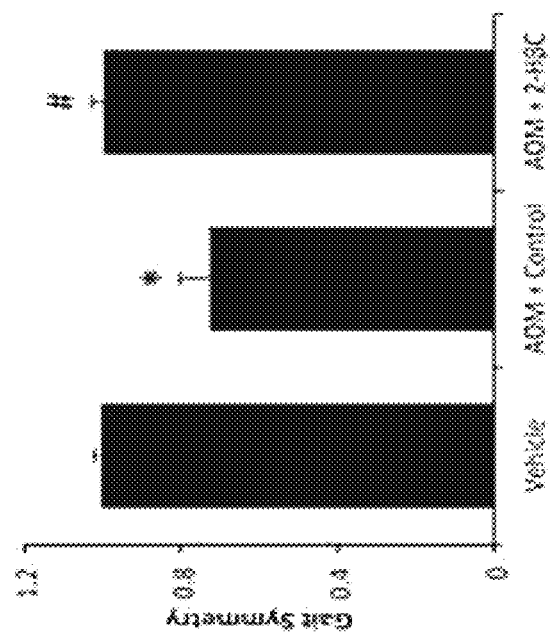
Figure 15C:
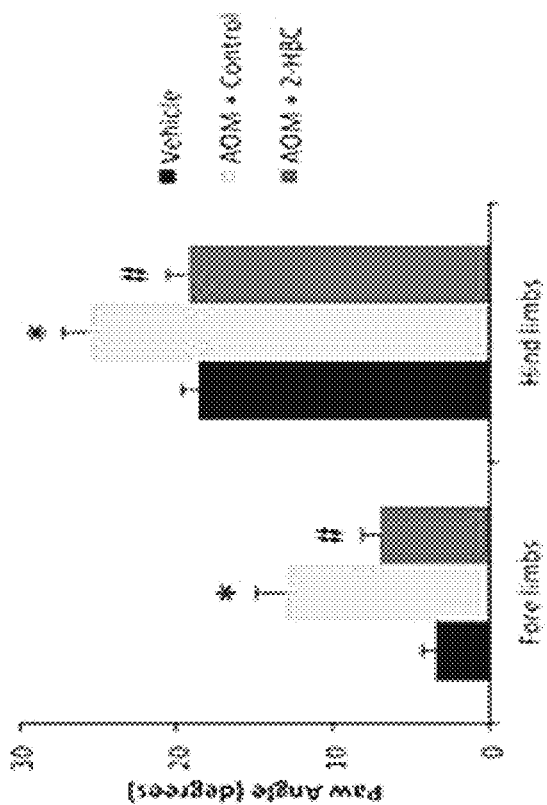
Figure 15E:
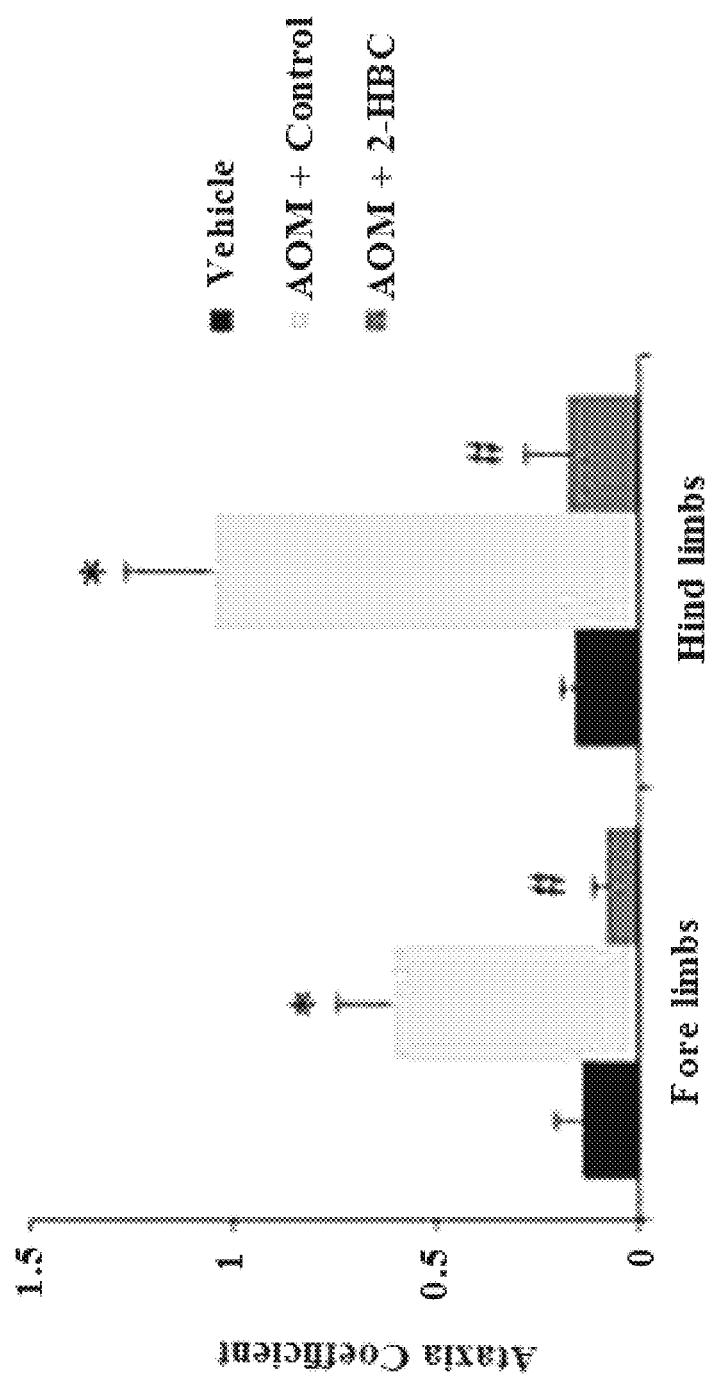

7. Infusion of 2-HBC Reduces Neurological Deficits and Cortical Cholesterol Levels in AOM Treated Mice To determine whether cholesterol buildup in the brain plays a role in the neurological deficits associated with acute liver failure, mice were infused with 2-HβC into the lateral ventricle. Treatment of mice with 2-HβC prior to AOM injection significantly delayed the neurological decline (FIG. 15A) and increased the time taken to reach hepatic coma (FIG. 15B). Besides these neurological measures, neuromuscular complications during hepatic encephalopathy were also assessed. Specifically, control mice walked with a paw angle of approximately 3.5 (forelimb) or 18 (hind limb) degrees of external rotation, which is consistent with previously published studies (Powell, E. et al. (1999) *Physiol. Behav.* 67(5): 819-21) (FIG. 15C). In AOM-treated mice, there was an increased degree of external rotation of both the fore- and hind limbs indicating a splaying of the paws often seen during ataxia (Powell, E. et al. (1999) *Physiol. Behav.* 67(5): 819-21). Treatment with 2-HβC reduced the paw angle of AOM-treated mice to values similar to control (FIG. 15C). Secondly, gait symmetry, defined as the ratio of forelimb stepping frequency to hind limb stepping frequency was effectively 1 in control mice as expected, but this was significantly reduced in mice injected with AOM (FIG. 15D), indicating the mice were stepping more frequently on the hind limbs than forelimbs to compensate for the neuromuscular deficits in the hind limbs. Infusion with 2-HβC prior to AOM injection returned the gait symmetry to control levels (FIG. 15D). Lastly, the ataxia co-efficient, which is an index of step-to-step variability for each limb, was measured. Control mice had a low ataxia co-efficient in both the fore and hind limbs (FIG. 15E), indicating a relatively consistent stride length in all limbs. However, mice with AOM-induced acute liver failure had a significantly higher ataxia co-efficient, indicating a greater variability in stride length, and infusion of 2-HβC returned the ataxia co-efficient back to control levels (FIG. 15E).

Referring to FIG. 15A, neurological score in AOM-treated mice infused with control or 2-HβC is shown. A neurological score of 12 indicates normal function with the score decreasing as neurological impairment occurs. Referring to FIG. 15B, time in hours for AOM-treated control and 2-HβC-infused mice to progress to hepatic coma is shown. Referring to FIG. 15C, paw angle in degrees of the fore and hind limbs of AOM-treated control and 2-HβC-infused mice is shown. Referring to FIG. 15D, gait symmetry of vehicle, AOM-treated control, and AOM-treated 2-HβC-infused mice is shown. Referring to FIG. 15E, ataxia coefficient of the fore and hind limbs of vehicle, AOM-treated control, and AOM-treated 2-HβC-infused mice is shown. *=$p<0.05$ compared to vehicle-treated mice or AOM+control mice for the time-to-coma analysis, #=$p<0.05$ compared to AOM-treated control-infused mice.

Figure 16A:
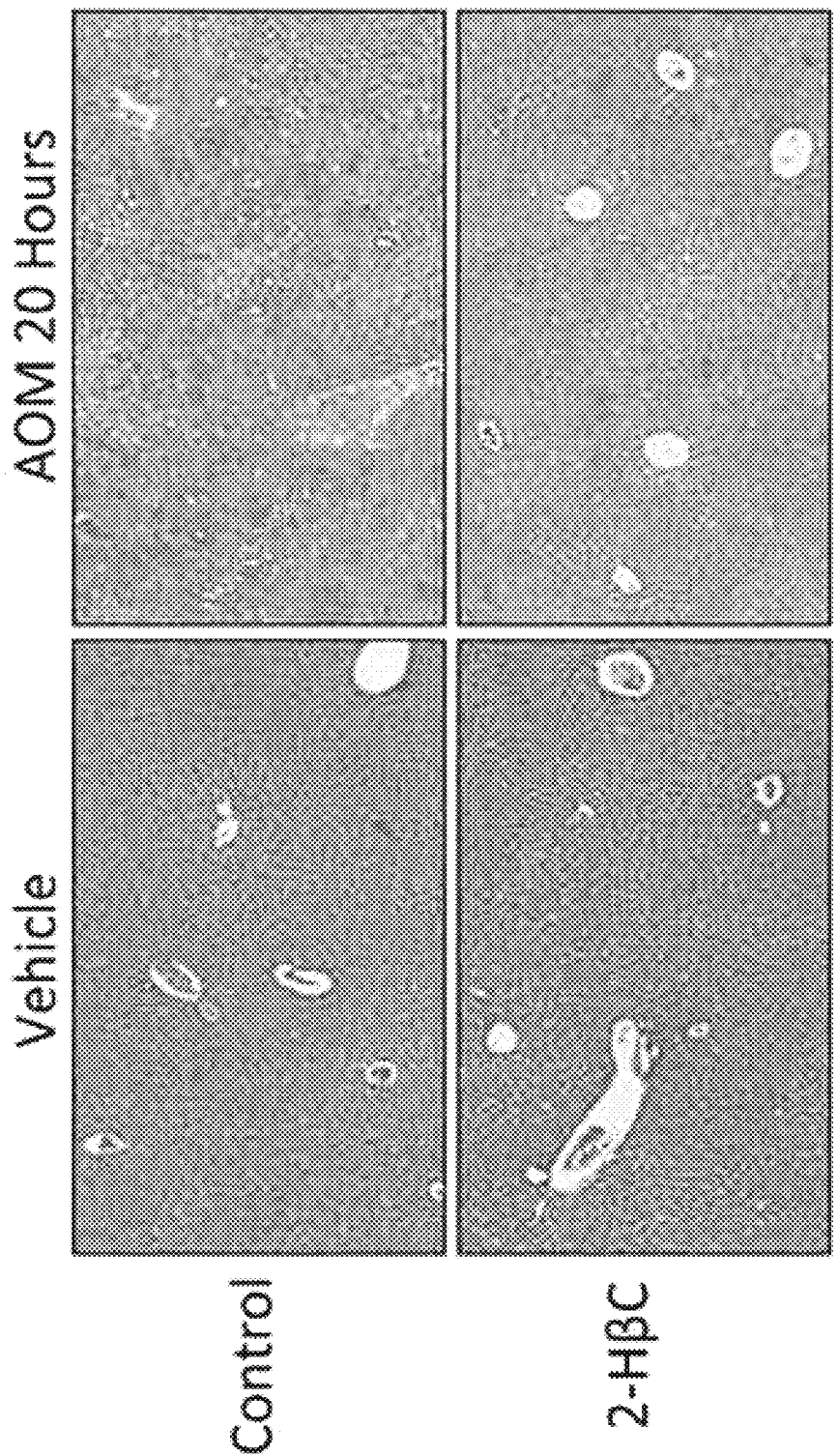
FIG. 16A-C show representative data demonstrating that ICV infusion of 2-HβC does not influence liver function.
Figure 16B:
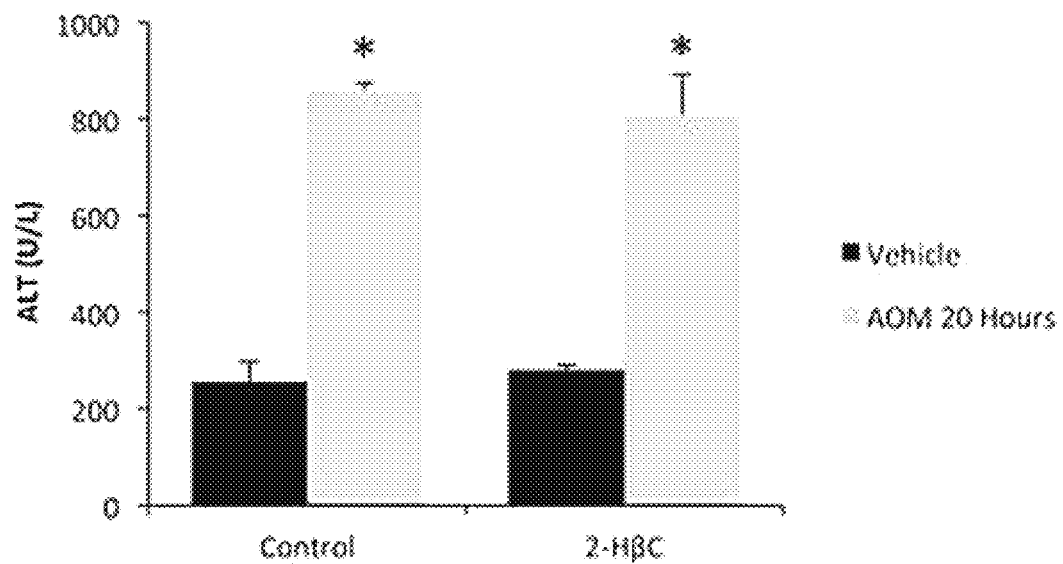
Figure 16C:
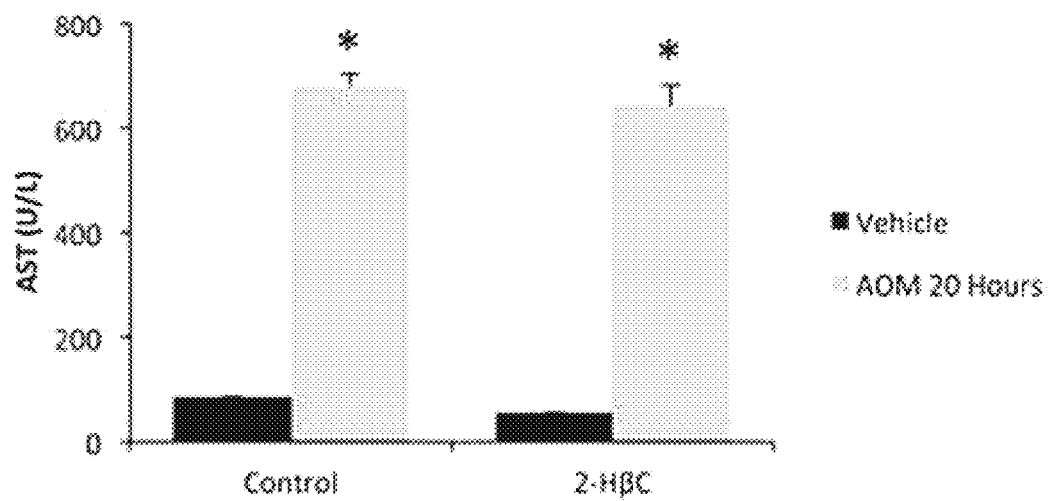

The central infusion of 2-HβC was chosen over systemic administration to allow for the delineation of direct neuroprotective effects of 2-HβC on the development of hepatic encephalopathy, versus the potential indirect hepatoprotective effects which would then impact the subsequent neurological complications. Confirmatory experiments were performed to ensure that the local central infusion of 2-HβC had no effect on the underlying AOM-induced liver damage. The degree of liver damage significantly increased after AOM injection as demonstrated by H&E staining (FIG. 16A), serum ALT (FIG. 16B), and AST (FIG. 16C) to a similar degree as shown previously (McMillin, M. et al. (2016) *Am. J. Pathol.* 186(2): 312-23; McMillin, M. et al. (2017) *Front Cell Neurosci.* 11: 191; McMillin, M. et al. (2014) *Journal of Hepatology* 61(6): 1260-6; McMillin, M. et al. (2016) *J. Neuroinflammation* 13(1): 198) and these results were similar to mice infused with 2-HβC prior to AOM injection (FIG. 16A-C). Without wishing to be bound by theory, these data indicate that central infusion of 2-HβC does not have any hepatoprotective effects against AOM-induced hepatotoxicity and that the protective effects of 2-HβC observed on the development of hepatic encephalopathy are due to the direct actions in the brain.

Referring to FIG. 16A, H&E staining of liver sections from vehicle and 20 hour post-AOM injection mice that were infused with control or 2-HβC are shown. Referring to FIG. 16B and FIG. 16C, ALT (FIG. 16B) and AST (FIG. 16C) concentrations in the plasma of vehicle and 20 hour post-AOM injection mice that were infused with control or 2-HOC are shown. *=$p<0.05$ compared to vehicle-treated control-infused mice.

Lastly, 2-HβC treatment has previously been demonstrated to prevent excessive cholesterol buildup in the brain in models of Niemann-Pick Type C disease without depleting it completely (Davidson, C. D. et al. (2009) *PLoS One* 4(9): e6951). Similarly, 2-HOC infusion into the brain did not decrease the basal levels of cholesterol but did prevent the AOM-induced buildup in total (FIG. 17A) and free (FIG. 17B) cholesterol content in the cortex. Furthermore, 2-HβC treatment attenuated the AOM-induced increase in Nile Red (FIG. 17C) and Filipin III (FIG. 17D) staining. Without wishing to be bound by theory, these data suggest that neuroprotective actions of 2-HβC are likely due to the prevention of cholesterol buildup in the brain and that the increase in cortical cholesterol observed after AOM is likely contributing to the neurological complications of acute liver failure.

Figure 17B:
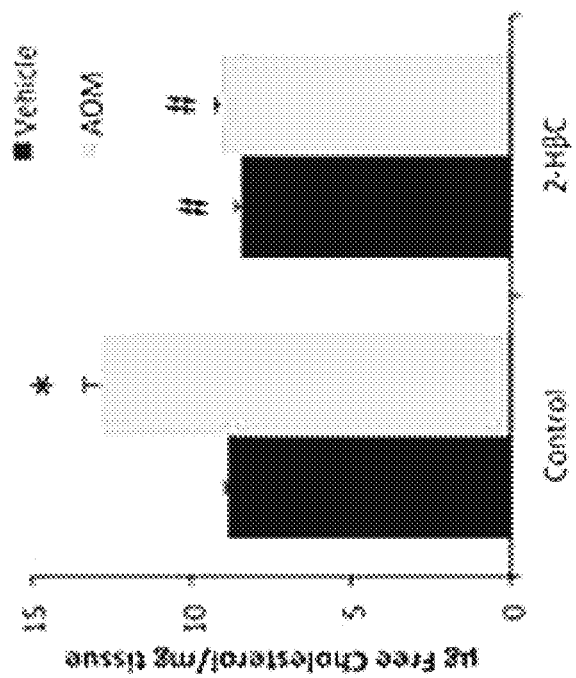
FIG. 17A-D show representative data demonstrating that cortex cholesterol accumulation in AOM-treated mice is reduced by 2-HβC infusion.
Figure 17A:
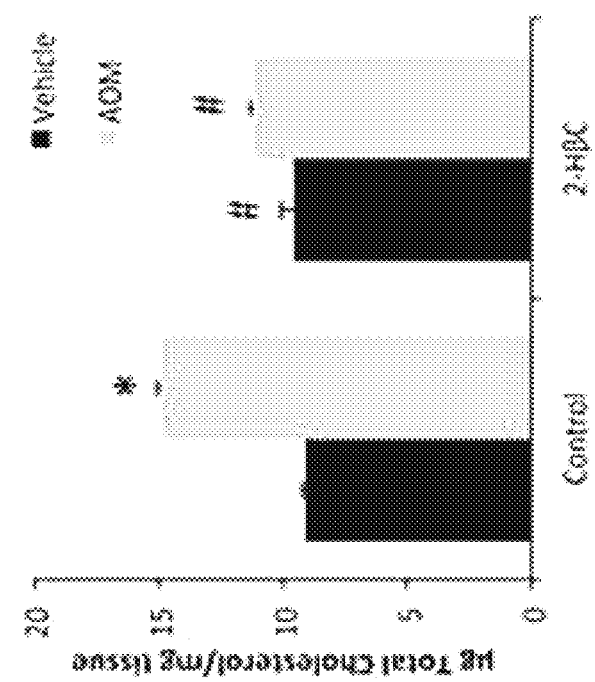
Figure 17C:
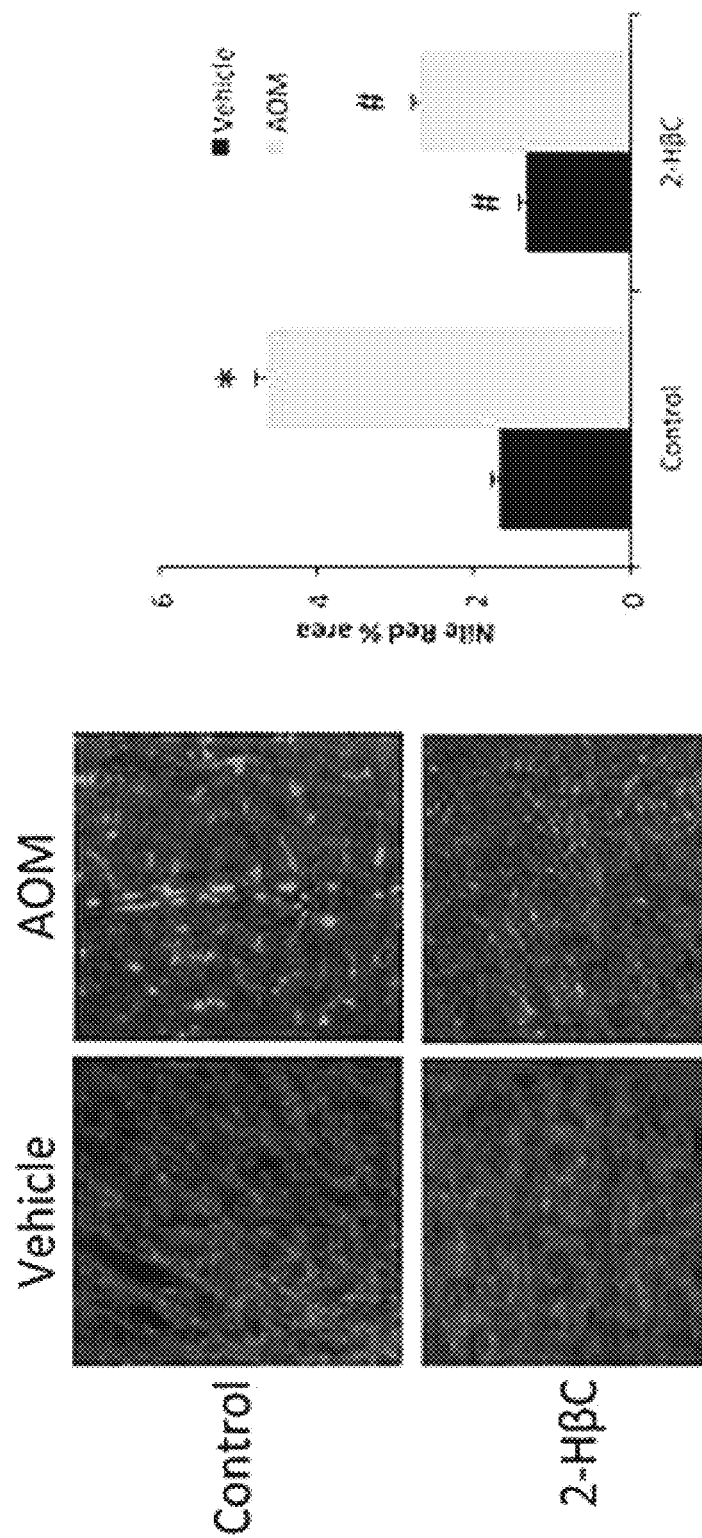
Figure 17D:
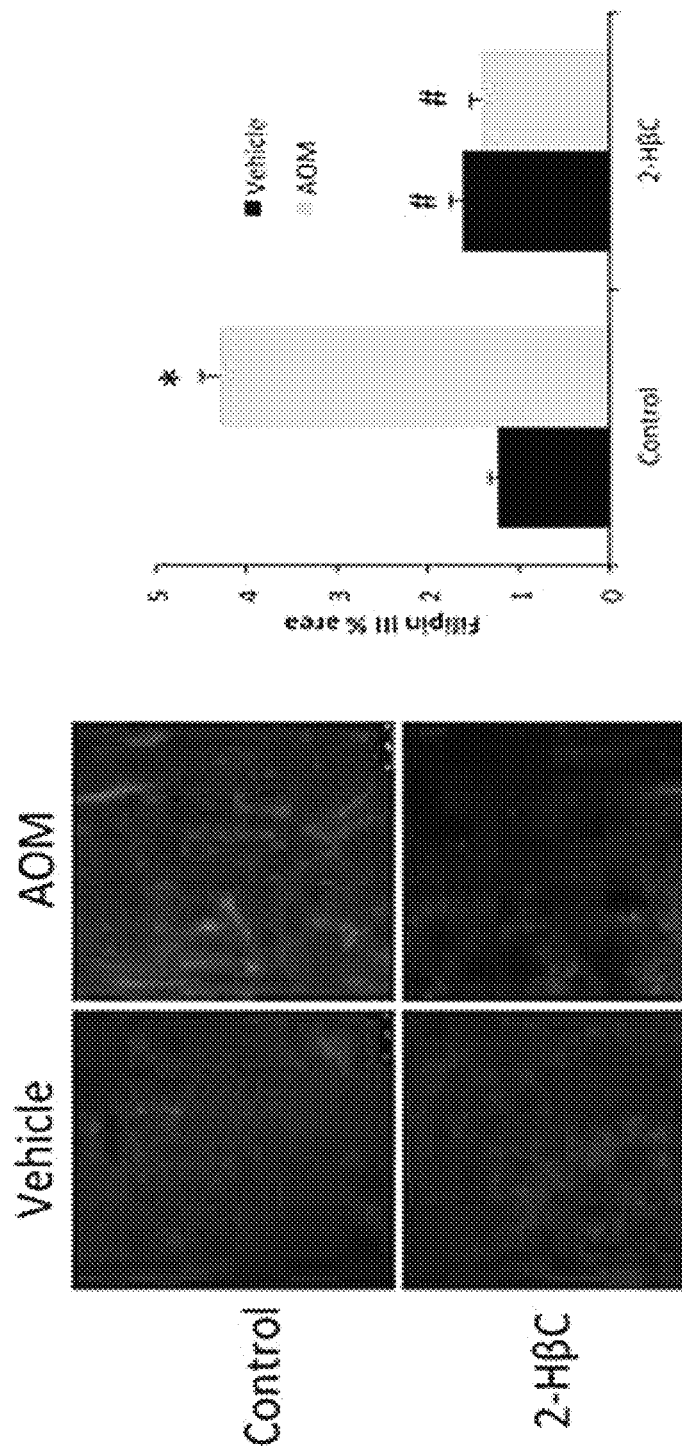

Referring to FIG. 17A and FIG. 17B, total cholesterol levels (FIG. 17A) and free cholesterol levels (FIG. 17B) in the cortex of vehicle and AOM-treated control and 2-HβC-infused mice are shown. Cholesterol levels are expressed as µg of cholesterol per mg of cortex tissue. Referring to FIG. 17C, Nile Red staining and quantification reported as percent area in the cortex of vehicle and AOM-treated control and 2-HβC-infused mice. Referring to FIG. 17D, Filipin III staining and quantification reported as percent area in the cortex of vehicle and AOM-treated control and 2-HβC-infused mice are shown. *=p<0.05 compared to vehicle-treated control-infused mice, #=p<0.05 compared to AOM-treated control-infused mice.

8. Implications on the Pathogenesis of Hepatic Encephalopathy

Without wishing to be bound by theory, the findings of this study pertain to the potential downstream consequences of aberrant bile acid signaling in the brain during acute liver failure and its subsequent role in the development of hepatic encephalopathy. These data suggest that, similar to the liver, FXR signaling in the brain can alter cholesterol homeostasis by regulating Cyp46A1-mediated cholesterol clearance pathways, leading to a buildup up of cholesterol in the brain during acute liver failure. Furthermore, a treatment regime designed to prevent the accumulation of cholesterol had protective effects against the cognitive and neuromuscular dysfunction associated with hepatic encephalopathy. Thus, without wishing to be bound by theory, these data suggest that a downstream consequence of FXR signaling in the brain may be the accumulation of cholesterol, which has implications on the pathogenesis of hepatic encephalopathy.

Here, the AOM model of acute liver injury was used. This model was chosen as i) it is the only model in mice for acute liver failure leading to the development of hepatic encephalopathy recommended by a subcommittee of the International Society of Hepatic Encephalopathy and Nitrogen Metabolism (Butterworth, R. F. (2009) *Liver Int.* 29(6): 783-8); ii) unlike other mouse models, the AOM model of hepatic encephalopathy is reproducible, reversible to a certain degree, has a reasonable therapeutic window, and produces neurological decline ultimately resulting in liver-related death (similar to that observed in humans) as long as the body temperature and other physiological parameters are tightly controlled (Hori, T. et al. (201) *Annals of Gastroenterology: Quarterly Publication of the Hellenic Society of Gastroenterology* 24(4): 294-306); and iii) use of other common clinically relevant drugs involved in drug-induced liver failure, such as acetaminophen, do not cause hepatic encephalopathy in mice. Recently, it has been suggested that AOM is a flawed model of hepatic encephalopathy because AOM may be directly toxic on brain endothelial cells, thereby opening the blood-brain barrier (Jayakumar, A. R. et al. (2013) *Arch. Biochem. Biophys.* 536(2): 171-5). However, it was recently demonstrated that direct treatment of endothelial cells with AOM in vitro does not lead to increased monolayer permeability when these cells were co-cultured with primary astrocytes (McMillin, M. A. et al. (2015) *Laboratory Investigation: A Journal of Technical Methods and Pathology* 95(8): 903-13). In addition, increased permeability of the blood-brain barrier after AOM in vivo occurs at the later stages of encephalopathy well beyond the onset of neurological symptoms (McMillin, M. A. et al. (2015) *Laboratory Investigation: A Journal of Technical Methods and Pathology* 95(8): 903-13; Nguyen, J. H. et al. (2006) *J. Hepatol.* 44(6): 1105-14) and is dependent upon a certain degree of systemic inflammation (Chastre, A. et al. (2013) "Lipopolysaccharide precipitates hepatic encephalopathy and increases blood-brain barrier permeability in mice with acute liver failure" *Liver Int*). Without wishing to be bound by theory, these in vivo reports do not support the idea that AOM is directly causing leakiness of the blood-brain barrier, but rather is a consequence of liver failure and the resulting complications that arise.

The current understanding of the pathogenesis of hepatic encephalopathy has largely focused on the buildup of serum and cortical ammonia during acute liver failure, which can act synergistically with peripheral and central inflammation to precipitate the neurological difficulties observed during hepatic encephalopathy (Chastre, A. et al. (2010) *Metab. Brain Dis.* 25(1): 17-21; Felipo, V. et al. (2012) *Metab. Brain Dis.* 27(1): 51-8). However, the increase of circulating bile acids observed after liver damage has been identified as another possible culprit contributing to the complex etiology of hepatic encephalopathy (McMillin, M. et al. (2016) *Am. J. Pathol.* 186(2): 312-23; McMilin, M. et al. (2017) *Front Cell Neurosci.* 11: 191; Acharya, and Bajaj (2017) *Gastroenterol. Clin. North Am.* 46(1): 155-69; Horvatits, T. et al. (2017) *Liver Int.* 37(2): 224-31; Kawamata, Y. et al. (2003) *J. Biol. Chem.* 278(11): 9435-40). It has been previously demonstrated that aberrant bile acid signaling in neurons, either through FXR or sphingosine-1 phosphate receptor 2, contributes to the neurological deficits and neuroinflammatory processes observed during acute liver failure (McMillin, M. et al. (2016) *Am. J. Pathol.* 186(2): 312-23; McMilin, M. et al. (2017) *Front Cell Neurosci.* 11: 191). Interestingly, bile acid signaling has recently been implicated in a number of other neurological disorders (McMillin and DeMorrow (2016) *FASEB J.* 30(11): 3658-68), although a common consequence of bile acid signaling in the brain during these neurological disorders is not clear.

The current study was aimed at elucidating the downstream consequences of FXR-mediated signaling and its consequences on cortical cholesterol accumulation. The cortex was the primary brain region investigated as it is functionally impaired during hepatic encephalopathy and previous research has demonstrated that FXR, apical sodium-dependent bile acid transporter and SHP are expressed in cortical neurons and these neurons can transport cholyl-lysyl-fluorescein, a fluorescent bile acid-like substrate, across the cell membrane (McMillin, M. et al. (2016) *Am. J. Pathol.* 186(2): 312-23; Nardone, R. et al. (2016) *Metabolic Brain Disease* 31(5): 1065-70; Chen, Q. F. et al. (2016) *PloS One* 11(3): e0151263). Herein, it is shown that expression of the enzyme Cyp46A1 was downregulated in the cortex during acute liver failure and that strategies to reduce cortical bile acid levels or FXR signaling prevented this downregulation. Cyp46A1 is a brain-specific cytochrome p450 that regulates cholesterol homeostasis by oxidizing cholesterol to 24-(S)-hydroxycholesterol, which can more readily be removed from the brain (Lund, E. G. (2003) *J. Biol. Chem.* 278(25): 22980-8). Notably, these data demonstrate a regulatory effect of both bile acids and FXR-mediated signaling on the expression of Cyp46A1, although the precise mechanism is unknown. It is possible that other FXR ligands or other bile acid receptors influence Cyp46A1 expression and cholesterol accumulation and these topics warrant further investigation. Recent studies have demonstrated that the promoter region of Cyp46A1 is regulated by the transcription factor SP-1 (Milagre, I. et al. (2008) *J. Neurochem.* 106(2): 835-49). Given that a functional interaction has been demonstrated between FXR and SP-1 in the regulation of other genes involved in lipid metabolism (Tu and albers (2001) *Biochem. Biophys. Res. Comun.* 287(4): 921-6), it is conceivable that bile acids could exert their effects on Cyp46A1 expression via the interaction between FXR and SP-1.

Imbalances in cholesterol homeostasis in the brain have been implicated in a number of neurological disorders (Orth and Bellosta (2012) *Cholesterol* 2012: 292598; Vance, J. E. (2012) *Dis Model Mech* 5(6): 746-55). Some disorders, such as Smith-Lemli Opitz Syndrome (DeBarber, A. E. et al. (2011) *Expert Rev. Mol. Med.* 13: e24), and Huntington's Disease (Leoni and Caccia (2015) *Biochim. Biophys. Acta* 1851(8) 1095-105) are associated with a reduction in brain cholesterol, whereas others, such as Niemann-Pick Type C disorder feature an accumulation in cholesterol (Klein, A. D. et al. (2014) *Pediatr. Endocrinol. Rev.* 12 Suppl. 1: 166-75). Consistent with these reports, these data suggest that cholesterol accumulation may also be a component of the pathophysiological processes associated with hepatic encephalopathy. Cholesterol has many functions in the physiological function of the brain. For example, cholesterol is a precursor for the synthesis of neurosteroids such as allopregnanalone and tetrahydrodeoxycorticosterone. Cholesterol is transported into the mitochondria through a translocator protein (TSPO) where the biosynthesis of these neurosteroids occurs. The expression and binding activity of TSPO, as well as neurosteroid synthesis, are upregulated in human and rodent models of hepatic encephalopathy (Butterworth, R. F. (2016) *J. Steroid Biochem. Mol. Biol.* 160: 94-7). Without wishing to be bound by theory, these data suggest that it may be the consequences of aberrant bile acid signaling in the brain leading to an increase in cholesterol that supplies the substrate needed for the increased production of neurosteroids. Secondly, cholesterol is a major component of the cell membrane and can influence the activity of receptors and other signaling molecules (Pucadyil and Chattopadhyay (2006) *Prog. Lipid Res.* 45(4): 295-333). In neurons in particular, the cholesterol content in the membrane can alter neurotransmitter release and the rate of firing of action potentials (Smith, A. J. (2010) *J. Neurosci.* 30(17): 6166-21; Metais, C. et al. (2015) *Neuroscience* 291: 279-8; Cuddy, L. K. et al. (2014) *J. Neurochem.* 128(5): 725-40) and agents that deplete cholesterol from the pre-synaptic membrane increase the frequency of spontaneous neurotransmitter release (Smith, A. J. (2010) *J. Neurosci.* 30(17): 6166-21). Given that the release and activity of a number of neurotransmitter systems are dysregulated in hepatic encephalopathy, it is also conceivable that bile acid-mediated dysregulation of cholesterol homeostasis may be altering neurotransmitter release. Without wishing to be bound by theory, the data presented here indicate that both intracellular and membrane-bound cholesterol are altered in a mouse model of hepatic encephalopathy. Therefore, it is likely that this data has implications in both the enhanced neurosteroid synthesis and altered neurotransmitter function observed in hepatic encephalopathy and further studies are warranted.

Here, a constant central infusion of the cholesterol sequestrant 2-HβC was used to prevent the buildup of cholesterol in the brain. This, and related cyclodextrins, have been proposed as a safe and effective treatment for the management of Niemann-Pick Type C disease (Megias-Vericat, J. E. et al. (2017) *Neurol. Sci.* 38(5): 727-43; Ory, D. S. et al. (2017) *Lancet* 390(10104): 1758-68; Vance and Peake (2011) *Curr. Opin. Lipidol* 22(3): 204-9). Indeed, intrathecal, intracerebroventricular or intravenous administration of cyclodextrins have had proven therapeutic value to varying degrees in clinical trials (Megias-Vericat, J. E. et al. (2017) *Neurol. Sci.* 38(5): 727-43; Ory, D. S. et al. (2017) *Lancet* 390(10104): 1758-68). As stated above, the cannulas were implanted prior to the onset of liver damage and 2-HOC was administered directly into the brain in order to differentiate the direct neuroprotective effects of 2-HβC on hepatic encephalopathy versus the potential indirect protective effects on the liver, which is important to delineate from a mechanistic standpoint. However, further studies are needed to determine the therapeutic potential of 2-HβC for the management of hepatic encephalopathy involving a more feasible route of administration given after the onset of acute liver failure.

In conclusion, the data presented here demonstrate that one potential downstream consequence of aberrant FXR signaling in the brain during hepatic encephalopathy is the accumulation of intracellular and membrane-associated cholesterol. Furthermore, strategies preventing the accumulation of cholesterol proved neuroprotective against the neurological complications of acute liver failure have been demonstrated. Without wishing to be bound by theory, these data suggest that cholesterol may play a novel role in the pathogenesis of hepatic encephalopathy and may prove to be a viable target for the development of novel adjunct therapies for the management of hepatic encephalopathy.

J. PROPHETIC EXAMPLES

1. Methods a. Rodent Models of Type C Hepatic Encephalopathy

Two models of chronic liver disease previously shown will be used to develop mild to moderate HE. BDL surgery will be used in Sprague Dawley rats and CCl4 treatment in C57Bl/6 mice (1 mL/kg by oral gavage twice per week) to generate Type C HE. Pharmacological manipulations (both BDL rat and CCl4 mouse model) and genetic models (CCl4 mouse model only) as described herein will be used. Generally, pharmacological manipulations will commence after the onset of signs of mild neurological impairment (three weeks after BDL surgery in rats and nine weeks after the commencement of CCl4 administration in mice) to mimic the timing of presentation of cirrhotic patients to the clinic. Without wishing to be bound by theory, preliminary data suggest that similar changes in bile acid content, target gene expression, cholesterol accumulation, and neurosteroid synthesis occur when using these two models and therefore, parallel studies in both models will be pursued.

b. Transgenic Mouse Models

FXR fl/fl/SNAP25-Cre: This mouse line has already been generated and is currently actively part of the breeding colony. It was generated by crossing floxed FXR mice with a mouse line expressing SNAP25-Cre. The resulting transgenic mouse line lacks FXR expression in neurons.

ASBT knockout mice: Total body ASBT knockout mice will be purchased from Jackson Laboratories (stock no 005213). Because these mice are total body knockout, their usefulness in differentiating neurological vs hepatic effects of ASBT knockout is limited. These mice will be used only to evaluate bile acid uptake in primary neuronal cultures.

Cyp7A1 knockout mice: Cyp7A1 is a key enzyme responsible for bile acid synthesis via the classical pathway in the liver. These mice have a reduced bile acid pool, with a reduction in specific bile acid species such as DCA and β-muricholic acid, thereby resulting in an altered composition in the bile acid pool. Cyp7A1 is not expressed in the brain. These mice have been used previously to determine if a reduction in the bile acid pool influences the development of HE due to acute liver failure.

Floxed TSPO mice (Jackson Laboratories stock no: 024976): These mice will be used to generate neuronspecific and astrocyte-specific TSPO knockout mice by crossing this line with the mouse line expressing SNAP25-Cre (already existing in the breeding colony) or a GFAP-cre expressing mouse line (Jackson Laboratories Stock no 012886) to distinguish the relative role of neuronal-derived and astrocyte-derived synthesis in the production of neurosteroids during HE.

c. Neurological, Biochemical, and Histological Testing

All treatment groups detailed herein below will undergo the same battery of neurological, biochemical and histological testing. Non-invasive neurological and behavioral testing will be performed periodically for the duration of the experiments (4, 6 and 8 weeks after BDL surgery in rats and 10, 12, 14 and 16 weeks in CCl4-treated mice). Neuromuscular deficits will be assessed using the grip strength meter and Rotarod apparatus. The DigiGait® Gait analysis system will be used to assess indices of ataxia, including paw angle, gait symmetry (ratio of forelimb stepping frequency to hindlimb stepping frequency) and the ataxia co-efficient [(maximum stride length-minimum stride length)/average stride length] as described previously (McMillin et al CMGH in press). Open field tests will be used to measure the locomotor activity and anxiety-like behavior following the protocol described and the novel object recognition test will be used to assess cognitive function in the experimental animals. Tissue and serum will be collected at various time points (4, 6 and 8 weeks after BDL surgery in rats and 10, 12, 14 and 16 weeks in CCl4-treated mice). Liver injury will be assessed with and without pharmacological or genetic manipulations, histologically by H&E staining, TUNEL staining to detect apoptosis, as well as by the presence of key liver enzymes (AST, ALT, bilirubin and alkaline phosphatase) in the serum. Furthermore, cerebral edema (brain water content), arterial ammonia, brain ammonia, microglia activation, and proinflammatory cytokine expression in the liver, serum and brain will be assessed as parameters of HE. In parallel, neurons, microglia, and astrocytes will be isolated by immunoaffinity purification 55 from each treatment group for further analyses.

d. Human Autopsy Samples

Certain key findings will be confirmed in human brain tissue taken at autopsy from cirrhotic patients with hepatic encephalopathy, cirrhotic patients without hepatic encephalopathy, and ageand sex-matched controls. These brain samples were obtained from the Australian Brain Donor Program, a brain bank specifically set up to provide a research resource facility for the collection, characterization, storage and distribution of human brain tissue for research purposes. Currently, this brain bank has paraffin-embedded blocks and snap-frozen tissue from the frontal cortex and cerebellum from 10 patients with hepatic encephalopathy, 10 patients with cirrhosis (without hepatic encephalopathy) and 10 age-matched controls. These samples have been de-identified and no further identifying data will be requested.

2. Circulating Bile Acids Gain Access to the Brain Via the Bile Acid Transporter ASBT During Hepatic Encephalopathy and Alter Neurological Function Via Mechanisms Involving Activation of FXR Without wishing to be bound by theory, it is believed that certain bile acids are increased in the brain during hepatic encephalopathy and are taken up into neurons via the ASBT transporter, where they are able to activate FXR. Here, experiments are proposed to identify the predominant bile acids in the brain during hepatic encephalopathy in rodents and in human samples. Measures will also be employed to enrich the hepatic bile acid pool with various bile acids to determine their effects on the pathogenesis of hepatic encephalopathy. Lastly, a coordinated strategy of genetic and pharmacological methodologies will be used to inhibit ASBT-mediated uptake and subsequent FXR activation in the brain and determine the effects on key features of hepatic encephalopathy.

e. Bile Acids Gain Entry to the Brain and are Taken Up into Neurons Via ASBT-Mediated Transport During Type C HE.

A key feature of HE is a hyper-permeable blood-brain barrier, making the regulation of molecular influx from the periphery to the brain difficult to manage. To this end, it was previously shown that the blood-brain barrier is hyper-permeable to bile acid influx during both chronic and acute liver injury. Herein, strong preliminary data was presented to suggest that the total bile acid content in the cortex and cerebellum is significantly increased in both rodent models of Type C HE as well as in autopsy samples from cirrhotic patients with HE (FIG. 2A-C). This data will be confirmed and the total bile acid content in the serum, CSF, and affected brain regions (frontal cortex, cerebellum, and hippocampus) of our rodent models of Type C HE, as well as in the autopsy brain tissue from the affected areas, will be assessed. Specifically, for the animal studies: (1) ats will undergo sham or BDL surgery. Serum, CSF, and tissue will be collected 4, 6 and 8 weeks after surgery; and (2) mice will be treated with CCl4 (1 mL/kg, via oral gavage twice per week) or vehicle. Serum, CSF, and tissue will be collected at 10, 12, 14 and 16 weeks of treatment. Total bile acid content will be measured in and the individual bile acid species will also be assessed in the serum, CSF, and affected brain regions (frontal cortex, cerebellum and hippocampus) of the above-mentioned treatment groups as well as in the autopsy brain tissue from the affected areas by UPLCIM-MS, a state-of-the-art technique established at Baylor University.

In parallel, the flux of bile acids across the blood-brain barrier will be observed using intravital microscopy. Specifically, at the designated time points, BDL/sham rats or CCl4/vehicle-treated mice will be anaesthetized, and a craniotomy will be performed to expose the pial microvasculature (observed under X40 water immersion lens on a Nikon intravital microscope) as described by Dr. Binu Tharakan (Baylor Scott & White Health, Temple Tex.). Rodents will receive a single intra-orbital injection of the fluorescence bile acid derivative CLF (5 µg/mouse, 10 µg/rat) and images will be captured every 10 minutes after injection. The fluorescence intensity inside and outside the vessels will be determined from multiple areas using nuclear export signal element software. At the end of the experiment, rodents will be transcardially perfused with saline to flush the blood from the vessels and the amount of fluorescence remaining in the tissue will be analyzed using spectrofluorimetry (described previously).

In vitro, the uptake of bile acids into neurons will be assessed in primary neurons isolated from ASBT knockout mice or wildtype (WT) control mice. Briefly, primary neurons from ASBT knockout mice or WT mice will be treated with CLF (5 µg/mL) and the influx observed using confocal microscopy. In parallel, primary neurons will be transiently transfected with the genetically encoded FRET-based bile acid sensors NucleoBAS and CytoBAS48 to detect functional FXR-based bile acid signaling in the nucleus and cytoplasm of neurons, respectively. Neurons will then be treated with the bile acids cholic acid, TCA, DCA, GCA, CDCA, and LCA (1 to 10 µM) and the FXR agonist fexaramine (50 nM) and the dynamics of cellular bile acid influx determined using methodology previously described.

These particular bile acids were chosen as they have been shown to be increased in tissue or in CSF during HE.

Lastly, it will be determined if blocking ASBT transport of bile acids can alter the bile acid content in the brain in rodent models of Type C HE. Unfortunately, the ASBT inhibitors developed to date are nonabsorbable, and therefore are not useful for assessing the role of ASBT expressed in the brain, in the development of HE. The expression of ASBT will be specifically knocked-down in rats and mice using ASBT-specific Vivo morpholino sequences (Genetools, Philomath Oreg.). Specifically: (3) rats will undergo sham or BDL surgery and will be infused with ASBT-specific Vivo morpholino sequence, or mismatched control sequence, (intracerebroventricular; [icy] implanted osmotic minipumps; 1 mg/kg/day) from week 3 to up to week 8 after surgery; and (4) mice will be treated with CCl4 (1 mL/kg, via oral gavage twice per week) or vehicle and will be infused with ASBT-specific Vivo morpholino sequence, or mismatched control sequence, (icy implanted osmotic minipumps; 1 mg/kg/day) starting at approximately 9 weeks after the commencement of CCl4 treatment. ASBT knockdown will be confirmed using qPCR, immunoblotting and immunohistochemistry. Bile acid content in the various brain regions will be evaluated, and in a subset of animals, the uptake of CLF will be assessed using intravital microscopy as described herein.

f. Modulation of Bile Acid Signaling in the Brain During Liver Cirrhosis Alters the Pathogenesis of Type C HE.

It was previously demonstrated that preventing the serum bile acid buildup or altering the composition of the bile acid pool can influence the development of HE due to acute liver failure. To determine if preventing serum bile acid buildup and/or altering the composition of the bile acid pool after the onset of liver damage can influence the development of Type C HE, rodents will be fed a diet enriched in the bile acid sequestrant cholestyramine, various different bile acid species (at concentrations previously shown not to cause liver toxicity in their own right) or a genetic mouse model with altered bile acid pool content will be used. Specifically: (5) rats will undergo sham or BDL surgery and be fed ad libitum a diet enriched in cholestyramine (2% w/w) or control diet starting at approximately 3 weeks after surgery; (6) mice will be treated with CCl4 (1 mL/kg, via oral gavage twice per week) or vehicle and be fed ad libitum a diet enriched in cholestyramine (2% w/w) or control diet starting at approximately 9 weeks after the commencement of CCl4 treatment; (7) rats will undergo sham or BDL surgery and be fed ad libitum a diet enriched in cholic acid, TCA, CDCA, GCA, (all at 0.2% w/w—a dose chosen to have no direct hepatotoxicity), the protective bile acid ursodeoxycholic acid (UDCA; 2% w/w) or control diet starting at approximately 3 weeks after surgery; (8) mice will be treated with CCl4 (1 mL/kg, via oral gavage twice per week) or vehicle and be fed ad libitum a diet enriched in cholic acid, TCA, CDCA, GCA (all at 0.2%), or UDCA (2% w/w) or control diet starting at approximately 9 weeks after the commencement of CCl4 treatment; and (9) Cyp7A1 knockout mice and WT control will be treated with CCl4 (1 mL/kg, via oral gavage twice per week) or vehicle.

Lastly, the role of ASBT, FXR and SHP (as a downstream indicator of FXR activation) in the neurological decline associated with liver cirrhosis will be assessed. ASBT, FXR and SHP expression will be assessed in the cortex, cerebellum and hippocampus of rodents generated in Groups 1 and 2 as detailed herein as well as in autopsy samples of human brain by qPCR, immunoblotting, and immunohistochemistry. The cellular identity of ASBT and FXR-positive cells in the brain will be assessed by immunofluorescence using NeuN, GFAP and Iba1 as markers of neurons, astrocytes and microglia, respectively, and in isolated cell populations (isolated by immunoaffinity purification) from rodents in treatment Groups 1 and 2 above, by qPCR. The role of ASBT and FXR in the neurological deficits observed during liver cirrhosis will be assessed in groups 3 and 4 above, as well as in the following groups: (10) rats will undergo sham or BDL surgery and will be infused with FXR-specific Vivo morpholino sequence, or mismatched control sequence, (icy implanted osmotic minipumps; 1 mg/kg/day) from week 3 to up to week 8 after surgery; (11) rats will undergo sham or BDL surgery and will be infused with the FXR antagonist guggulsterone (1 nmol/day; icy implanted minipumps) from week 3 to up to week 8 after surgery; (12) neuron-specific FXR mice and floxed FXR control mice will be treated with CCl4 (1 mL/kg, via oral gavage twice per week) or with vehicle; and (13) mice will be treated with CCl4 (1 mL/kg, via oral gavage twice per week) or vehicle and will be infused with guggulsterone, (1 nmol/day; icy implanted minipumps) from week 9 up to week 16 after the commencement of CCl4 treatment.

In all treatment groups described (Groups 1-13), neurological and behavioral impairment will be assessed and biochemical, and histological evidence of liver damage, and features of HE will be evaluated at various time points as described above.

3. Activation of the Bile Acid Nuclear Receptor FXR in the Brain Disrupts Brain-Derived Cholesterol/Bile Acid Homeostasis During Hepatic Encephalopathy Without wishing to be bound by theory, it is believed that once inside the brain, bile acids dysregulate cholesterol/bile acid homeostasis via the activation of FXR receptor. Preliminary data suggests that bile acids are able to exert their effects on neuronal function by activating FXR-mediated signaling, leading to the suppression of the enzymes responsible for the metabolism of cholesterol in the brain. Here, experiments to determine the consequences of FXR activation on cholesterol metabolism using rodent models of hepatic encephalopathy are proposed.

a. Aberrant FXR Activation in the Brain Results in Increased Cholesterol Accumulation During Type C HE.

Preliminary data suggests that downstream of FXR activation is a downregulation of Cyp46A1 in experimental models of HE (FIG. 6). This preliminary data will be confirmed and Cyp46A1 expression assessed in the cortex, cerebellum, and hippocampus from rodent models of Type C HE (Treatment groups 1 and 2), as well as in the autopsy brain tissue from the affected areas by qPCR, immunoblotting, and immunohistochemistry. The cellular identity of Cyp46A1-positive cells in the brain will be assessed by immunofluorescence using NeuN, GFAP, and Iba1 as markers of neurons, astrocytes, and microglia, respectively, and in isolated cell populations (isolated by immunoaffinity purification) from rodents in treatment Groups 1 and 2 above by qPCR. Furthermore, the dependence of FXR expression on the down regulation of Cyp46A1 will be evaluated in vivo by assessing the expression of Cyp46A1 in experimental treatment groups aimed to inhibit the function of FXR (i.e. in treatment groups 10-13).

To determine if bile acid signaling plays a direct role on the suppression of Cyp46A1 expression, primary neurons from WT and neuron-specific FXR knockout mice will be isolated and treated with various concentrations of the bile acids cholic acid, TCA, DCA, GCA, CDCA and LCA (1-10 µM) and the FXR agonist fexaramine (50 nM) in the presence or absence of the FXR inhibitor guggulsterone (100 nM) for up to 24 hr and Cyp46A1 expression will be assessed.

The transcription factor Sp1 is a potent inhibitor of Cyp46A1 expression. Because no canonical FXR consensus DNA-binding site is evident in the promoter region of Cyp46A1, and FXR is suggested to modulate Sp1 transcriptional activity, it is feasible that bile acids may be exerting effects on Cyp46A1 expression by modulating Sp1. Indeed, preliminary data suggest that Sp1 DNA binding activity is increased in the cortex of BDL rats and in CCl4 mice, but not in mice lacking FXR expression in neurons (FIG. 6F and FIG. 6G). Sp1 expression and DNA-binding activity will be assessed in the cortex, cerebellum and hippocampus from rodent models of Type C HE (treatment groups 1 and 2), in the autopsy brain tissue from the affected areas, as well as in experimental treatment groups aimed at inhibiting FXR function (treatment groups 10-13) by qPCR, and immunoblotting (using total and phosphospecific Sp1 antibodies; Abcam, Cambridge Mass.) and DNA-binding activity kits (Active Motif; Carlsbad, Calif.). Furthermore, Sp1 expression and DNA-binding activity will be assessed in primary neurons from WT and neuron-specific FXR knockout mice treated with various concentrations of the bile acids cholic acid, TCA, DCA, GCA, CDCA and LCA (1-10 µM) and the FXR agonist fexaramine (50 nM) in the presence or absence of the FXR inhibitor guggulsterone (100 nM) for up to 24 hr. To determine a role for Sp1 in the suppression of Cyp46A1, the binding of Sp1 to the Cyp46A1 promoter region in primary neurons treated with the bile acids cholic acid, TCA, DCA, GCA, CDCA and LCA (1-10 µM) will be assessed by chromatin immunoprecipitation using the method described previously and, in parallel, the expression of Cyp46A1 will be assessed in neurons treated with cholic acid, TCA, DCA, GCA, CDCA and LCA (1-10 µM) in the presence or absence of mithramycin A (a specific inhibitor of Sp1 activity, 50 nM).

To demonstrate a role for suppressed Cyp46A1 activity in the pathogenesis of Type C HE, rodent models of HE will be treated with an activator of Cyp46A1. Specifically: (14) rats will undergo sham or BDL surgery and will be infused with (S)-Efavirenz (Toronto research chemicals; 0.16 mg/kg/day via icy implanted osmotic minipumps) from week 3 to up to week 8 after surgery; and (15) mice will be treated with CCl4 (1 mL/kg, via oral gavage twice per week) or vehicle and will be infused with (S)-Efavirenz (Toronto research chemicals; 0.16 mg/kg/day via icy implanted osmotic minipumps) from week 9 to up to week 16 after the commencement of CCl4 treatment. Neurological and behavioral impairment will be assessed and biochemical, and histological assessment of liver damage and features of HE will be assessed at various time points as described above.

Cyp46A1 catalyzes the conversion of cholesterol to 24-(S)-hydroxycholesterol. Therefore, it is conceivable that aberrant bile acid signaling in the brain is driving an increase in cholesterol and decrease in 24-(S)-hydroxycholesterol (FIG. 7). This preliminary data will be confirmed and cholesterol (total, esterified, and un-esterified) and 24-(S)-hydroxycholesterol levels will be assessed in the cortex, cerebellum, and hippocampus from rodent models of Type C HE (treatment groups 1 and 2), in the autopsy brain tissue from the affected areas, as well as in the experimental treatment groups aimed at inhibiting FXR function (treatment groups 10-13) and in the experimental treatment groups aimed at activating Cyp46A1 (treatment groups 14 and 15). Cholesterol accumulation will also be assessed in these groups by Nile red staining (stains intracellular cholesterol) and Fillipin III staining (stains membrane-associated cholesterol) and the predominant cell type with cholesterol accumulation will be identified by Co-staining with NeuN, GFAP and Iba1 as markers of neurons, astrocytes and microglia, respectively.

Lastly, to assess the contribution of a cholesterol/24-(S)-hydroxycholesterol imbalance in the development of HE, strategies to deplete cholesterol accumulation or restore the decrease in 24-(S)-hydroxycholesterol in rodent models of HE will be used. Specifically: (16) rats will undergo sham or BDL surgery and will be infused with 2-hydroxypropyl b-cyclodextrin (2-HBC) or 24-(S)-hydroxycholesterol (6 mg/kg/day or 1 mg/kg/day respectively via icy implanted osmotic minipumps) from week 3 to up to week 8 after surgery; and (17) mice will be treated with CCl4 (1 mL/kg, via oral gavage twice per week) or vehicle and will be infused with 2-HBC or 24-(S)-hydroxycholesterol (6 mg/kg/day or 1 mg/kg/day respectively via icy implanted osmotic minipumps) from week 9 to up to week 16 after the commencement of CCl4 treatment. Neurological and behavioral impairment, cholesterol and 24-(S)-hydroxycholesterol levels as well as biochemical and histological assessment of liver damage and features of HE will be assessed at various time points as described above.

b. Bile Acid-Induced Cholesterol Accumulation Drives Aberrant Neurosteroid Synthesis in Type C HE.

As stated above, cholesterol in the brain can be used as a precursor to neurosteroid biosynthesis which is commonly acknowledged to be dysregulated in HE. Preliminary data confirms this (FIG. 8) and further suggests that the aberrant neurosteroid synthesis may be absent in mice lacking neuronal FXR expression. Specifically, the data indicates that there is an upregulation of key proteins in this neurosteroidogenic pathway, TSPO (cholesterol transporter) and Cyp450scc (regulatory enzyme catalyzing cholesterol to pregnanolone) in the cortex of rodent models of Type C HE and in autopsy samples from patients with HE. These preliminary findings will be confirmed and the studies extended to include other susceptible brain regions as follows:

The expression of TSPO and Cyp450scc will be assessed in the cortex, cerebellum, and hippocampus from rodent models of Type C HE (Treatment groups 1 and 2), as well as in the autopsy brain tissue from the affected areas by qPCR, immunoblotting, and immunohistochemistry. The cellular identity of TSPO- and Cyp450scc-positive cells in the brain will be assessed by immunofluorescence using NeuN, GFAP and Iba1 as markers of neurons, astrocytes and microglia, respectively, and in isolated cell populations (isolated by immunoaffinity purification) from rodents in treatment Groups 1 and 2 above, by qPCR. Furthermore, the effect of FXR signaling on the upregulation of TSPO and Cyp450scc will be evaluated in vivo by assessing the expression of these genes in experimental treatment groups aimed at inhibiting the function of FXR (i.e. in treatment groups 10-13) and/or compensate for the dampening of Cyp46A1 expression (i.e. in treatment groups 14-17). In parallel, to demonstrate a functional change in the increased expression of TSPO and Cyp450scc, allopregnanolone and tetrahydrodeoxycorticosterone will be assessed in the brain tissue from these samples using commercially available kits.

TSPO expression has been found in both neurons and astrocytes and pharmacological strategies to inhibit TSPO function have proven effective to manage symptoms of HE in animal models, but have done little to elucidate which cell type is the most affected. Therefore, neuron- and astrocyte-specific TSPO knockout mice will be generated by crossing floxed TSPO with SNAP25-Cre and GFAP-Cre mice, respectively.

(18) Floxed TSPO, TSPO fl/fl/SNAP25-Cre or TSPO fl/fl/GFAP-cre mice will be treated with CCl4 (1 mL/kg, via oral gavage twice per week). Neurological and behavioral impairment, cholesterol and 24-(S)-hydroxycholesterol as well as biochemical, and histological assessment of liver damage and features of HE, will be assessed at various time points as described above.

K. REFERENCES

McMillin M, Frampton G, Quinn M, Ashfaq S, de los Santos M, 3rd, Grant S, et al. Bile Acid Signaling Is Involved in the Neurological Decline in a Murine Model of Acute Liver Failure. Am J Pathol 2016; 186(2):312-23.

McMillin M, Frampton G, Quinn M, Divan A, Grant S, Patel N, et al. Suppression of the HPA Axis During Cholestasis Can Be Attributed to Hypothalamic Bile Acid Signaling. Mol Endocrinol 2015; 29(12):1720-30.

Orth M, Bellosta S. Cholesterol: its regulation and role in central nervous system disorders. Cholesterol 2012; 2012: 292598.

Cartocci V, Servadio M, Trezza V, Pallottini V. Can Cholesterol Metabolism Modulation Affect Brain Function and Behavior? J Cell Physiol 2017; 232(2):281-6.

Lund E G, Xie C, Kotti T, Turley S D, Dietschy J M, Russell D W. Knockout of the cholesterol 24-hydroxylase gene in mice reveals a brain-specific mechanism of cholesterol turnover. J Biol Chem 2003; 278(25):22980-8.

Erickson S K, Lear S R, Deane S, Dubrac S, Huling S L, Nguyen L, et al. Hypercholesterolemia and changes in lipid and bile acid metabolism in male and female cyp7A1-deficient mice. J Lipid Res 2003; 44(5):1001-9.

McMillin M, Frampton G, Grant S, Khan S, Diocares J, Petrescu A, et al. Bile Acid-Mediated Sphingosine-1-Phosphate Receptor 2 Signaling Promotes Neuroinflammation during Hepatic Encephalopathy in Mice. Front Cell Neurosci 2017; 11:191.

McMillin M, Galindo C, Pae H Y, Frampton G, Di Patre P L, Quinn M, et al. Gli1 activation and protection against hepatic encephalopathy is suppressed by circulating transforming growth factor beta1 in mice. Journal of hepatology 2014; 61(6):1260-6.

McMillin M, Grant S, Frampton G, Andry S, Brown A, DeMorrow S. Fractalkine suppression during hepatic encephalopathy promotes neuroinflammation in mice. J. Neuroinflammation 2016; 13(1):198.

Pol A, Luetterforst R, Lindsay M, Heino S, Ikonen E, Parton R G. A caveolin dominant negative mutant associates with lipid bodies and induces intracellular cholesterol imbalance. J Cell Biol 2001; 152(5):1057-70.

Vanier M T, Latour P. Laboratory diagnosis of Niemann-Pick disease type C: the filipin staining test. Methods Cell Biol 2015; 126:357-75.

Frampton G, Invernizzi P, Bernuzzi F, Pae H Y, Quinn M, Horvat D, et al. Interleukin-6-driven progranulin expression increases cholangiocarcinoma growth by an Akt-dependent mechanism. *Gut* 2012; 61(2):268-77.

DeMorrow S, Francis H, Gaudio E, Venter J, Franchitto A, Kopriva S, et al. The endocannabinoid anandamide inhibits cholangiocarcinoma growth via activation of the non-canonical Wnt signaling pathway. American journal of physiology Gastrointestinal and liver physiology 2008; 295(6):G1150-8.

Livak K J, Schmittgen T D. Analysis of relative gene expression data using realtime quantitative PCR and the 2(-Delta Delta C(T)) Method. Methods 2001; 25(4):402-8.

Song P, Rockwell C E, Cui J Y, Klaassen C D. Individual bile acids have differential effects on bile acid signaling in mice. Toxicol Appl Pharmacol 2015; 283(1):57-64.

Powell E, Anch A M, Dyche J, Bloom C, Richtert R R. The splay angle: A new measure for assessing neuromuscular dysfunction in rats. Physiol Behav 1999; 67(5):819-21.

Davidson C D, Ali N F, Micsenyi M C, Stephney G, Renault S, Dobrenis K, et al. Chronic cyclodextrin treatment of murine Niemann-Pick C disease ameliorates neuronal cholesterol and glycosphingolipid storage and disease progression. PLoS One 2009; 4(9):e6951.

Butterworth R F, Norenberg M D, Felipo V, Ferenci P, Albrecht J, Blei A T, et al. Experimental models of hepatic encephalopathy: ISHEN guidelines. Liver Int 2009; 29(6):783-8.

Hori T, Chen F, Baine A M, Gardner L B, Nguyen J H. Fulminant liver failure model with hepatic encephalopathy in the mouse. Annals of gastroenterology: quarterly publication of the Hellenic Society of Gastroenterology 2011; 24(4):294-306.

Jayakumar A R, Ruiz-Cordero R, Tong X Y, Norenberg M D. Brain edema in acute liver failure: role of neurosteroids. Arch Biochem Biophys 2013; 536(2):171-5.

McMillin M A, Frampton G A, Seiwell A P, Patel N S, Jacobs A N, DeMorrow S. TGFbeta1 exacerbates blood-brain barrier permeability in a mouse model of hepatic encephalopathy via upregulation of MMP9 and down-regulation of claudin-5. Laboratory investigation; a journal of technical methods and pathology 2015; 95(8):903-13.

Nguyen J H, Yamamoto S, Steers J, Sevlever D, Lin W, Shimojima N, et al. Matrix metalloproteinase-9 contributes to brain extravasation and edema in fulminant hepatic failure mice. J Hepatol 2006; 44(6):1105-14.

Chastre A, Belanger M, Nguyen B N, Butterworth R F. Lipopolysaccharide precipitates hepatic encephalopathy and increases blood-brain barrier permeability in mice with acute liver failure. Liver Int 2013.

Chastre A, Jiang W, Desjardins P, Butterworth R F. Ammonia and proinflammatory cytokines modify expression of genes coding for astrocytic proteins implicated in brain edema in acute liver failure. Metab Brain Dis 2010; 25(1):17-21.

Felipo V, Urios A, Montesinos E, Molina I, Garcia-Torres M L, Civera M, et al. Contribution of hyperammonemia and inflammatory factors to cognitive impairment in minimal hepatic encephalopathy. Metab Brain Dis 2012; 27(1):51-8.

Acharya C, Bajaj J S. Gut Microbiota and Complications of Liver Disease. Gastroenterol Clin North Am 2017; 46(1): 155-69.

Horvatits T, Drolz A, Roedl K, Rutter K, Ferlitsch A, Fauler G, et al. Serum bile acids as marker for acute decompensation and acute-on-chronic liver failure in patients with non-cholestatic cirrhosis. Liver Int 2017; 37(2):224-31.

Kawamata Y, Fujii R, Hosoya M, Harada M, Yoshida H, Miwa M, et al. A G protein-coupled receptor responsive to bile acids. J Biol Chem 2003; 278(11):9435-40.

McMillin M, DeMorrow S. Effects of bile acids on neurological function and disease. FASEB J 2016; 30(11):3658-68.

Nardone R, De Blasi P, Holler Y, Brigo F, Golaszewski S, Frey V N, et al. Intracortical inhibitory and excitatory circuits in subjects with minimal hepatic encephalopathy: a TMS study. Metabolic brain disease 2016; 31(5):1065-70.

Chen Q F, Chen H J, Liu J, Sun T, Shen Q T. Machine Learning Classification of Cirrhotic Patients with and without Minimal Hepatic Encephalopathy Based on Regional Homogeneity of Intrinsic Brain Activity. PloS one 2016; 11(3):e0151263.

Milagre I, Nunes M J, Gama M J, Silva R F, Pascussi J M, Lechner M C, et al. Transcriptional regulation of the human CYP46A1 brain-specific expression by Sp transcription factors. J Neurochem 2008; 106(2):835-49.

Tu A Y, Albers J J. Functional analysis of the transcriptional activity of the mouse phospholipid transfer protein gene. Biochem Biophys Res Commun 2001; 287(4):921-6.

Vance J E. Dysregulation of cholesterol balance in the brain: contribution to neurodegenerative diseases. Dis Model Mech 2012; 5(6):746-55.

DeBarber A E, Eroglu Y, Merkens L S, Pappu A S, Steiner R D. Smith-Lemli-Opitz syndrome. Expert Rev Mol Med 2011; 13:e24.

Leoni V, Caccia C. The impairment of cholesterol metabolism in Huntington disease. Biochim Biophys Acta 2015; 1851(8):1095-105.

Klein A D, Alvarez A, Zanlungo S. The unique case of the Niemann-Pick type C cholesterol storage disorder. Pediatr Endocrinol Rev 2014; 12 Suppl 1:166-75.

Butterworth R F. Neurosteroids in hepatic encephalopathy: Novel insights and new therapeutic opportunities. J Steroid Biochem Mol Biol 2016; 160:94-7.

Pucadyil T J, Chattopadhyay A. Role of cholesterol in the function and organization of G-protein coupled receptors. Prog Lipid Res 2006; 45(4):295-333.

Smith A J, Sugita S, Charlton M P. Cholesterol-dependent kinase activity regulates transmitter release from cerebellar synapses. J Neurosci 2010; 30(17):6116-21.

Metais C, Hughes B, Herron CE. Simvastatin increases excitability in the hippocampus via a PI3 kinase-dependent mechanism. Neuroscience 2015; 291:279-88.

Cuddy L K, Winick-Ng W, Rylett R J. Regulation of the high-affinity choline transporter activity and trafficking by its association with cholesterol-rich lipid rafts. J Neurochem 2014; 128(5):725-40.

Megias-Vericat J E, Garcia-Robles A, Company-Albir M J, Fernandez-Megia M J, Perez-Miralles F C, Lopez-Briz E, et al. Early experience with compassionate use of 2 hydroxypropyl-beta-cyclodextrin for Niemann-Pick type C disease: review of initial published cases. Neurol Sci 2017; 38(5):727-43.

Ory D S, Ottinger E A, Farhat N Y, King K A, Jiang X, Weissfeld L, et al. Intrathecal 2-hydroxypropyl-beta-cyclodextrin decreases neurological disease progression in Niemann-Pick disease, type CI: a non-randomised, open-label, phase 1-2 trial. Lancet 2017; 390(10104):1758-68.

Vance J E, Peake K B. Function of the Niemann-Pick type C proteins and their bypass by cyclodextrin. Curr Opin Lipidol 2011; 22(3):204-9.

Quinn M, McMillin M, Galindo C, Frampton G, Pae H Y, DeMorrow S. Bile acids permeabilize the blood brain barrier after bile duct ligation in rats via Rac1-dependent mechanisms. Dig Liver Dis 2014; 46:527-534.

Courtney R, Landreth G E. LXR Regulation of Brain Cholesterol: From Development to Disease. Trends Endocrinol Metab. 2016 June; 27(6):404-14.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the treatment of hepatic encephalopathy in a subject in need thereof, the method comprising administering to the subject a therapeutically effective amount of a single active agent, wherein the single active agent is a cyclodextrin selected from a β-cyclodextrin and a γ-cyclodextrin.

2. The method of claim 1, wherein the cyclodextrin is selected from 2-hydroxypropyl-β-cyclodextrin, methylated β-cyclodextrin, hydroxyethyl-β-cyclodextrin, sulfobutylether β-cyclodextrin, and 2-hydroxypropyl-γ-cyclodextrin.

3. The method of claim 1, wherein the cyclodextrin is 2-hydroxypropyl-β-cyclodextrin.

* * * * *